(12) United States Patent
Paka

(10) Patent No.: US 8,193,177 B2
(45) Date of Patent: Jun. 5, 2012

(54) HEPATOCYTE GROWTH FACTOR PATHWAY ACTIVATORS IN FIBROTIC CONNECTIVE TISSUE DISEASES

(75) Inventor: Latha Paka, Elmont, NY (US)

(73) Assignee: Angion Biomedica Corp., Uniondale, NY (US)

( * ) Notice: Subject to any disclaimer, the term of this patent is extended or adjusted under 35 U.S.C. 154(b) by 233 days.

(21) Appl. No.: 12/734,641

(22) PCT Filed: Nov. 13, 2008

(86) PCT No.: PCT/US2008/012722
§ 371 (c)(1), (2), (4) Date: May 13, 2010

(87) PCT Pub. No.: WO2009/064422
PCT Pub. Date: May 22, 2009

(65) Prior Publication Data
US 2010/0256117 A1    Oct. 7, 2010

Related U.S. Application Data

(60) Provisional application No. 61/002,855, filed on Nov. 13, 2007.

(51) Int. Cl.
 A61K 31/55 (2006.01)
 A61K 31/415 (2006.01)
 A61K 31/5377 (2006.01)
 A61K 31/422 (2006.01)
 A61K 31/502 (2006.01)
 A61K 31/541 (2006.01)

(52) U.S. Cl. ............. 514/217.05; 514/228.2; 514/234.5; 514/378; 514/406

(58) Field of Classification Search ............. 514/217.05, 514/228.2, 234.5, 378, 406
See application file for complete search history.

(56) References Cited

U.S. PATENT DOCUMENTS

| | | | |
|---|---|---|---|
| 7,446,199 B2 * | 11/2008 | Aronov et al. | 546/113 |
| 7,453,002 B2 * | 11/2008 | Hangeland et al. | 548/311.7 |
| 7,608,716 B2 * | 10/2009 | Kanazawa et al. | 546/82 |
| 2005/0009876 A1 * | 1/2005 | Bhagwat et al. | 514/338 |

* cited by examiner

*Primary Examiner* — Raymond Henley, III
(74) *Attorney, Agent, or Firm* — Michael A. Yamin

(57) ABSTRACT

Methods are provided for treating fibrotic connective tissue diseases such as scleroderma and conditions such as surgically-induced adhesions using compounds that activate the signaling pathways of hepatocyte growth factor.

22 Claims, 5 Drawing Sheets

Figure 1:
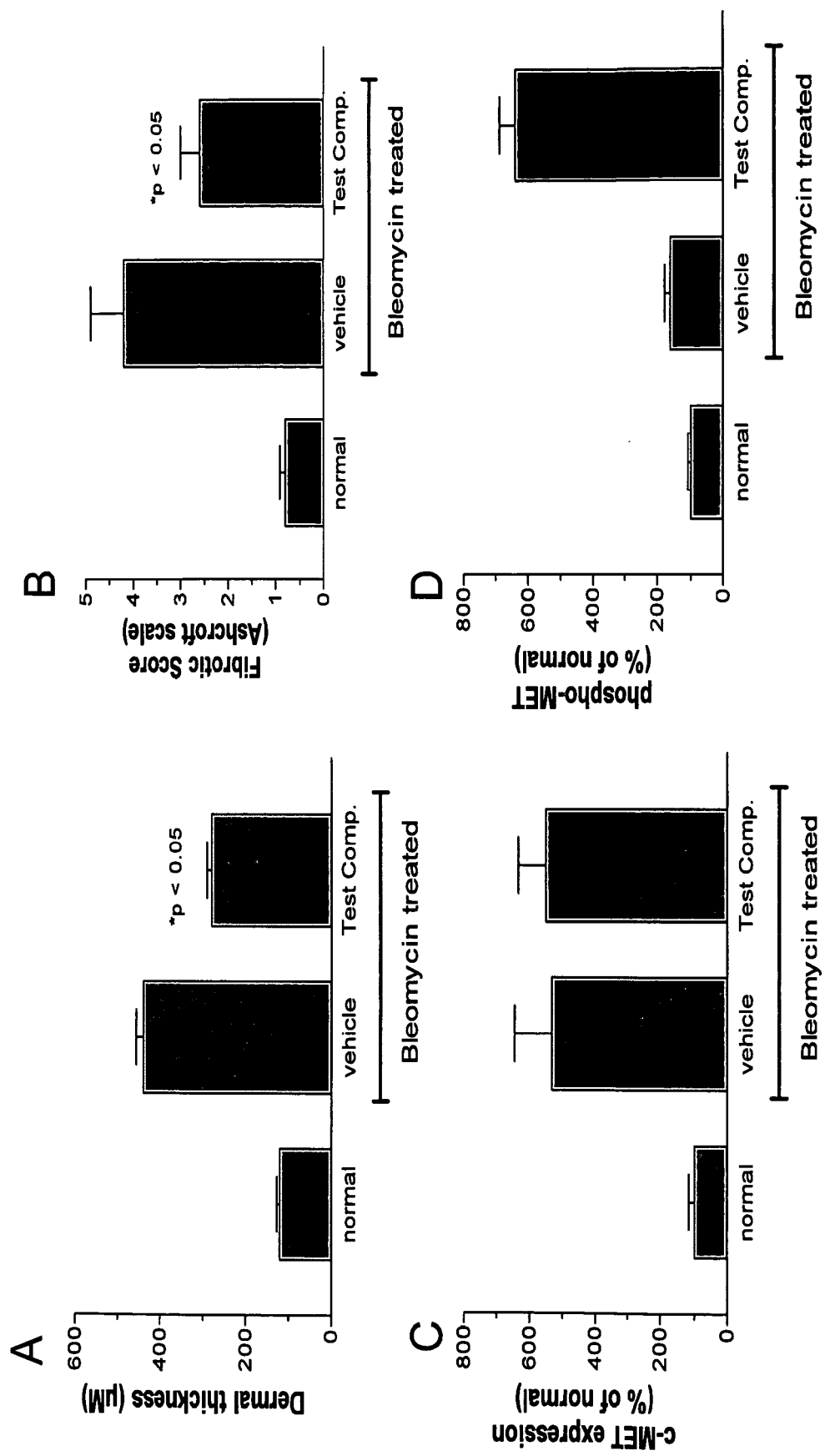

HEPATOCYTE GROWTH FACTOR PATHWAY ACTIVATORS IN FIBROTIC CONNECTIVE TISSUE DISEASES

CROSS-REFERENCE TO RELATED APPLICATIONS

This application is filed under 35 U.S.C §371 of PCT/US2008/012722, filed Nov. 13, 2008, which claims priority to U.S. provisional patent application Ser. No. 61/002,855, filed Nov. 13, 2007, and which are incorporated herein by reference in their entireties.

BACKGROUND OF THE INVENTION

Scleroderma, or fibrosis of the skin, is a disease caused by a surplus of extracellular matrix protein localized in the skin, or it may become systemic (systemic sclerosis) with excess collagen collecting in the kidneys, lungs, gastrointestinal tract, and heart. Scleroderma affects approximately 400,000 people in the United States every year. There is no known cure for scleroderma and the exact cause remains unknown. Treatment is currently limited to management of symptoms in order to improve quality of life and limit long-term complications. Common treatments for scleroderma include anti-fibrotic agents, anti-inflammatory agents, and vasodilators. Immunosuppressive agents such as corticosteroids have demonstrated only marginal efficacy.

The exact cause of scleroderma is unknown but it is thought to be an autoimmune disease. Several studies have shown some evidence of geographic clustering, which is also consistent with possible environmental risk factors. A number of international studies suggest that scleroderma occurs much more frequently in the United States than elsewhere. In addition, diffuse scleroderma appears to occur more frequently among African-American women and starts at an earlier age. These regional differences may be a consequence of differential genetic susceptibility to scleroderma, different exposure to possible environmental triggers, or a combination of both. Scleroderma may occur at any age, but the symptoms most frequently begin in mid-life.

The pathophysiology of scleroderma can be localized or general. Localized scleroderma affects the skin, resulting in appearance of morphia, or hard, oval shaped patches that appear white with a purple ring. Additionally, lines or streaks of thickened skin frequently appear in areas such as the arms, legs or forehead. Generalized scleroderma may affect many parts of the body, and is classified into two types, limited and diffuse. Limited scleroderma occurs gradually, and affects the skin and internal organs, such as the esophagus, lungs, and intestines. Diffuse scleroderma develops more suddenly, with skin thickening throughout the body. Further symptoms include ulcers or sores on fingers, loss of hair over affected areas, or swelling or puffiness in the extremities. More extreme symptoms include arthritis, muscle weakness, and heart and lung complications. According to research studies, the total costs of scleroderma in the United States reach $1.5 billion annually. Morbidity represents the major cost burden, associated with $819 million or over 55% of the total costs. The high cost of scleroderma shows that the burden of rare chronic diseases is often high. The elevated costs reflect a young age of disease onset as well as the need for treatments to decrease morbidity costs. Hence there is a critical need for an effective and affordable therapy.

The pathogenesis of fibrosis in scleroderma involves a complex set of interactions between the fibroblast and its surroundings. Multiple fibrotic pathways are activated for reasons that are not completely understood, but involve immune activation, microvascular damage, and fibroblast transformation into the myofibroblast, the main mediator of extracellular collagen accumulation. After an acute injury has healed, differential proliferation and apoptosis preserve the myofibroblast phenotype rather than leading to a selective depletion of activated fibroblasts. Disproportionate fibroblast activity may result from a combination of possible cellular and matrix defects that include fibrillin protein abnormalities, auto-antibody formation, type II immune response, excessive endothelial response to injury, and excessive fibroblast response to TGFβ1. The ubiquitous growth factor TGFβ1 is the most potent protein involved in collagen gene expression and connective tissue accumulation and its role has been well documented. TGFβ1 is capable of inducing its own expression in a variety of cell types, including dermal fibroblasts which produce TGFβ1, indicates the existence of a possible autocrine feedback loop acting in a paracrine manner. Persistent overproduction of collagen and other connective tissue macromolecules results in excessive tissue deposition, and is responsible for the progressive nature of scleroderma. The rapid expansion of knowledge regarding the effects of cytokines on synthesis of the extracellular matrix has led to an appreciation of the enormous complexity of regulatory networks that operate in the physiologic maintenance of connective tissue and which may be responsible for the occurrence of pathologic fibrosis. Numerous other cytokines, as well as cell-matrix interactions, also modify collagen expression and can significantly influence the effects of TGFβ1.

It is towards the treatment of various fibrotic diseases of connective tissue and in particular of the skin that the present invention is directed.

SUMMARY OF THE INVENTION

The present invention is directed generally to the treatment and prevention of fibrotic diseases of connective tissue such as but not limited to scleroderma, systemic sclerosis, generalized scleroderma and limited scleroderma. Small molecule agents that activate signaling pathways of hepatocyte growth factor (also known as scatter factor; abbreviated HGF) or mimic HGF have been found to be useful in various therapeutic modalities including prophylaxis and treatment of the aforementioned diseases caused by increased fibrosis. Moreover, other conditions such as surgically-induced adhesions including intra-abdominal adhesions following surgery are amenable to treatment by the compounds embodied herein. These agents and compounds can be subdivided into the following categories, each of which will be described in further detail below: 1) compounds and pharmaceutical compositions described in WO2004/058721 and U.S. Pat. Nos. 7,250,437; 7,192,976 and 7,265,112, which are incorporated herein by reference in its entirety; 2) compounds and pharmaceutical compositions described in WO02/002593 and U.S. Pat. Nos. 6,589,997; 6,610,726 and 6,855,728 which are incorporated herein by reference in their entireties; and 3) compounds and pharmaceutical compositions described in WO2006/036981 and U.S. application Ser. No. 11/238,285 (published as US20060116365), which are incorporated herein by reference in their entireties.

The foregoing cited documents are merely exemplary of small molecule HGF agonists and mimetics and the invention is in no means limited thereto, but embraces small molecule HGF mimetics and agonists generally. The invention is generally directed to the use of HGF mimics or HGF pathway activators for prophylaxis or treatment of scleroderma and related diseases.

In one embodiment, compounds useful for the purposes described herein are substituted pyrazoles having the structure:

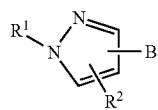

(I)

wherein $R^1$, $R^2$ and B are as described generally and in classes and subclasses herein.

In certain embodiments, the present invention embraces the use of compounds of general formula ($II^{A1}$) and ($III^{D1}$),

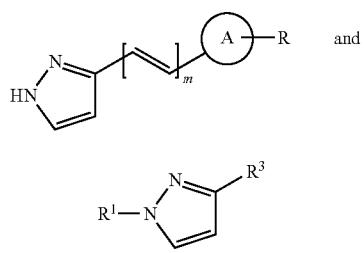

($II^{A1}$) and ($III^{D1}$)

tautomers thereof, C(5)-positional isomers thereof; and pharmaceutical compositions thereof, as described generally and in subclasses herein, which compounds are useful for the purposes described herein.

In another embodiment, the invention is directed to a method for the use for any of the purposes described herein of compounds or pharmaceutical compositions comprising compounds with the general formula (IV):

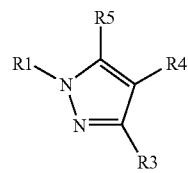

(IV)

wherein R3 and R5 are independently or together a straight-chain or branched $C_1$-$C_6$ alkyl optionally substituted with a cyano or halogen, halogen, trifluoromethyl or difluoromethyl groups; R1 is hydrogen, methyl, CO-Aryl, $SO_2$-Aryl, CO-heteroaryl, or CO-alkyl; and R4 is $CH_2$-Aryl, halogen, arylcarbonylvinyl or S-heteroaryl.

In another embodiment, the invention is directed to methods for the use for the purposes described herein of compounds or pharmaceutical compositions comprising compounds with the general formula (V):

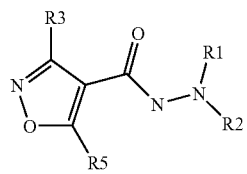

(V)

wherein R5 is a $C_1$ to $C_6$ branched or straight-chained alkyl group; R3 is a substituted or unsubstituted Aryl group; R1 is hydrogen or a $C_1$ to $C_4$ straight-chained, branched or cycloalkyl group; R2 is $COCH_2ONCH$-Aryl; heteroaryl, $COCH_2CH_2$Aryl; Aryl; COS-Aryl; CO-Heteroaryl; $C_1$ to $C_4$ straight-chained alkyl, branched alkyl, or cycloalkyl; or wherein R1 and R2 form a cyclic group of 5 or 6 carbon atoms.

In a further embodiment, the invention is directed to methods for the use for any of the purposes described herein of compounds or pharmaceutical compositions comprising compounds with the general formula (VI):

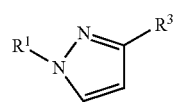

(VI)

wherein $R^1$ is $SO_2$Alkyl, $SO_2$-Aryl, CO-t-Butyl, COAryl, CONHAlkyl; CONHAryl; and $R^3$ is CHCH-heteroaryl; phenoxyphenyl; heteroaryl; or aryl substituted heteroaryl.

In a further embodiment, the invention is directed to methods for the use for any of the purposes described herein of compounds or pharmaceutical compositions comprising compounds with the general formula VII:

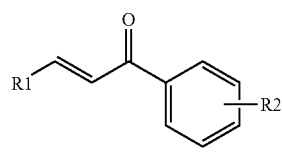

(VII)

Wherein R1 is Aryl or Heteroaryl; and R2 is one or more halogen, nitro, $C_1$ to $C_4$ straight-chained alkyl, branched alkyl, or cycloalkyl, or $C_1$ to $C_4$ alkyloxy groups.

In yet a further embodiment, the invention is also directed to methods for use of any of the purposes described herein compounds or pharmaceutical compositions comprising compounds with the general formulae VIII and $IX^A$:

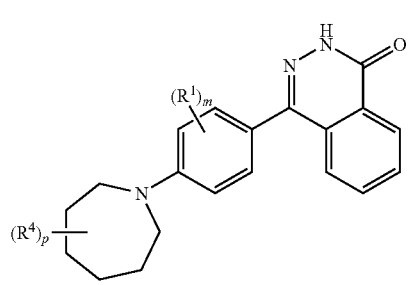

(VIII)

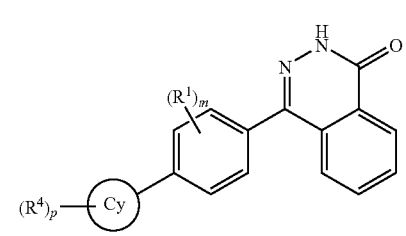

($IX^A$)

wherein the substituents depicted therein are described in detail below.

BRIEF DESCRIPTIONS OF THE FIGURES

Figure 2:
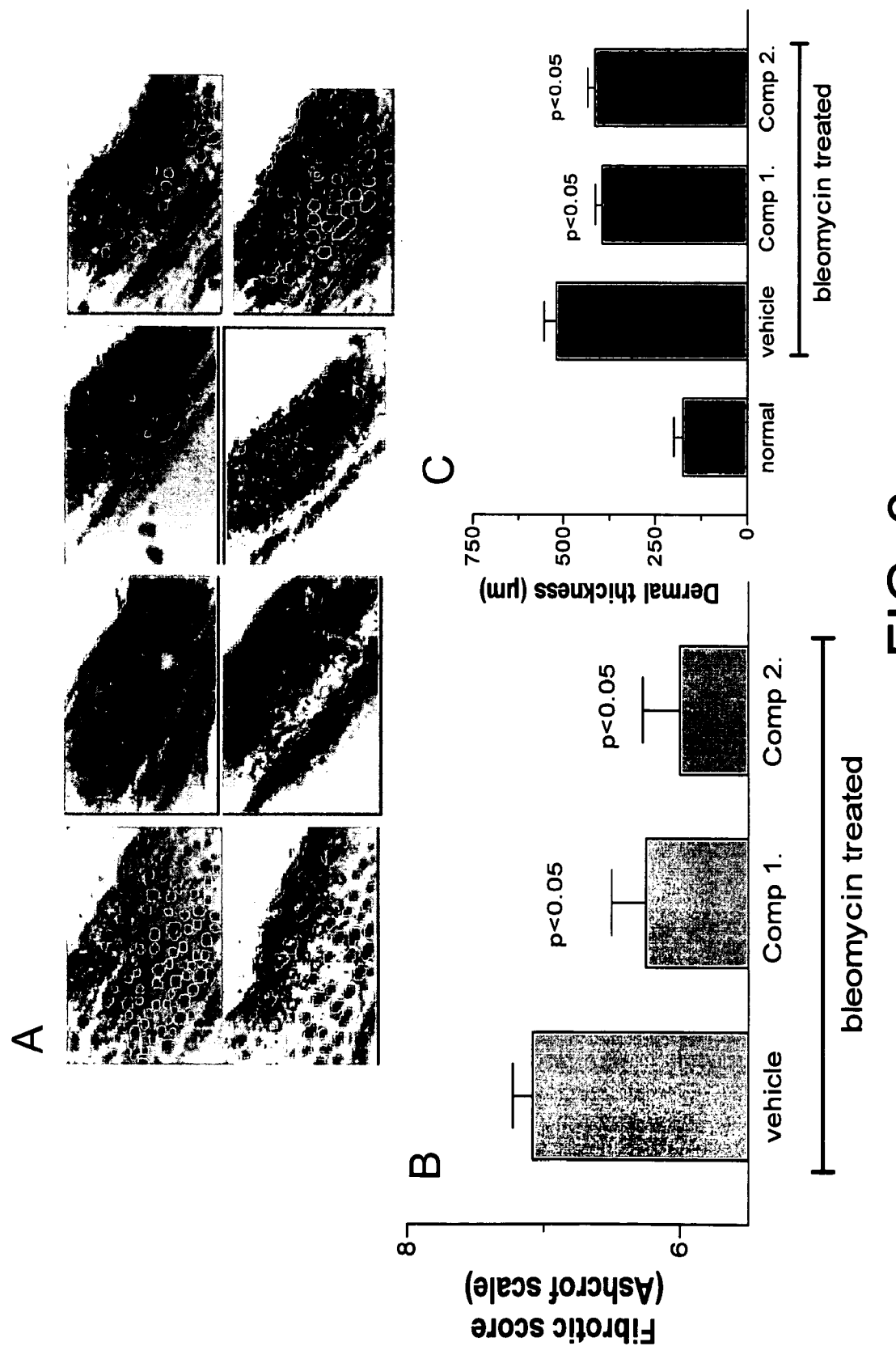
Figure 3:
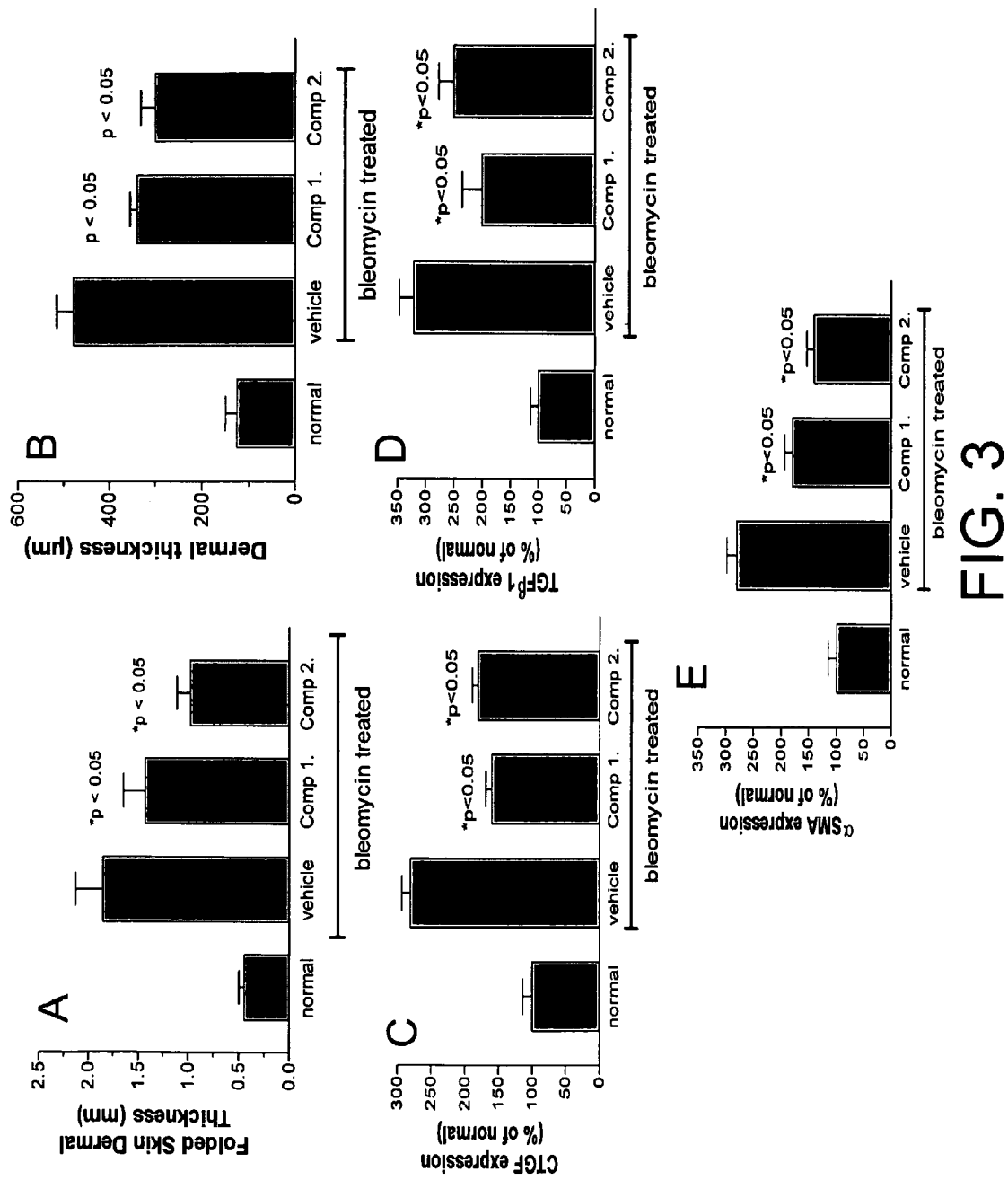
Figure 4:
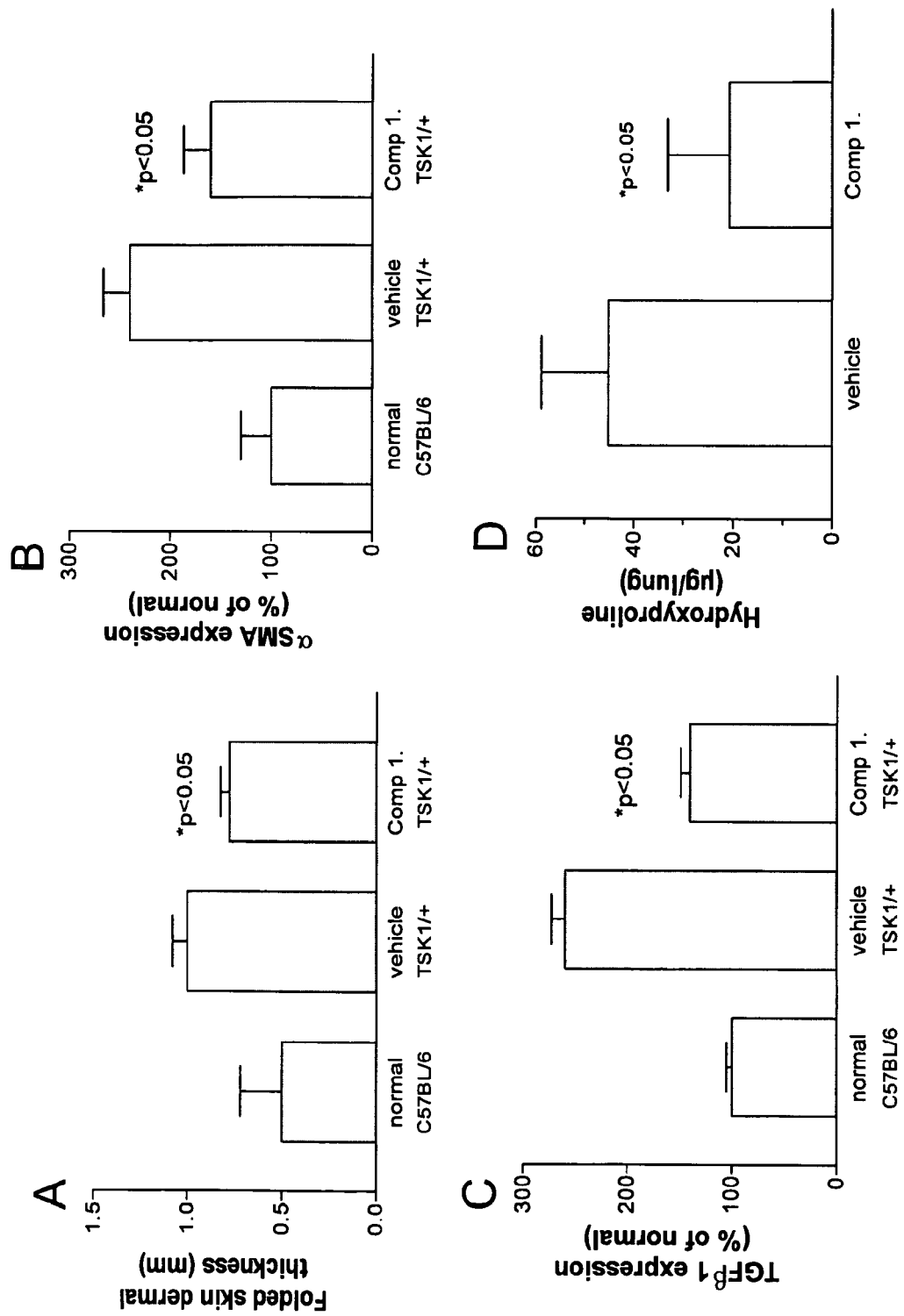
Figure 5:
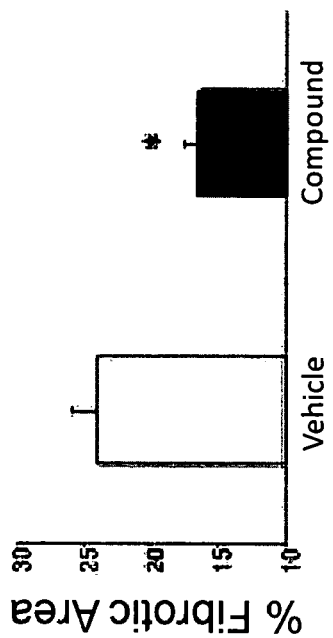
Figure 6:
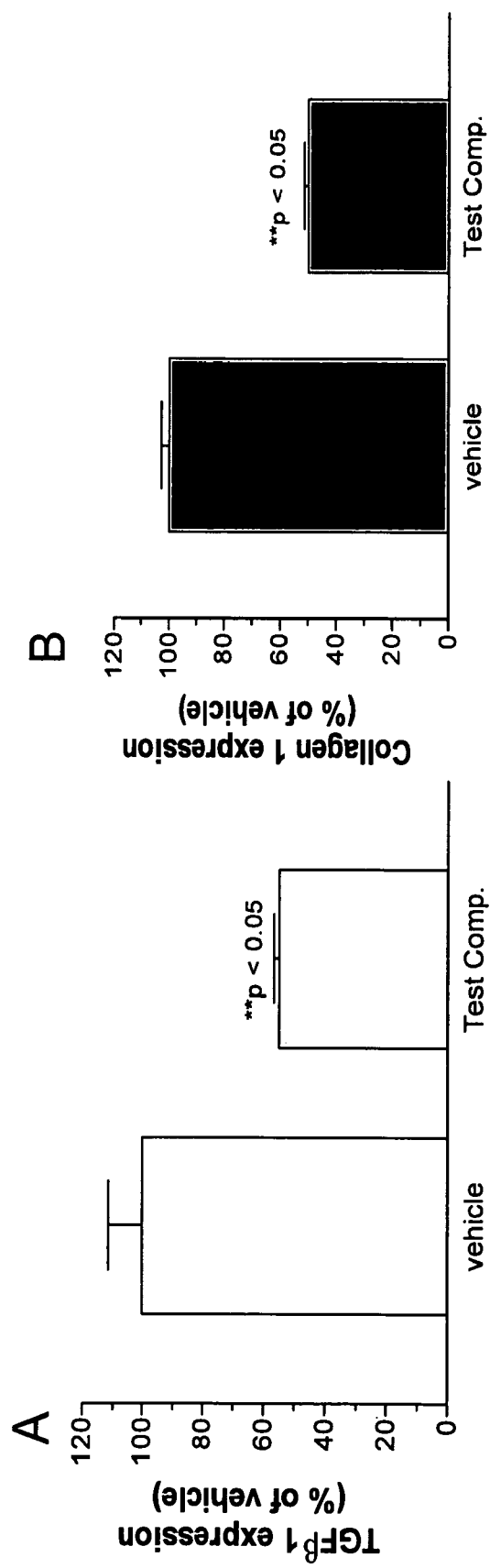

FIG. 1A-D show the results of a prevention study using a compound of the invention on dermal thickness, fibrotic score, total- and phospho-c-Met level in skin in the bleomycin model of scleroderma;

FIG. 2A-C show the results of a prevention study using compounds of the invention on histology, fibrotic score and dermal thickness of skin in the bleomycin model of scleroderma;

FIG. 3A-E show the results of an intervention study using compounds of the invention on folded skin dermal thickness, dermal thickness, CTGF expression, TGF-beta expression, and alpha-SMA expression levels in skin in the bleomycin model of scleroderma;

FIG. 4A-D show the results of a study using a compound of the invention on folded skin dermal thickness, alpha-SMA expression, TGF-beta expression and lung hydroxyproline in the TSK model of scleroderma;

FIG. 5 shows the results of a study using a compound of the invention on fibrotic score in the TSK model of scleroderma; and FIG. 6A-B show the results of an in vitro study on TGF-beta and collagen 1 expression in fibroblasts from scleroderma patients using a compound of the invention.

DEFINITIONS

The term "aliphatic", as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, or alkynyl moieties.

Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having 1-6 carbon atoms. "Lower alkenyl" and "lower alkynyl" respectively include corresponding 1-6 carbon moieties.

In certain embodiments, the alkyl, alkenyl and alkynyl groups employed in the invention contain 1-20; 2-20; 3-20; 4-20; 5-20; 6-20; 7-20 or 8-20 aliphatic carbon atoms. In certain other embodiments, the alkyl, alkenyl, and alkynyl groups employed in the invention contain 1-10; 2-10; 3-10; 4-10; 5-10; 6-10; 7-10 or 8-10 aliphatic carbon atoms. In yet other embodiments, the alkyl, alkenyl, and alkynyl groups employed in the invention contain 1-8; 2-8; 3-8; 4-8; 5-8; 6-20 or 7-8 aliphatic carbon atoms. In still other embodiments, the alkyl, alkenyl, and alkynyl groups employed in the invention contain 1-6; 2-6; 3-6; 4-6 or 5-6 aliphatic carbon atoms. In yet other embodiments, the alkyl, alkenyl, and alkynyl groups employed in the invention contain 1-4; 2-4 or 3-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds that combine the properties of aliphatic and cyclic compounds and include but are not limited to monocyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —CH$_2$-cyclopropyl, cyclobutyl, —CH$_2$-cyclobutyl, cyclopentyl, —CH$_2$-cyclopentyl, cyclohexyl, —CH$_2$-cyclohexyl, cyclohexenylethyl, cyclohexanylethyl, norborbyl moieties and the like, which again, may bear one or more substituents.

The term "alkoxy" or "alkyloxy", as used herein refers to a saturated (i.e., O-alkyl) or unsaturated (i.e., O-alkenyl and O-alkynyl) group attached to the parent molecular moiety through an oxygen atom. In certain embodiments, the alkyl group contains 1-20; 2-20; 3-20; 4-20; 5-20; 6-20; 7-20 or 8-20 aliphatic carbon atoms. In certain other embodiments, the alkyl group contains 1-10; 2-10; 3-10; 4-10; 5-10; 6-10; 7-10 or 8-10 aliphatic carbon atoms. In yet other embodiments, the alkyl, alkenyl, and alkynyl groups employed in the invention contain 1-8; 2-8; 3-8; 4-8; 5-8; 6-20 or 7-8 aliphatic carbon atoms. In still other embodiments, the alkyl group contains 1-6; 2-6; 3-6; 4-6 or 5-6 aliphatic carbon atoms. In yet other embodiments, the alkyl group contains 1-4; 2-4 or 3-4 aliphatic carbon atoms. Examples of alkoxy, include but are not limited to, methoxy, ethoxy, propoxy, isopropoxy, n-butoxy, i-butoxy, sec-butoxy, tert-butoxy, neopentoxy, n-hexoxy and the like.

The term "thioalkyl" as used herein refers to a saturated (i.e., S-alkyl) or unsaturated (i.e., S-alkenyl and S-alkynyl) group attached to the parent molecular moiety through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of thioalkyl include, but are not limited to, methylthio, ethylthio, propylthio, isopropylthio, n-butylthio, and the like.

The term "alkylamino" refers to a group having the structure —NHR' wherein R' is aliphatic or alicyclic, as defined herein. The term "aminoalkyl" refers to a group having the structure NH$_2$R'—, wherein R' is aliphatic or alicyclic, as defined herein. In certain embodiments, the aliphatic or alicyclic group contains 1-20 aliphatic carbon atoms. In certain other embodiments, the aliphatic or alicyclic group contains 1-10 aliphatic carbon atoms. In still other embodiments, the aliphatic or alicyclic group contains 1-6 aliphatic carbon atoms. In yet other embodiments, the aliphatic or alicyclic group contains 1-4 aliphatic carbon atoms. In yet other embodiments, R' is an alkyl, alkenyl, or alkynyl group containing 1-8 aliphatic carbon atoms. Examples of alkylamino include, but are not limited to, methylamino, ethylamino, iso-propylamino and the like.

Some examples of substituents of the above-described aliphatic (and other) moieties of compounds of the invention include, but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(=O)R$_x$; —CO$_2$(R$_x$); —C(=O)N(R$_x$)$_2$; —OC(=O)R$_x$; —OCO$_2$R$_x$; —OC(=O)N(R$_x$)$_2$; —N(R$_x$)$_2$; —OR$_x$; —SR$_x$; —S(O)R$_x$; —S(O)$_2$R$_x$; —NR$_x$(CO)R$_x$; —N(R$_x$)CO$_2$R$_x$; —N(R$_x$)S(O)$_2$R$_x$; —N(R$_x$)C(=O)N(R$_x$)$_2$; —S(O)$_2$N(R$_x$)$_2$; wherein each occurrence of R$_x$ independently includes, but is not limited to, aliphatic, alicyclic, heteroaliphatic, heterocyclic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aryl or heteroaryl substituents described above and herein may be substituted or unsubstituted. Additional examples of generally applicable substituents are illustrated by the specific embodiments shown in the Examples that are described herein.

In general, the term "aromatic moiety", as used herein, refers to a stable mono- or polycyclic, unsaturated moiety having preferably 3-14 carbon atoms, each of which may be substituted or unsubstituted. In certain embodiments, the term "aromatic moiety" refers to a planar ring having p-orbitals perpendicular to the plane of the ring at each ring atom and satisfying the Huckel rule where the number of pi electrons in the ring is (4n+2) wherein n is an integer. A mono- or polycyclic, unsaturated moiety that does not satisfy one or all of these criteria for aromaticity is defined herein as "non-aromatic", and is encompassed by the term "alicyclic".

In general, the term "heteroaromatic moiety", as used herein, refers to a stable mono- or polycyclic, unsaturated moiety having preferably 3-14 carbon atoms, each of which may be substituted or unsubstituted; and comprising at least one heteroatom selected from O, S and N within the ring (i.e., in place of a ring carbon atom). In certain embodiments, the term "heteroaromatic moiety" refers to a planar ring comprising at least one heteroatom, having p-orbitals perpendicular to the plane of the ring at each ring atom, and satisfying the Huckel rule where the number of pi electrons in the ring is (4n+2) wherein n is an integer.

It will also be appreciated that aromatic and heteroaromatic moieties, as defined herein may be attached via an alkyl or heteroalkyl moiety and thus also include -(alkyl)aromatic, -heteroalkyl)aromatic, -(heteroalkyl)heteroaromatic, and -(heteroalkyl)heteroaromatic moieties. Thus, as used herein, the phrases "aromatic or heteroaromatic moieties" and "aromatic, heteroaromatic, -(alkyl)aromatic, -(heteroalkyl)aromatic, -(heteroalkyl)heteroaromatic, and -(heteroalkyl)heteroaromatic" are interchangeable. Substituents include, but are not limited to, any of the previously mentioned substituents, i.e., the substituents recited for aliphatic moieties, or for other moieties as disclosed herein, resulting in the formation of a stable compound.

The term "aryl", as used herein, does not differ significantly from the common meaning of the term in the art, and refers to an unsaturated cyclic moiety comprising at least one aromatic ring. In certain embodiments, "aryl" refers to a mono- or bicyclic carbocyclic ring system having one or two aromatic rings including, but not limited to, phenyl, naphthyl, tetrahydronaphthyl, indanyl, indenyl and the like.

The term "heteroaryl", as used herein, does not differ significantly from the common meaning of the term in the art, and refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, quinolinyl, isoquinolinyl, and the like.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroallcylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(=O)R$_x$; —CO$_2$(R$_x$); —C(=O)N(R$_x$)$_2$; —OC(=O)R$_x$; —OCO$_2$R$_x$; —OC(=O)N(R$_x$)$_2$; —N(R$_x$)$_2$; —OR$_x$; —SR$_x$; —S(O)R$_x$; —S(O)$_2$R$_x$; —NR$_x$(CO)R$_x$; —N(R$_x$)CO$_2$R$_x$; —N(R$_x$)S(O)$_2$R$_x$; —N(R$_x$)C(=O)N(R$_x$)$_2$; —S(O)$_2$N(R$_x$)$_2$; wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments shown in the Examples that are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, alicyclic, heteroaliphatic or heterocyclic moieties, may optionally be substituted with substituents including, but not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(=O)R$_x$; —CO$_2$(R$_x$); —C(=O)N(R$_x$)$_2$; —OC(=O)R$_x$; —OCO$_2$R$_x$; —OC(=O)N(R$_x$)$_2$; —N(R$_x$)$_2$; —OR$_x$; —SR$_x$; —S(O)R$_x$; —S(O)$_2$R$_x$; —NR$_x$(CO)R$_x$; —N(R$_x$)CO$_2$R$_x$; —N(R$_x$)S(O)$_2$R$_x$; —N(R$_x$)C(=O)N(R$_x$)$_2$; —S(O)$_2$N(R$_x$)$_2$; wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be linear or branched, and saturated or unsaturated. In certain embodiments, heteroaliphatic moieties are substituted by independent replacement of one or more of the hydrogen atoms thereon with one or more moieties including, but not limited to aliphatic; alicyclic; heteroaliphatic; heterocyclic; aromatic; heteroaromatic; aryl; heteroaryl; alkylaryl; alkyiheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$SO$_2$CH$_3$; —C(=O)R$_x$; —CO$_2$(R$_x$); —C(=O)N(R$_x$)$_2$; —OC(=O)R$_x$; —OCO$_2$R$_x$; —OC(=O)N(R$_x$)$_2$; —N(R$_x$)$_2$; —OR$_x$; —SR$_x$; —S(O)R$_x$; —S(O)$_2$R$_x$; —NR$_x$(CO)R$_x$; —N(R$_x$)CO$_2$R$_x$; —N(R$_x$)S(O)$_2$R$_x$; —N(R$_x$)C(=O)N(R$_x$)$_2$; —S(O)$_2$N(R$_x$)$_2$; wherein each occurrence of R$_x$ independently includes, but is not limited to, aliphatic, alicyclic, heteroaliphatic, heterocyclic, aromatic, heteroaromatic, aryl, heteroaryl, alkylaryl, allcylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

The term "heterocycloalkyl", "heterocycle" or "heterocyclic", as used herein, refers to compounds which combine the properties of heteroaliphatic and cyclic compounds and include, but are not limited to, saturated and unsaturated mono- or polycyclic cyclic ring systems having 5-16 atoms wherein at least one ring atom is a heteroatom selected from O, S and N (wherein the nitrogen and sulfur heteroatoms may be optionally be oxidized), wherein the ring systems are optionally substituted with one or more functional groups, as defined herein. In certain embodiments, the term "heterocycloalkyl", "heterocycle" or "heterocyclic" refers to a non-aromatic 5-, 6- or 7-membered ring or a polycyclic group wherein at least one ring atom is a heteroatom selected from O, S and N (wherein the nitrogen and sulfur heteroatoms may be optionally be oxidized), including, but not limited to, a bi- or tri-cyclic group, comprising fused six-membered rings having between one and three heteroatoms independently selected from oxygen, sulfur and nitrogen, wherein (i) each 5-membered ring has 0 to 2 double bonds, each 6-membered ring has 0 to 2 double bonds and each 7-membered ring has 0 to 3 double bonds, (ii) the nitrogen and sulfur heteroatoms may be optionally be oxidized, (iii) the nitrogen heteroatom may optionally be quaternized, and (iv) any of the above heterocyclic rings may be fused to an aryl or heteroaryl ring. Representative heterocycles include, but are not limited to, heterocycles such as furanyl, thiofuranyl, pyranyl, pyrrolyl, pyrazolyl, imidazolyl, thienyl, pyrrolidinyl, pyrazolinyl, pyrazolidinyl, imidazolinyl, imidazolidinyl, piperidinyl, piperazinyl, oxazolyl, oxazolidinyl, isooxazolyl, isoxazolidinyl, dioxazolyl, thiadiazolyl, oxadiazolyl, tetrazolyl, triazolyl, thiatriazolyl, oxatriazolyl, thiadiazolyl, oxadiazolyl, morpholinyl, thiazolyl, thiazolidinyl, isothiazolyl, isothiazolidinyl, dithiazolyl, dithiazolidinyl, tetrahydrofuryl, and benzo-fused derivatives thereof. In certain embodiments, a "substituted heterocycle, or heterocycloalkyl or heterocyclic" group is utilized and as used herein, refers to a heterocycle, or heterocycloalkyl or heterocyclic group, as defined above, substituted by the independent replacement of one, two or three of the hydrogen atoms thereon with but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(=O)R$_x$; —CO$_2$(R$_x$); —C(=O)N(R$_x$)$_2$; —OC(=O)R$_x$; —OCO$_2$R$_x$; —OC(=O)N(R$_x$)$_2$; —N(R$_x$)$_2$; —OR$_x$; —SR$_x$; —S(O)R$_x$; —S(O)$_2$R$_x$; —NR$_x$(CO)R$_x$; —N(R$_x$)CO$_2$R$_x$; —N(R$_x$)S(O)$_2$R$_x$; —N(R$_x$)C(=O)N(R$_x$)$_2$; —S(O)$_2$N(R$_x$)$_2$; wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples or generally applicable substituents are illustrated by the specific embodiments shown in the Examples, which are described herein.

Additionally, it will be appreciated that any of the alicyclic or heterocyclic moieties described above and herein may comprise an aryl or heteroaryl moiety fused thereto. Additional examples of generally applicable substituents are illustrated by the specific embodiments shown in the Examples that are described herein.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "amino", as used herein, refers to a primary (—NH$_2$), secondary (—NHR$_x$), tertiary (—NR$_x$R$_y$) or quaternary (—N$^+$R$_x$R$_y$R$_z$) amine, where R$_x$, R$_y$ and R$_z$ are independently an aliphatic, alicyclic, heteroaliphatic, heterocyclic, aromatic or heteroaromatic moiety, as defined herein. Examples of amino groups include, but are not limited to, methylamino, dimethylamino, ethylamino, diethylamino, diethylaminocarbonyl, methylethylamino, iso-propylamino, piperidino, trimethylamino, and propylamino.

The term "acyl", as used herein, refers to a group having the general formula —C(=O)R, where R is an aliphatic, alicyclic, heteroaliphatic, heterocyclic, aromatic or heteroaromatic moiety, as defined herein.

The term "C$_{2-6}$alkenylidene", as used herein, refers to a substituted or unsubstituted, linear or branched unsaturated divalent radical consisting solely of carbon and hydrogen atoms, having from two to six carbon atoms, having a free valence "-" at both ends of the radical, and wherein the unsaturation is present only as double bonds and wherein a double bond can exist between the first carbon of the chain and the rest of the molecule.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms "alicyclic", "heterocyclic", "heterocycloalkyl", "heterocycle" and the like encompass substituted and unsubstituted, and saturated and unsaturated groups. Additionally, the terms "cycloalkyl", "cycloalkenyl", "cycloalkynyl", "heterocycloalkyl", "heterocyclealkenyl", "heterocycloalkynyl", "aromatic", "heteroaromatic", "aryl", "heteroaryl" and the like encompass both substituted and unsubstituted groups.

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety, which is susceptible to removal in vivo yielding the parent molecule as the pharmacologically active species. An example of a pro-drug is an ester, which is cleaved in vivo to yield a compound of interest. Another example is an N-methyl derivative of a compound, which is susceptible to oxidative metabolism resulting in N-demethylation, particularly on the 1 position of the 3(5)-monosubstituted pyrazole derivatives of the invention. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

The term "tautomerization" refers to the phenomenon wherein a proton of one atom of a molecule shifts to another atom. See, Jerry March, Advanced Organic Chemistry: Reactions, Mechanisms and Structures, Fourth Edition, John Wiley & Sons, pages 69-74 (1992). The term "tautomer" as used herein, refers to the compounds produced by the proton shift. For example, compounds of formula II (and more generally, compounds of formula I where $R^1$ is hydrogen), can exist as a tautomer as shown below:

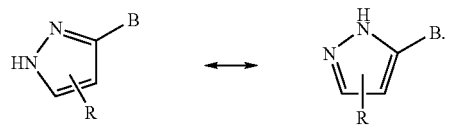

Thus, the present invention encompasses the 3-monosubstituted pyrazole compounds described herein (e.g., compounds of formula I, II, and related formulae $II^A$, $II^B$, $II^C$, etc . . . ), as well as their tautomeric 5-monosubstituted pyrazole counterparts. Likewise, any compound shown as 5-monosubstituted pyrazole embraces its corresponding 3-monosubstituted tautomer. The term "C(5)-positional isomer" as used herein refers to 1,5-disubstituted counterparts of the 1,3-disubstituted pyrazole compounds described herein. For example, the invention encompasses compounds of the formula ($X^B$) and its C(5)-positional isomer ($X^{B'}$):

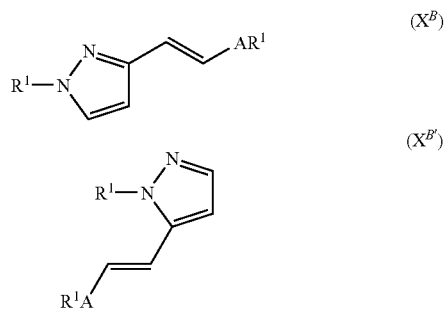

Thus, whether or not explicitly specified, the present invention encompasses the 1,3-disubstituted pyrazole compounds described herein (e.g., compounds of formula I, II, III, IV, VI, and related formulae $III^A$, $III^B$, $III^C$, $III^D$, etc . . . ), as well as their C(5)-positional pyrazole counterparts. Likewise, any compound shown as 1,5-disubstituted pyrazole embraces its corresponding 1,3-disubstituted positional isomer.

By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, as detailed herein, certain exemplary oxygen protecting groups are utilized. These oxygen protecting groups include, but are not limited to methyl ethers, substituted methyl ethers (e.g., MOM (methoxymethyl ether), MTM (methylthiomethyl ether), BOM (benzyloxymethyl ether), PMBM or MPM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. In certain other exemplary embodiments, nitrogen-protecting groups are utilized. These nitrogen protecting groups include, but are not limited to, carbamates (including methyl, ethyl and substituted ethyl carbamates (e.g., Troc), to name a few) amides, cyclic imide derivatives, N-Alkyl and N-Aryl amines, imine derivatives, and enamine derivatives, to name a few. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

DETAILED DESCRIPTION OF CERTAIN PREFERRED EMBODIMENTS OF THE INVENTION

The present invention is directed generally to the treatment and prevention of fibrotic connective diseases including scleroderma and systemic sclerosis. It is also directed to surgically-induced fibrotic conditions including intra-abdominal adhesions and other adhesions. Small molecule agents that activate signaling pathways of hepatocyte growth factor (also known as scatter factor; abbreviated HGF or HGF/SF) have been found to be useful in various therapeutic modalities including prophylaxis and treatment of the aforementioned pathologies. Compounds of this invention include those generally set forth above and described specifically herein, and are illustrated in part by the various classes, subgenera and species disclosed herein.

Additionally, the present invention provides pharmaceutically acceptable derivatives of the inventive compounds, and methods of treating a subject using these compounds, pharmaceutical compositions thereof, or either of these in combination with one or more additional therapeutic agents. Exemplary small molecule activators of HGF pathways are described in WO2004/058721; WO02/002593 and U.S. Pat. No. 6,589,997; and U.S. patent application Ser. No. 11/238,285 and WO application PCT/US2005/034669 (published as WO2006/036981), all of which are incorporated herein by reference in their entireties. These are described in more detail below.

In certain embodiments, the uses described herein extend to compounds of the general formula (I) as further defined below:

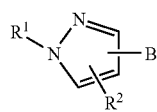
(I)

and tautomers and C(5)-positional isomers thereof;
wherein B is a C(3)- or C(5)-substituent selected from the group consisting of -AL$^1$-A, aryl, heteroaryl and heterocyclic; wherein AL$^1$ is an optionally substituted C$_{2-6}$alkenylidene moiety, and A is an optionally substituted alicyclic, heteroalicyclic, aromatic or heteroaromatic moiety;

R$^1$ is hydrogen, —C(=O)(CH$_2$)$_m$R$^{1A}$, —C(=O)OR$^{1A}$, —C(=O)N(R$^{1A}$)$_2$ or —SO$_2$R$^{1A}$; wherein m is an integer from 0-3; each occurrence of R$^{1A}$ is independently hydrogen or an optionally substituted aliphatic, alicyclic, heteroaliphatic, heteroalicyclic, aromatic or heteroaromatic moiety; and R$^2$ is one or more substituents selected from the group consisting of hydrogen, halogen, hydroxyl, —NO$_2$, —CN, an optionally substituted aliphatic, heteroaliphatic, aromatic, heteroaromatic moiety; —OR$^R$, —S(=O)$_n$R$^d$, —NR$^b$R$^c$, and —C(=O)R$^a$; wherein n is 0-2, R$^R$ is an optionally substituted aliphatic, heteroaliphatic, aromatic or heteroaromatic moiety;

R$^a$, for each occurrence, is independently selected from the group consisting of hydrogen, hydroxy, aliphatic, heteroaliphatic, aryl and heteroaryl;

R$^b$ and R$^c$, for each occurrence, are independently selected from the group consisting of hydrogen; hydroxy; SO$_2$R$^d$; aliphatic, heteroaliphatic, aryl and heteroaryl;

R$^d$, for each occurrence, is independently selected from the group consisting of hydrogen; —N(R$^e$)$_2$; aliphatic, aryl and heteroaryl; and R$^e$, for each occurrence, is independently hydrogen or aliphatic.

In certain embodiments, the present invention defines uses of particular classes of compounds which are of special interest. For example, one class of compounds of special interest includes those compounds of formula (I) wherein the nitrogen atom at position 1 is unsubstituted and the compound has the structure (II):

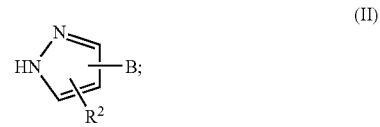
(II)

and tautomers thereof;
wherein R$^2$ and B are as defined generally above and in classes and subclasses herein.

Another class of compounds of special interest includes those compounds of formula (II) having the structure (II$^A$):

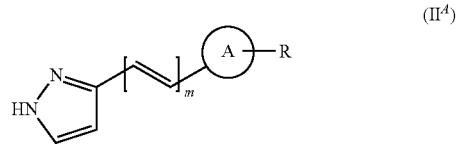
(II$^A$)

and tautomers thereof;
wherein A is as defined generally above and in classes and subclasses herein; m is an integer from 0-3; and R is one or two substituents selected from the group consisting of hydrogen, halogen, hydroxyl, —NO$_2$, —CN, an optionally substituted aliphatic, heteroaliphatic, aromatic, heteroaromatic moiety; —OR$^R$, —S(=O)$_n$R$^d$, —NR$^b$R$^c$, and —C(=O)R$^a$; wherein n is 0-2, R$^R$ is an optionally substituted aliphatic, heteroaliphatic, aromatic or heteroaromatic moiety;

R$^a$, for each occurrence, is independently selected from the group consisting of hydrogen, hydroxy, aliphatic, heteroaliphatic, aryl and heteroaryl;

R$^b$ and R$^c$, for each occurrence, are independently selected from the group consisting of hydrogen; hydroxy; SO$_2$R$^d$; aliphatic, heteroaliphatic, aryl and heteroaryl;

R$^d$, for each occurrence, is independently selected from the group consisting of hydrogen; —N(R$^e$)$_2$; aliphatic, aryl and heteroaryl; and R$^e$, for each occurrence, is independently hydrogen or aliphatic.

Another class of compounds of special interest includes those compounds of formula (II) having the structure (II$^B$):

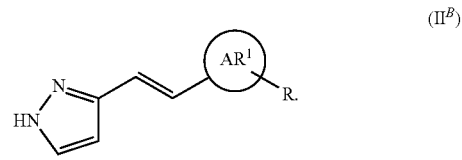
(II$^B$)

and tautomers thereof;
wherein R is as defined generally above and in classes and subclasses herein; and AR$^1$ is an optionally substituted aryl moiety.

Another class of compounds of special interest includes those compounds of formula (II) having the structure (II$^C$):

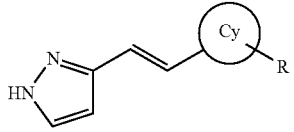

(II$^C$)

and tautomers thereof;
wherein R is as defined generally above and in classes and subclasses herein; and Cy is an optionally substituted heterocyclic moiety.

Another class of compounds of special interest includes those compounds of formula (I) wherein the nitrogen atom at position bears a substituent R' and the compound has the structure (III):

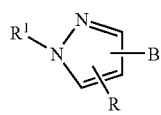

(III)

and C(5)-positional isomers thereof;
wherein B is as defined generally above and in classes and subclasses herein; and R is —C(=O)(CH$_2$)$_m$R$^{1A}$, —C(=O)OR$^{1A}$, —C(=O)N(R$^{1A}$)$_2$ or —SO$_2$R$^{1A}$; wherein m is an integer from 0-3; and each occurrence of R$^{1A}$ is independently hydrogen or an optionally substituted aliphatic, alicyclic, heteroaliphatic, heteroalicyclic, aromatic or heteroaromatic moiety.

Another class of compounds of special interest includes those compounds of formula (III) having the structure (III$^A$):

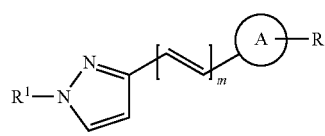

(III$^A$)

and C(5)-positional isomers thereof;
wherein R$^1$, R and A are as defined generally above and in classes and subclasses herein; and m is an integer from 0-3.

Another class of compounds of special interest includes those compounds of formula (III) having the structure (III$^B$):

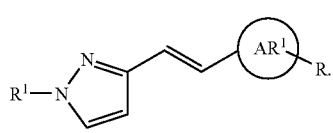

(III$^B$)

and C(5)-positional isomer thereof;
wherein R and R$^1$ are as defined generally above and in classes and subclasses herein; and AR$^1$ is an optionally substituted aryl moiety.

Another class of compounds of special interest includes those compounds of formula (III) having the structure (III$^C$):

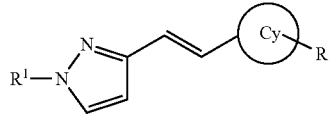

(III$^C$)

and C(5)-positional isomers thereof;
wherein R and R$^1$ are as defined generally above and in classes and subclasses herein; and Cy is an optionally substituted heterocyclic moiety.

Another class of compounds of special interest includes those compounds of formula (III) having the structure (III$^D$):

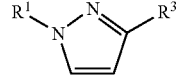

(III$^D$)

and C(5)-positional isomers thereof;
wherein R$^1$ is —SO$_2$R$^{1A}$; —C(=O)(CH$_2$)$_m$R$^{1A}$, —C(=O)OR$^{1A}$ or —C(=O)NHR$^{1A}$, wherein m is an integer from 0-3; and each occurrence of R$^{1A}$ is independently an optionally substituted aliphatic, alicyclic, heteroaliphatic, aryl or heterocyclic moiety; and
R$^3$ is a cis or trans —CH=CH-AR$^1$, —CH=CH-Cy, phenoxyphenyl, or a heterocyclic group; wherein AR$^1$ is an optionally substituted aryl moiety and Cy is an optionally substituted heterocyclic moiety.

A number of important subclasses of each of the foregoing classes deserve separate mention; these subclasses include subclasses of the foregoing classes in which:
i) R$^1$ is hydrogen;
ii) is —C(=O)R$^{1A}$, —C(=O)NHR$^{1A}$ or —SO$_2$R$^{1A}$; wherein each occurrence of R$^{1A}$ is independently alkyl, alkenyl, alkynyl, cycloalkyl, cycloalkenyl, cycloalkynyl, heterocyclic, aryl, heteroaryl, -(alkyl)aryl, -(heteroalkyl)aryl, -(alkyl)heteroaryl or -(heteroalkyl)heteroaryl moiety;
iii) R$^1$ is —C(=O)R$^{1A}$, —C(=O)NHR$^{1A}$ or —SO$_2$R$^{1A}$; wherein each occurrence of R$^{1A}$ is independently an alkyl, cycloalkyl, heterocyclic or aryl moiety;
iv) R$^1$ is —SO$_2$R$^{1A}$, —C(=O)(CH$_2$)$_m$R$^{1A}$, —C(=O)OR$^{1A}$ or —C(=O)NHR$^{1A}$, wherein m is an integer from 0-3; and each occurrence of R$^{1A}$ is independently alkyl, alkenyl, alkynyl, cycloalkyl, cycloalkenyl, cycloalkynyl, heterocyclic, aryl, heteroaryl, -(alkyl)aryl, -(heteroalkyl)aryl, -(alkyl)heteroaryl or -(heteroalkyl)heteroaryl moiety;
v) R$^1$ is —SO$_2$R$^{1A}$, —C(=O)(CH$_2$)$_m$R$^{1A}$, —C(=O)OR$^{1A}$ or —C(=O)NHR$^{1A}$, wherein m is an integer from 0-3; and each occurrence of R$^{1A}$ is independently an alkyl, cycloalkyl, heterocyclic or aryl moiety;
vi) R$^1$ is SO$_2$AL$^1$, C(=O)(CH$_2$)$_m$AL$^1$, C(=O)OAL$^1$, C(=O)NHAL$^1$, SO$_2$Aryl, C(=O)(CH$_2$)$_m$Aryl, C(=O)OAryl, C(=O)OHeterocyclic, C(=O)(CH$_2$)$_m$Heterocyclic, or C(=O)NHAryl; wherein m is 0-3; AL$^1$ is an aliphatic or alicyclic moiety; and AL$^1$, the aryl and heterocyclic moiety are independently optionally substituted with one or more substituents independently selected from the group consisting of hydrogen; halogen; hydroxy; nitro; CN; aryl; heteroaryl; —C(=O)$R^a$, —$NR^bR^c$, or —S(O)$_n R^d$ where n=0-2; $C_{1-6}$alkoxy optionally substituted with one or more substituents independently selected from halogen and $C_{1-6}$ alkyl; an optionally substituted fused bicyclic 8-12-membered aromatic or alicyclic ring containing 0-3 heteroatoms selected from the group consisting of N, O, and S; $C_{1-6}$ alkyl, $C_{2-6}$ alkenyl, $C_{2-6}$ alkynyl, or $C_{3-6}$ cycloalkyl, optionally substituted with one or more substituents independently selected from halogen, hydroxy, $C_{1-5}$ alkoxy, nitro, and N($R^e$)$_2$; and further optionally substituted with 1-3 substituents independently selected from the group consisting of —C(=O)$R^a$, —$NR^bR^c$, —S(O)$_n R^d$ where n=0-2, hydroxy, $C_{1-6}$ alkoxy, halo$C_{1-6}$ alkoxy, aryl, heteroaryl and heterocyclyl; or COCH$_2$OC$_2$H$_5$OCH$_3$;

vii) compounds of subset vi) above wherein AL$^1$ is alkyl or cycloalkyl;

viii) $R^1$ is C(=O)(CH$_2$)$_m$AL$^1$; C(=O)(CH$_2$)$_m$Aryl or C(=O)Heterocyclic; wherein m-1-3; AL$^1$ is an aliphatic or alicyclic moiety; and AL$^1$, the aryl and heterocyclic moiety are independently optionally substituted with one or more substituents independently selected from hydrogen; halogen; hydroxy; nitro; CN; aryl; heteroaryl; —C(=O)$R^a$, —$NR^bR^c$, or —S(O)$_n R^d$ where n=0-2; $C_{1-6}$alkoxy optionally substituted with one or more substituents independently selected from halogen and $C_{1-6}$ alkyl; an optionally substituted fused bicyclic 8-12-membered aromatic or alicyclic ring containing 0-3 heteroatoms selected from the group consisting of N, O, and S; $C_{1-6}$ alkyl, $C_{2-6}$ alkenyl, $C_{2-6}$ alkynyl, or $C_{3-6}$ cycloalkyl, optionally substituted with one or more substituents independently selected from halogen, hydroxy, $C_{1-5}$ alkoxy, nitro, and N($R^e$)$_2$; and further optionally substituted with 1-3 substituents independently selected from the group consisting of —C(=O)$R^a$, —$NR^bR^c$, —S(O)$_n R^d$ where n=0-2, hydroxy, $C_{1-6}$ alkoxy, halo$C_{1-6}$ alkoxy, aryl, heteroaryl and heterocyclyl; or COCH$_2$OC$_2$H$_5$OCH$_3$;

ix) compounds of subset vii) above where AL$^1$ is alkyl or cycloalkyl;

x) $R^1$ is C(=O)O-AL$^1$ or C(=O)O-Aryl; wherein AL$^1$ is an aliphatic or alicyclic moiety; and AL$^1$ and the aryl moiety are optionally substituted with one or more substituents independently selected from hydrogen; halogen; hydroxy; nitro; CN; aryl; heteroaryl; —C(=O)$R^a$, —$NR^bR^c$, or —S(O)$_n R^d$ where n=0-2; $C_{1-6}$alkoxy optionally substituted with one or more substituents independently selected from halogen and $C_{1-6}$ alkyl; an optionally substituted fused bicyclic 8-12-membered aromatic or alicyclic ring containing 0-3 heteroatoms selected from the group consisting of N, O, and S; $C_{1-6}$ alkyl, $C_{2-6}$ alkenyl, $C_{2-6}$ alkynyl, or $C_{3-6}$ cycloalkyl, optionally substituted with one or more substituents independently selected from halogen, hydroxy, $C_{1-5}$ alkoxy, nitro, and N($R^e$)$_2$; and further optionally substituted with 1-3 substituents independently selected from the group consisting of —C(=O)$R^a$, —$NR^bR^c$, —S(O)$_n R^d$ where n=0-2, hydroxy, $C_{1-6}$ alkoxy, halo$C_{1-6}$ alkoxy, aryl, heteroaryl and heterocyclyl;

xi) compounds of subset x) above where AL$^1$ is alkyl or cycloalkyl;

xii) $R^1$ is SO$_2$AL$^1$, C(=O)(CH$_2$)$_m$AL$^1$, C(=O)NHAL$^1$, SO$_2$Aryl, C(=O)(CH$_2$)$_m$Aryl, C(=O)(CH$_2$)$_m$Heterocyclic or C(=O)NHAryl; wherein m is 0-3; AL$^1$ is an aliphatic or alicyclic moiety; and AL$^1$, the aryl and heterocyclic moiety are independently optionally substituted with one or more substituents independently selected from the group consisting of hydrogen; halogen; hydroxy; nitro; CN; aryl; heteroaryl; —C(=O)$R^a$, —$NR^bR^c$, or —S(O)$_n R^d$ where n=0-2; $C_{1-6}$alkoxy optionally substituted with one or more substituents independently selected from halogen and $C_{1-6}$ alkyl; an optionally substituted fused bicyclic 8-12-membered aromatic or alicyclic ring containing 0-3 heteroatoms selected from the group consisting of N, O, and S; $C_{1-6}$ alkyl, $C_{2-6}$ alkenyl, $C_{2-6}$ alkynyl, or $C_{3-6}$ cycloalkyl, optionally substituted with one or more substituents independently selected from halogen, hydroxy, $C_{1-5}$ alkoxy, nitro, and N($R^e$)$_2$; and further optionally substituted with 1-3 substituents independently selected from the group consisting of —C(=O)$R^a$, —$NR^bR^c$, —S(O)$_n R^d$ where n=0-2, hydroxy, $C_{1-6}$ alkoxy, halo$C_{1-6}$ alkoxy, aryl, heteroaryl and heterocyclyl; or COCH$_2$OC$_2$H$_5$OCH$_3$;

xiii) compounds of subset xii) above where AL$^1$ is alkyl or cycloalkyl;

xiv) $R^1$ is C(=O)(CH$_2$)$_m$AL$^1$ wherein m is 1-3, C(=O)(CH$_2$)$_m$Aryl, C(=O)(CH$_2$)$_m$Heterocyclic where m is 0-3; AL$^1$ is an aliphatic or alicyclic moiety; and AL$^1$, the aryl and heterocyclic moiety are independently optionally substituted with one or more substituents independently selected from the group consisting of hydrogen; halogen; hydroxy; nitro; CN; aryl; heteroaryl; —C(=O)$R^a$, —$NR^bR^c$, or —S(O)$_n R^d$ where n=0-2; $C_{1-6}$alkoxy optionally substituted with one or more substituents independently selected from halogen and $C_{1-6}$ alkyl; an optionally substituted fused bicyclic 8-12-membered aromatic or alicyclic ring containing 0-3 heteroatoms selected from the group consisting of N, O, and S; $C_{1-6}$ alkyl, $C_{2-6}$ alkenyl, $C_{2-6}$ alkynyl, or $C_{3-6}$ cycloalkyl, optionally substituted with one or more substituents independently selected from halogen, hydroxy, $C_{1-5}$ alkoxy, nitro, and N($R^e$)$_2$; and further optionally substituted with 1-3 substituents independently selected from the group consisting of —C(=O)$R^a$, —$NR^bR^c$, —S(O)$_n R^d$ where n=0-2, hydroxy, $C_{1-6}$ alkoxy, halo$C_{1-6}$ alkoxy, aryl, heteroaryl and heterocyclyl; or COCH$_2$OC$_2$H$_5$OCH$_3$;

xv) compounds of subset xiv) above where AL$^1$ is alkyl or cycloalkyl;

xvi) $R^1$ as SO$_2$AL$^1$, C(=O)AL$^1$, C(=O)NHAL$^1$, SO$_2$Aryl, C(=O)Aryl, or C(=O)NHAryl, wherein AL$^1$ is an aliphatic or alicyclic moiety; and AL$^1$ and the aryl moiety are independently optionally substituted with one or more substituents independently selected from the group consisting of hydrogen; halogen; hydroxy; nitro; CN; aryl; heteroaryl; —C(=O)$R^a$, —$NR^bR^c$, or —S(O)$_n R^d$ where n=0-2; $C_{1-6}$alkoxy optionally substituted with one or more substituents independently selected from halogen and $C_{1-6}$ alkyl; an optionally substituted fused bicyclic 8-12-membered aromatic or alicyclic ring containing 0-3 heteroatoms selected from the group consisting of N, O, and S; $C_{1-6}$ alkyl, $C_{2-6}$ alkenyl, $C_{2-6}$ alkynyl, or $C_{3-6}$ cycloalkyl, optionally substituted with one or more substituents independently selected from halogen, hydroxy, $C_{1-5}$ alkoxy, nitro, and N($R^e$)$_2$; and further optionally substituted with 1-3 substituents independently selected from the group consisting of —C(=O)$R^a$, —$NR^bR^c$, —S(O)$_n R^d$ where n=0-2, hydroxy, $C_{1-6}$ alkoxy, halo$C_{1-6}$ alkoxy, aryl, heteroaryl and heterocyclyl; or COCH$_2$OC$_2$H$_5$OCH$_3$;

xvii) compounds of subset xvii) above wherein AL$^1$ is alkyl or cycloalkyl;

xviii) $R^1$ is C(=O)Aryl optionally substituted with one or more substituents independently selected from the group consisting of hydrogen; CN; carboxy ester; —C(=O)$R^a$, or —S(O)$_n R^d$ where n=0-2; $C_{1-6}$alkoxy substituted with one or more substituents independently selected from halogen and $C_{1-6}$ alkyl; an optionally substituted fused bicyclic 8-12-membered aromatic or alicyclic ring containing 0-3 heteroatoms selected from the group consisting of N, O, and S; —N$R^f R^g$; $C_{1-6}$ alkyl substituted with one or more substituents independently selected from halogen, hydroxy, $C_{1-5}$ alkoxy, nitro, and N($R^e$)$_2$, or $C_{2-6}$ alkenyl, $C_{2-6}$ alkynyl, or $C_{3-6}$ cycloalkyl, optionally substituted with one or more substituents independently selected from halogen, hydroxy, $C_{1-5}$ alkoxy, nitro, and N($R^e$)$_2$;

xix) B or $R^3$ is a cis or trans CHCHAryl, CHCHHeterocyclic, phenoxyphenyl, or a heterocyclic group, optionally substituted with one or more substituents independently selected from the group consisting of hydrogen; halogen; hydroxy; nitro; CN; aryl; heteroaryl; —C(=O)$R^a$, —N$R^b R^c$, or —S(O)$_n R^d$ where n=0-2; $C_{1-6}$alkoxy optionally substituted with one or more substituents independently selected from halogen and $C_{1-6}$ alkyl; an optionally substituted fused bicyclic 8-12-membered aromatic or alicyclic ring containing 0-3 heteroatoms selected from the group consisting of N, O, and S; $C_{1-6}$ alkyl, $C_{2-6}$ alkenyl, $C_{2-6}$ alkynyl, or $C_{3-6}$ cycloalkyl, optionally substituted with one or more substituents independently selected from halogen, hydroxy, $C_{1-5}$ alkoxy, nitro, and N($R^e$)$_2$;

xx) B or $R^3$ is a cis or trans CHCHAryl, optionally substituted with one or more substituents independently selected from the group consisting of hydrogen; halogen; hydroxy; nitro; CN; aryl; heteroaryl; —C(=O)$R^a$, —N$R^b R^c$, or —S(O)$_n R^d$ where n=0-2; $C_{1-6}$alkoxy optionally substituted with one or more substituents independently selected from halogen and $C_{1-6}$ alkyl; an optionally substituted fused bicyclic 8-12-membered aromatic or alicyclic ring containing 0-3 heteroatoms selected from the group consisting of N, O, and S; $C_{1-6}$ alkyl, $C_{2-6}$ alkenyl, $C_{2-6}$ alkynyl, or $C_{3-6}$ cycloalkyl, optionally substituted with one or more substituents independently selected from halogen, hydroxy, $C_{1-5}$ alkoxy, nitro, and N($R^e$)$_2$;

xxi) B or $R^3$ is a cis or trans CHCHheterocyclic, phenoxyphenyl, or a heterocyclic group, optionally substituted with one or more substituents independently selected from the group consisting of hydrogen; halogen; hydroxy; nitro; CN; aryl; heteroaryl; —C(=O)$R^a$, —N$R^b R^c$, or —S(O)$_n R^d$ where n=0-2; $C_{1-6}$alkoxy optionally substituted with one or more substituents independently selected from halogen and $C_{1-6}$ alkyl; an optionally substituted fused bicyclic 8-12-membered aromatic or alicyclic ring containing 0-3 heteroatoms selected from the group consisting of N, O, and S; $C_{1-6}$ alkyl, $C_{2-6}$ alkenyl, $C_{2-6}$ alkynyl, or $C_{3-6}$ cycloalkyl, optionally substituted with one or more substituents independently selected from halogen, hydroxy, $C_{1-5}$ alkoxy, nitro, and N($R^e$)$_2$;

xxii) R is one or more substituents selected from the group consisting of hydrogen, halogen, hydroxyl, —NO$_2$, —CN, alkyl, alkenyl, alkynyl, cycloalkyl, cycloalkenyl, cycloalkynyl, heterocyclic, aryl, heteroaryl, -(alkyl)aryl, -(heteroalkyl)aryl, -(alkyl)heteroaryl or -(heteroalkyl) heteroaryl moiety; hydrogen, alkyl, heteroalkyl, aryl, heteroaryl, -(alkyl)aryl, -(alkyl)heteroaryl, —O$R^R$, —S(=O)$_n R^R$, —N($R^R$)$_2$, —SO$_2$N($R^R$)$_2$, —C(=O)$R^R$, —C(=O)N($R^R$)$_2$, —C(=O)O$R^R$, —N($R^R$)C(=O)$R^R$ or —N($R^R$)SO$_2 R^R$; wherein n is 0-2, and $R^R$, for each occurrence, is independently hydrogen, lower alkyl, lower heteroalkyl, aryl, heteroaryl, -(alkyl)aryl, or -(alkyl)heteroaryl;

xxiii) R is one or more substituents selected from the group consisting of hydrogen, halogen, hydroxyl, —NO$_2$, —CN, alkoxy, alkyl, alkenyl, alkynyl, cycloalkyl, cycloalkenyl, cycloalkynyl, heterocyclic, aryl, heteroaryl, -(alkyl)aryl, -(heteroalkyl)aryl, -(alkyl)heteroaryl, -(heteroalkyl)heteroaryl moiety, —S(=O)$_n R^d$, —N$R^b R^c$, and —C(=O)$R^a$; wherein n is 0-2;

xxiv) R is one or more substituents selected from hydrogen; halogen; hydroxy; nitro; CN; aryl; heteroaryl; —C(=O)$R^a$; —N$R^b R^c$; —S(O)$_n R^d$ where n=0-2; $C_{1-6}$alkoxy optionally substituted with one or more substituents independently selected from halogen and $C_{1-6}$ alkyl; an optionally substituted fused bicyclic 8-12-membered aromatic or alicyclic ring optionally containing 1-3 heteroatoms selected from the group consisting of N, O, and S; and $C_{1-6}$ alkyl, $C_{2-6}$ alkenyl, $C_{2-6}$ alkynyl, or $C_{3-6}$ cycloalkyl, each independently optionally substituted with one or more substituents independently selected from halogen, hydroxy, $C_{1-5}$ alkoxy, nitro, and N($R^e$)$_2$;

xxv) R is one or more substituents selected from hydrogen; halogen; hydroxy; nitro; CN; $C_{1-6}$ alkyl; $C_{1-6}$ alkoxy; halo$C_{1-6}$ alkoxy; —C(=O)$R^a$; —C(=O)O$R^a$; —O$R^a$ and —N$R^a R^b$; wherein $R^a$ and $R^b$ are independently lower alkyl or any two adjacent $R^a$ groups, or $R^a$ and $R^b$ groups, taken together, may form a heterocyclic moiety;

xxvi) R is one or more substituents selected from hydrogen; halogen; hydroxy or nitro;

xxvii) $R^a$, for each occurrence, is independently selected from the group consisting of hydrogen, hydroxy, $C_{1-6}$ alkyl, $C_{1-6}$ alkoxy, aryl, heteroaryl, and N$R^b R^c$, wherein $C_{1-6}$ alkyl and $C_{1-6}$ alkoxy are optionally substituted with one or more substituents independently selected from halogen, hydroxy, $C_{1-5}$ alkoxy, nitro, and N($R^e$)$_2$;

xxviii) $R^b$ and $R^c$, for each occurrence, are independently selected from the group consisting of hydrogen; hydroxy; SO$_2 R^d$; $C_{1-6}$ alkyl optionally substituted with one or more substituents independently selected from halogen, hydroxy, $C_{1-5}$ alkoxy, nitro, and N($R^e$)$_2$; $C_{1-6}$ alkoxy optionally substituted with one or more substituents independently selected from halogen, hydroxy, $C_{1-5}$ alkoxy, nitro and N($R^e$)$_2$; aryl optionally substituted with one or more substituents independently selected from halogen, hydroxy, $C_{1-4}$ alkyl, $C_{1-5}$ alkoxy, nitro, and N($R^e$)$_2$; and heteroaryl optionally substituted with one or more substituents independently selected from halogen, hydroxy, $C_{1-4}$ alkyl, $C_{1-5}$ alkoxy, nitro, and N($R^e$)$_2$;

xxix) $R^d$, for each occurrence, is independently selected from the group consisting of hydrogen; N($R^e$)$_2$; $C_{1-6}$ alkyl optionally substituted with one or more substituents independently selected from halogen, hydroxy, $C_{1-5}$ alkoxy, nitro, and N($R^e$)$_2$; aryl and heteroaryl;

xxx) $R^e$, for each occurrence, is independently hydrogen or $C_{1-6}$ alkyl;

xxxi) $R^f$ and $R^g$, for each occurrence, are independently selected from the group consisting of hydrogen; hydroxy; SO$_2 R^d$; $C_{1-6}$ alkyl substituted with one or more substituents independently selected from halogen, hydroxy, $C_{1-5}$ alkoxy, nitro, and N($R^e$)$_2$; $C_{1-6}$ alkoxy optionally substituted with one or more substituents independently selected from halogen, hydroxy, $C_{1-5}$ alkoxy, nitro and N(R$^e$)$_2$; aryl optionally substituted with one or more substituents independently selected from halogen, hydroxy, C$_{1-4}$ alkyl, C$_{1-5}$ alkoxy, nitro, and N(R$^e$)$_2$; and heteroaryl optionally substituted with one or more substituents independently selected from halogen, hydroxy, C$_{1-4}$ alkyl, C$_{1-5}$ alkoxy, nitro, and N(R$^e$)$_2$;

xxxii) R$^2$ is one or more substituents selected from the group consisting of hydrogen, halogen, hydroxyl, —NO$_2$, —CN, alkyl, alkenyl, alkynyl, cycloalkyl, cycloalkenyl, cycloalkynyl, heterocyclic, aryl, heteroaryl, -(alkyl)aryl, -(heteroalkyl)aryl, -(alkyl)heteroaryl or -(heteroalkyl)heteroaryl moiety; hydrogen, alkyl, heteroalkyl, aryl, heteroaryl, -(alkyl)aryl, -(alkyl)heteroaryl, —OR$^R$, —S(=O)$_n$R$^R$, —N(R$^R$)$_2$, —SO$_2$N(R$^R$)$_2$, —C(=O)R$^R$, —C(=O)N(R$^R$)$_2$, —C(=O)OR$^R$, —N(R$^R$)C(=O)R$^R$ or —N(R$^R$)SO$_2$R$^R$; wherein n is 0-2, and R$^R$, for each occurrence, is independently hydrogen, lower alkyl, lower heteroalkyl, aryl, heteroaryl, -(alkyl)aryl, or -(alkyl)heteroaryl;

xxxiii) R$^2$ is one or more substituents selected from the group consisting of hydrogen, halogen, hydroxyl, —NO$_2$, —CN, alkoxy, alkyl, alkenyl, alkynyl, cycloalkyl, cycloalkenyl, cycloalkynyl, heterocyclic, aryl, heteroaryl, -(alkyl)aryl, -(heteroalkyl)aryl, -(alkyl)heteroary, -(heteroalkyl)heteroaryl moiety, —S(=O)$_n$R$^d$, —NR$^b$R$^c$, and —C(=O)R$^a$; wherein n is 0-2;

xxxiv) R$^2$ is one or more substituents selected from hydrogen; halogen; hydroxy; nitro; CN; aryl; heteroaryl; —C(=O)R$^a$; —NR$^b$R$^c$; —S(O)$_n$R$^d$ where n=0-2; C$_{1-6}$alkoxy optionally substituted with one or more substituents independently selected from halogen and C$_{1-6}$ alkyl; an optionally substituted fused bicyclic 8-12-membered aromatic or alicyclic ring optionally containing 1-3 heteroatoms selected from the group consisting of N, O, and S; and C$_{1-6}$ alkyl, C$_{2-6}$ alkenyl, C$_{2-6}$ alkynyl, or C$_{3-6}$ cycloalkyl, each independently optionally substituted with one or more substituents independently selected from halogen, hydroxy, C$_{1-5}$ alkoxy, nitro, and N(R$^e$)$_2$;

xxxv) R$^2$ is one or more substituents selected from hydrogen; halogen; hydroxy; nitro; CN; C$_{1-6}$ alkyl; C$_{1-6}$ alkoxy; haloC$_{1-6}$ alkoxy; —C(=O)R$^a$; —C(=O)OR$^a$; —OR$^a$ and —NR$^a$R$^b$; wherein R$^a$ and R$^b$ are independently lower alkyl or any two adjacent R$^a$ groups, or R$^a$ and R$^b$ groups, taken together, may form a heterocyclic moiety;

xxxvi) A is an alicyclic, heteroalicyclic, aromatic or heteroaromatic moiety;

xxxvii) A is an optionally substituted aromatic or non-aromatic 5-6 membered monocyclic ring, optionally containing 1-4 heteroatoms selected from N, O or S; or an optionally substituted aromatic or non-aromatic 8-12 membered bicyclic ring, optionally containing 1-6 heteroatoms selected from N, O or S;

xxxviii) A is an aromatic or non-aromatic 5-6 membered monocyclic ring or 8-12 membered bicyclic ring, optionally substituted with one or more substituents selected from hydrogen; halogen; hydroxy; nitro; CN; C$_{1-6}$ alkyl; C$_{1-6}$ alkoxy; haloC$_{1-6}$ alkoxy; —C(=O)R$^a$; —C(=O)OR$^a$; —OR$^a$ and —NR$^a$R$^b$; wherein R$^a$ and R$^b$ are independently lower alkyl or any two adjacent R$^a$ groups, or R$^a$ and R$^b$ groups, taken together, may form a heterocyclic moiety;

xxxix) A is an aromatic or non-aromatic 5-6 membered monocyclic ring or 8-12 membered bicyclic ring, optionally substituted with one or more substituents selected from hydrogen; Cl; hydroxy; nitro; CN; —OCF$_3$; —C(=O)OMe; —C(=O)Me; —OMe; methyldioxyl; —NMe$_2$ and morpholinyl;

xl) A is optionally substituted aryl;
xli) A is optionally substituted phenyl or naphthyl;
xlii) A is optionally substituted heteroaryl;
xliii) A has the structure:

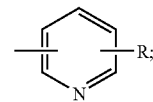

wherein R represents one or more substituents, as defined in subsets xxiii)-xxvii);

xlv) A is an optionally substituted C$_{1-6}$cycloalkyl or C$_{1-6}$cycloalkenyl moiety;
xlvi) A is optionally substituted cyclohexenyl;
xlvii) A is an optionally substituted heterocyclic moiety;
xlviii) A and/or Cy is one of:

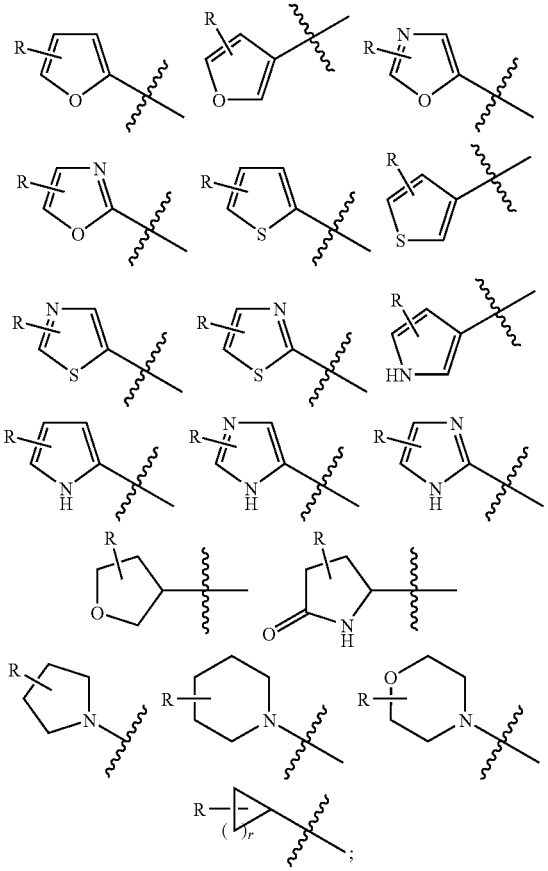

wherein R represents one or more substituents, as defined in subsets xxiii)-xxvii); and r is an integer from 1-6;

xlix) A and/or Cy is an optionally substituted 5-membered heterocyclic moiety having the structure:

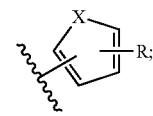

wherein R represents one or more substituents, as defined in subsets xxiii)-xxvii); and X is O, S or NR$^N$; wherein R$^N$ is hydrogen, lower alkyl, aryl, acyl or a nitrogen protecting group;

l) A and/or Cy is an optionally substituted 5-membered heterocyclic moiety having the structure:

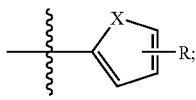

wherein R represents one or more substituents, as defined in subsets xxiii)-xxvii); and X is O, S or NR$^N$; wherein R$^N$ is hydrogen, lower alkyl, aryl, acyl or a nitrogen protecting group;

li) B is a moiety having the structure:

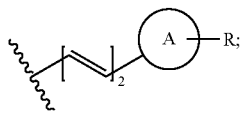

wherein A and R are as defined in classes and subclasses herein;

lii) B is a moiety having one of the structures:

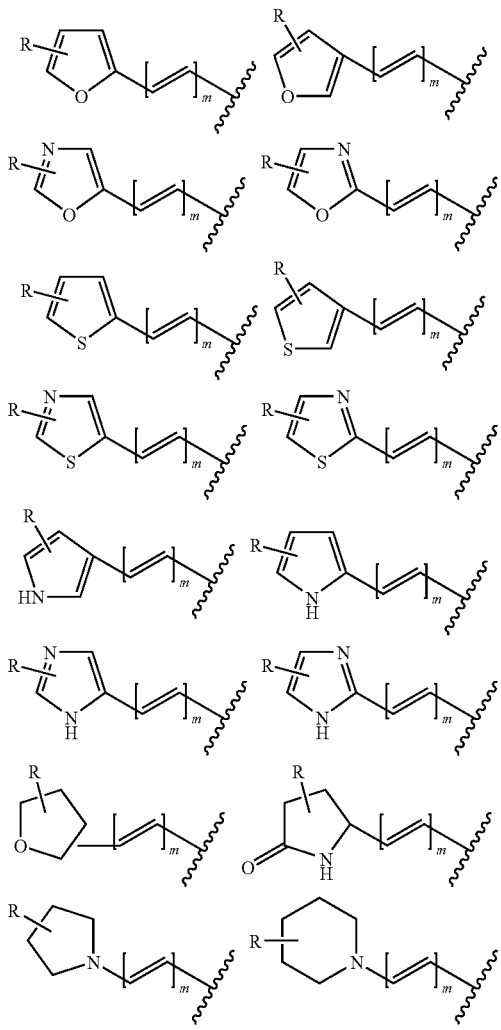

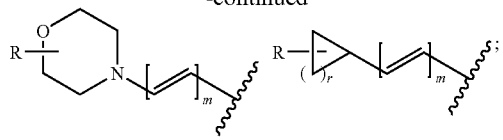

wherein R represents one or more substituents, as defined in subsets xxiii)-xxvii); m is an integer from 1-3; and r is an integer from 1-6;

liii) AR is phenyl or naphthyl; and/or liv) AR' is phenyl or naphthyl.

It will be appreciated that for each of the classes and subclasses described above and herein, any one or more occurrences of aliphatic and/or heteroaliphatic may independently be substituted or unsubstituted, linear or branched, saturated or unsaturated; any one or more occurrences of alicyclic and/or heteroalicyclic may independently be substituted or unsubstituted, saturated or unsaturated; and any one or more occurrences of aryl and/or heteroaryl may independently be substituted or unsubstituted.

The reader will also appreciate that all possible combinations of the variables described in i) through liv) above (e.g., R, R$^1$, and B, among others) are considered part of the invention. Thus, the invention encompasses any and all compounds of formula I generated by taking any possible permutation of variables R, R$^1$, and B, and other variables/substituents (e.g., A, R$^{1A}$, etc.) as further defined for R, R$^1$, and B, described in i) through liv) above.

For example, an exemplary combination of variables described in i) through liv) above includes those compounds of Formula I wherein:

B is a C(3)- or C(5)-substituent selected from the group consisting of optionally substituted cis or trans CHCHAryl, CHCHHeterocyclic, phenoxyphenyl and a heterocyclic group;

R$^1$ is C(=O)Aryl optionally substituted with one or more substituents independently selected from the group consisting of hydrogen; CN; carboxy ester; —C(=O)R$^a$, or —S(O)$_n$R$^d$ where n=0-2; C$_{1-6}$alkoxy substituted with one or more substituents independently selected from halogen and C$_{1-6}$ alkyl; an optionally substituted fused bicyclic 8-12-membered aromatic or alicyclic ring containing 0-3 heteroatoms selected from the group consisting of N, O, and S; —NR$^f$R$^g$; C$_{1-6}$ alkyl substituted with one or more substituents independently selected from halogen, hydroxy, C$_{1-5}$ alkoxy, nitro, and N(R$^e$)$_2$, or C$_{2-6}$ alkenyl, C$_{2-6}$ alkynyl, or C$_{3-6}$ cycloalkyl, optionally substituted with one or more substituents independently selected from halogen, hydroxy, C$_{1-5}$ alkoxy, nitro, and N(R$^e$)$_2$; and further optionally substituted with 1-3 substituents independently selected from the group consisting of —C(=O)R$^a$, —NR$^b$R$^c$, —S(O)$_n$R$^d$ where n=0-2, hydroxy, C$_{1-6}$ alkoxy, haloC$_{1-6}$ alkoxy, aryl, heteroaryl and heterocyclyl; and R is one or more substituents selected from hydrogen; halogen; hydroxy; nitro; CN; aryl; heteroaryl; —C(=O) R$^a$; —NR$^b$R$^c$; —S(O)$_n$R$^d$ where n=0-2; C$_{1-6}$alkoxy optionally substituted with one or more substituents independently selected from halogen and C$_{1-6}$ alkyl; an optionally substituted fused bicyclic 8-12-membered aromatic or alicyclic ring optionally containing 1-3 heteroatoms selected from the group consisting of N, O, and S; and C$_{1-6}$ alkyl, C$_{2-6}$ alkenyl, C$_{2-6}$ alkynyl, or C$_{3-6}$ cycloalkyl, each independently optionally substituted with one or more substituents independently selected from halogen, hydroxy, $C_{1-5}$ alkoxy, nitro, and $N(R^e)_2$;

wherein $R^a$, for each occurrence, is independently selected from the group consisting of hydrogen, hydroxy, $C_{1-6}$ alkyl, $C_{1-6}$ alkoxy, aryl, heteroaryl, and $NR^bR^c$, wherein $C_{1-6}$ alkyl and $C_{1-6}$ alkoxy are optionally substituted with one or more substituents independently selected from halogen, hydroxy, $C_{1-5}$ alkoxy, nitro, and $N(R^e)_2$;

$R^b$ and $R^c$, for each occurrence, are independently selected from the group consisting of hydrogen; hydroxy; $SO_2R^d$; $C_{1-6}$ alkyl optionally substituted with one or more substituents independently selected from halogen, hydroxy, $C_{1-5}$ alkoxy, nitro, and $N(R^e)_2$; $C_{1-6}$ alkoxy optionally substituted with one or more substituents independently selected from halogen, hydroxy, $C_{1-5}$ alkoxy, nitro and $N(R^e)_2$; aryl optionally substituted with one or more substituents independently selected from halogen, hydroxy, $C_{1-4}$ alkyl, $C_{1-5}$ alkoxy, nitro, and $N(R^e)_2$; and heteroaryl optionally substituted with one or more substituents independently selected from halogen, hydroxy, $C_{1-4}$ alkyl, $C_{1-5}$ alkoxy, nitro, and $N(R^e)_2$;

$R^d$, for each occurrence, is independently selected from the group consisting of hydrogen; $N(R^e)_2$; $C_{1-6}$ alkyl optionally substituted with one or more substituents independently selected from halogen, hydroxy, $C_{1-5}$ alkoxy, nitro, and $N(R^e)_2$; aryl and heteroaryl; and $R^e$, for each occurrence, is independently hydrogen or $C_{1-6}$ alkyl.

Other exemplary combinations are illustrated by compounds of the subgroups described below.

Thus, in another embodiment, methods are provided using compounds of the formula:

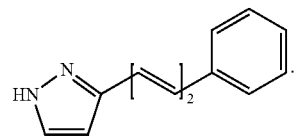

(II$^{41}$)

tautomers thereof; and pharmaceutically acceptable derivatives thereof;

wherein A and R are as defined generally and in classes and subclasses herein. In certain embodiments, A represents an optionally substituted aromatic or non-aromatic 5-6 membered monocyclic ring, optionally containing 1-4 heteroatoms selected from N, O or S; or an optionally substituted aromatic or non-aromatic 8-12 membered bicyclic ring, optionally containing 1-6 heteroatoms selected from N, O or S. In certain other embodiments, R is one or more substituents selected from the group consisting of hydrogen; halogen; hydroxy; nitro; CN; aryl; heteroaryl; —C(=O)$R^a$; —NR$^b$R$^c$; —S(O)$_n$R$^d$ where n=0-2; $C_{1-6}$alkoxy optionally substituted with one or more substituents independently selected from halogen and $C_{1-6}$ alkyl; an optionally substituted fused bicyclic 8-12-membered aromatic or alicyclic ring optionally containing 1-3 heteroatoms selected from the group consisting of N, O, and S; and $C_{1-6}$ alkyl, $C_{2-6}$ alkenyl, $C_{2-6}$ alkynyl, or $C_{3-6}$ cycloalkyl, each independently optionally substituted with one or more substituents independently selected from halogen, hydroxy, $C_{1-5}$ alkoxy, nitro, and $N(R^e)_2$; and further optionally substituted with 1-3 substituents independently selected from the group consisting of —C(=O)$R^a$, —NR$^b$R$^c$, —S(O)$_n$R$^d$ where n=0-2, hydroxy, $C_{1-6}$ alkoxy, halo$C_{1-6}$ alkoxy, aryl, heteroaryl and heterocyclyl;

wherein each occurrence of $R^a$ is independently selected from the group consisting of hydrogen, hydroxy, $C_{1-6}$ alkyl, $C_{1-6}$ alkoxy, aryl, heteroaryl, and $NR^bR^c$, wherein $C_{1-6}$ alkyl and $C_{1-6}$ alkoxy are optionally substituted with one or more substituents independently selected from halogen, hydroxy, $C_{1-5}$ alkoxy, nitro, and $N(R^e)_2$;

each occurrence of $R^b$ and $R^c$ is independently selected from the group consisting of hydrogen; hydroxy; $SO_2R^d$; $C_{1-6}$ alkyl optionally substituted with one or more substituents independently selected from halogen, hydroxy, $C_{1-5}$ alkoxy, nitro, and $N(R^e)_2$; $C_{1-6}$ alkoxy optionally substituted with one or more substituents independently selected from halogen, hydroxy, $C_{i-5}$ alkoxy, nitro and N(Re)$_2$; aryl optionally substituted with one or more substituents independently selected from halogen, hydroxy, $C_{1-4}$ alkyl, $C_{1-5}$ alkoxy, nitro, and $N(R^e)_2$; and heteroaryl optionally substituted with one or more substituents independently selected from halogen, hydroxy, $C_{1-4}$ alkyl, $C_{1-5}$ alkoxy, nitro, and $N(R^e)_2$;

each occurrence of $R^d$ is independently selected from the group consisting of hydrogen; $N(R^e)_2$; $C_{1-6}$ alkyl optionally substituted with one or more substituents independently selected from halogen, hydroxy, $C_{1-5}$ alkoxy, nitro, and $N(R^e)_2$; aryl and heteroaryl; and each occurrence of $R^e$ is independently hydrogen or $C_{1-6}$ alkyl.

A non-limiting example of compounds of this subgroup includes:

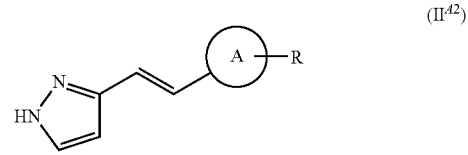

Thus, in another embodiment, methods are provided using compounds of the formula:

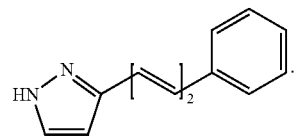

(II$^{42}$)

tautomers thereof, and pharmaceutically acceptable derivatives thereof;

wherein A and R are as defined generally and in classes and subclasses herein.

In certain exemplary embodiments, A is an aromatic or non-aromatic 5-6 membered monocyclic ring, optionally containing 1-4 heteroatoms selected from N, O or S; or an aromatic or non-aromatic 8-12 membered bicyclic ring, optionally containing 1-6 heteroatoms selected from N, O or S;

and R is one or more substituents selected from the group consisting of hydrogen; halogen; hydroxy; nitro; CN; aryl; heteroaryl; —C(=O)$R^a$; —NR$^b$R$^c$; —S(O)$_n$R$^d$ where n=0-2; $C_{1-6}$alkoxy optionally substituted with one or more substituents independently selected from halogen and $C_{1-6}$ alkyl; an optionally substituted fused bicyclic 8-12-membered aromatic or alicyclic ring optionally containing 1-3 heteroatoms selected from the group consisting of N, O, and S; and $C_{1-6}$ alkyl, $C_{2-6}$ alkenyl, $C_{2-6}$ alkynyl, or $C_{3-6}$ cycloalkyl, each independently optionally substituted with one or more substituents independently selected from halogen, hydroxy, $C_{1-5}$ alkoxy, nitro, and $N(R^e)_2$;

wherein each occurrence of $R^a$ is independently selected from the group consisting of hydrogen, hydroxy, $C_{1-6}$ alkyl, $C_{1-6}$ alkoxy, aryl, heteroaryl, and $NR^bR^c$, wherein $C_{1-6}$ alkyl and $C_{1-6}$ alkoxy are optionally substituted with one or more substituents independently selected from halogen, hydroxy, $C_{1-5}$ alkoxy, nitro, and $N(R^e)_2$;

each occurrence of $R^b$ and $R^c$ is independently selected from the group consisting of hydrogen; hydroxy; $SO_2R^d$; $C_{1-6}$ alkyl optionally substituted with one or more substituents independently selected from halogen, hydroxy, $C_{1-5}$ alkoxy, nitro, and $N(R^e)_2$; $C_{1-6}$ alkoxy optionally substituted with one or more substituents independently selected from halogen, hydroxy, $C_{1-5}$ alkoxy, nitro and $N(R^e)_2$; aryl optionally substituted with one or more substituents independently selected from halogen, hydroxy, $C_{1-4}$ alkyl, $C_{1-5}$ alkoxy, nitro, and $N(R^e)_2$; and heteroaryl optionally substituted with one or more substituents independently selected from halogen, hydroxy, $C_{1-4}$ alkyl, $C_{1-5}$ alkoxy, nitro, and $N(R^e)_2$;

each occurrence of $R^d$ is independently selected from the group consisting of hydrogen; $N(R^e)_2$; $C_{1-6}$ alkyl optionally substituted with one or more substituents independently selected from halogen, hydroxy, $C_{1-5}$ alkoxy, nitro, and $N(R^e)_2$; aryl and heteroaryl; and each occurrence of $R^e$ is independently hydrogen or $C_{1-6}$ alkyl;

or a prodrug, salt, hydrate, or ester thereof.

Non-limiting examples of compounds in the aforementioned subgroups include:

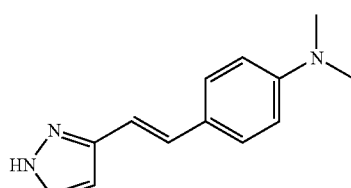
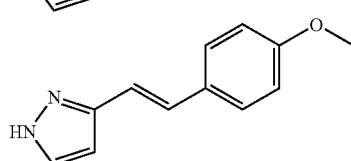
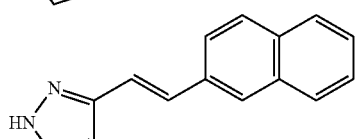
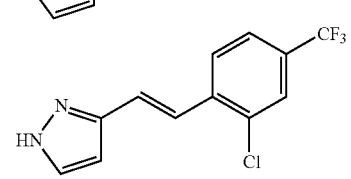
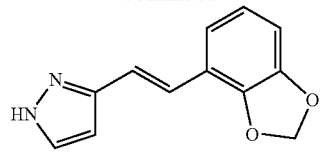
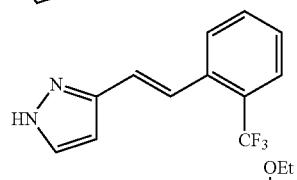
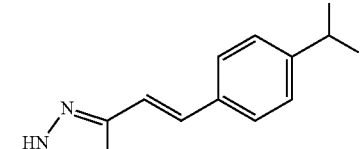
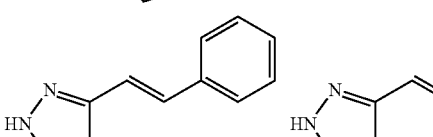
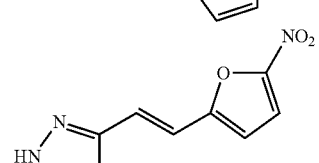
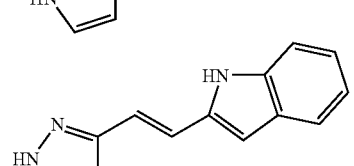
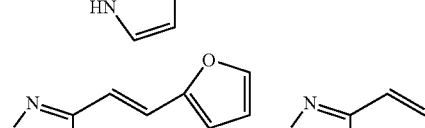
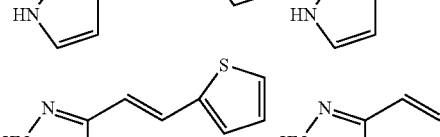
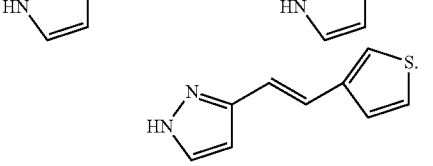

Thus, in another embodiment, methods are provided using compounds of the formula:

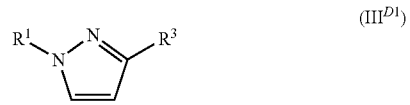

(III$^{D1}$)

C(5)-positional isomers thereof; and pharmaceutically acceptable derivatives thereof;

wherein $R^1$ is $C(=O)(CH_2)_mAL^2$, $C(=O)OAL^2$, $C(=O)(CH_2)_m$Aryl, $C(=O)$OAryl, $C(=O)$Heteroaryl or C(=O)Heterocyclic; where m is an integer from 1-3; AL² is an aliphatic or alicyclic moiety; and AL², the aryl, heteroaryl and heterocyclic moiety are independently optionally substituted with one or more substituents independently selected from hydrogen; halogen; hydroxy; nitro; CN; aryl; heteroaryl; —C(=O)R$^a$, —NR$^b$R$^c$, or —S(O)$_n$R$^d$ where n=0-2; C$_{1-6}$alkoxy optionally substituted with one or more substituents independently selected from halogen and C$_{1-6}$ alkyl; an optionally substituted fused bicyclic 8-12-membered aromatic or alicyclic ring containing 0-3 heteroatoms selected from the group consisting of N, O, and S; C$_{1-6}$ alkyl, C$_{2-6}$ alkenyl, C$_{2-6}$ alkynyl, or C$_{3-6}$ cycloalkyl, optionally substituted with one or more substituents independently selected from halogen, hydroxy, C$_{1-5}$ alkoxy, nitro, and N(R$^e$)$_2$; and further optionally substituted with 1-3 substituents independently selected from the group consisting of —C(=O)R$^a$, —NR$^b$R$^c$, —S(O)$_n$R$^d$ where n=0-2, hydroxy, C$_{1-6}$ alkoxy, haloC$_{1-6}$ alkoxy, aryl, heteroaryl and heterocyclyl; or COCH$_2$OC$_2$H$_5$OCH$_3$; and R³ is a cis or trans CHCHAryl, CHCHHeterocyclic, phenoxyphenyl, or a heterocyclic group, wherein the aryl, heterocyclic or phenoxyphenyl moiety may be optionally substituted with one or more substituents independently selected from the group consisting of hydrogen; halogen; hydroxy; nitro; CN; aryl; heteroaryl; —C(=O)R$^a$, —NR$^b$R$^c$, or —S(O)$_n$R$^d$ where n=0-2; C$_{1-6}$alkoxy optionally substituted with one or more substituents independently selected from halogen and C$_{1-6}$ alkyl; an optionally substituted fused bicyclic 8-12-membered aromatic or alicyclic ring containing 0-3 heteroatoms selected from the group consisting of N, O, and S; C$_{1-6}$ alkyl, C$_{2-6}$ alkenyl, C$_{2-6}$ alkynyl, or C$_{3-6}$ cycloalkyl, optionally substituted with one or more substituents independently selected from halogen, hydroxy, C$_{1-5}$ alkoxy, nitro, and N(R$^e$)$_2$; and further optionally substituted with 1-3 substituents independently selected from the group consisting of —C(=O)R$^a$, —NR$^b$R$^c$, —S(O)$_n$R$^d$ where n=0-2, hydroxy, C$_{1-6}$ alkoxy, haloC$_{1-6}$ alkoxy, aryl, heteroaryl and heterocyclyl;

wherein R$^a$ is selected from the group consisting of hydrogen, hydroxy, C$_{1-6}$ alkyl, C$_{1-6}$ alkoxy, aryl, heteroaryl, and NR$^b$R$^c$, wherein C$_{1-6}$ alkyl and C$_{1-6}$ alkoxy are optionally substituted with one or more substituents independently selected from halogen, hydroxy, C$_{1-5}$ alkoxy, nitro, and N(R$^e$)$_2$;

R$^b$ and R$^c$ are independently selected from the group consisting of hydrogen; hydroxy; SO$_2$R$^d$; C$_{1-6}$ alkyl optionally substituted with one or more substituents independently selected from halogen, hydroxy, C$_{1-5}$ alkoxy, nitro, and N(R$^e$)$_2$; C$_{1-6}$ alkoxy optionally substituted with one or more substituents independently selected from halogen, hydroxy, C$_{1-5}$ alkoxy, nitro and N(R$^e$)$_2$; aryl optionally substituted with one or more substituents independently selected from halogen, hydroxy, C$_{1-4}$ alkyl, C$_{1-5}$ alkoxy, nitro, and N(R$^e$)$_2$; and heteroaryl optionally substituted with one or more substituents independently selected from halogen, hydroxy, C$_{1-4}$ alkyl, C$_{1-5}$ alkoxy, nitro, and N(R$^e$)$_2$;

R$^d$ is selected from the group consisting of hydrogen; N(R$^e$)$_2$; C$_{1-6}$ alkyl optionally substituted with one or more substituents independently selected from halogen, hydroxy, C$_{1-5}$ alkoxy, nitro, and N(R$^e$)$_2$; aryl and heteroaryl; and R$^e$ is hydrogen or C$_{1-6}$ alkyl.

In certain embodiments, for the compounds of formula (III$^{D1}$) above, AL² is an alkyl or cycloalkyl moiety.

In certain embodiments, for the compounds of formula (III$^{D1}$) above, R³ is a cis or trans CHCHHeterocyclic, phenoxyphenyl, or a heterocyclic group, optionally substituted with one or more substituents independently selected from the group consisting of hydrogen; halogen; hydroxy; nitro; CN; aryl; heteroaryl; —C(=O)R$^a$, —NR$^b$R$^c$, or —S(O)$_n$R$^d$ where n=0-2; C$_{1-6}$alkoxy optionally substituted with one or more substituents independently selected from halogen and C$_{1-6}$alkyl; an optionally substituted fused bicyclic 8-12-membered aromatic or alicyclic ring containing 0-3 heteroatoms selected from the group consisting of N, O, and S; C$_{1-6}$ alkyl, C$_{2-6}$ alkenyl, C$_{2-6}$ alkynyl, or C$_{3-6}$ cycloalkyl, optionally substituted with one or more substituents independently selected from halogen, hydroxy, C$_{1-5}$ alkoxy, nitro, and N(R$^e$)$_2$; and further optionally substituted with 1-3 substituents independently selected from the group consisting of —C(=O)R$^a$, —NR$^b$R$^c$, —S(O)$_n$R$^d$ where n=0-2, hydroxy, C$_{1-6}$ alkoxy, haloC$_{1-6}$ alkoxy, aryl, heteroaryl and heterocyclyl;

wherein R$^a$ is selected from the group consisting of hydrogen, hydroxy, C$_{1-6}$ alkyl, C$_{1-6}$ alkoxy, aryl, heteroaryl, and NR$^b$R$^c$, wherein C$_{1-6}$ alkyl and C$_{1-6}$ alkoxy are optionally substituted with one or more substituents independently selected from halogen, hydroxy, C$_{1-5}$ alkoxy, nitro, and N(R$^e$)$_2$;

R$^b$ and R$^c$ are independently selected from the group consisting of hydrogen; hydroxy; SO$_2$R$^d$; C$_{1-6}$ alkyl optionally substituted with one or more substituents independently selected from halogen, hydroxy, C$_{1-5}$ alkoxy, nitro, and N(R$^e$)$_2$; C$_{1-6}$ alkoxy optionally substituted with one or more substituents independently selected from halogen, hydroxy, C$_{1-5}$ alkoxy, nitro and N(R$^e$)$_2$; aryl optionally substituted with one or more substituents independently selected from halogen, hydroxy, C$_{1-4}$ alkyl, C$_{1-5}$ alkoxy, nitro, and N(R$^e$)$_2$;

and heteroaryl optionally substituted with one or more substituents independently selected from halogen, hydroxy, C$_{1-4}$ alkyl, C$_{1-5}$ alkoxy, nitro, and N(R$^e$)$_2$;

R$^d$ is selected from the group consisting of hydrogen; N(R$^e$)$_2$; C$_{1-6}$ alkyl optionally substituted with one or more substituents independently selected from halogen, hydroxy, C$_{1-5}$ alkoxy, nitro, and N(R$^e$)$_2$; aryl and heteroaryl; and R$^e$ is hydrogen or C$_{1-6}$ alkyl.

Non-limiting examples of compounds of this subgroup include:

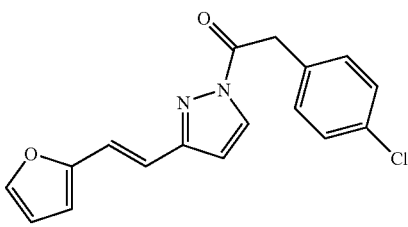

31
-continued
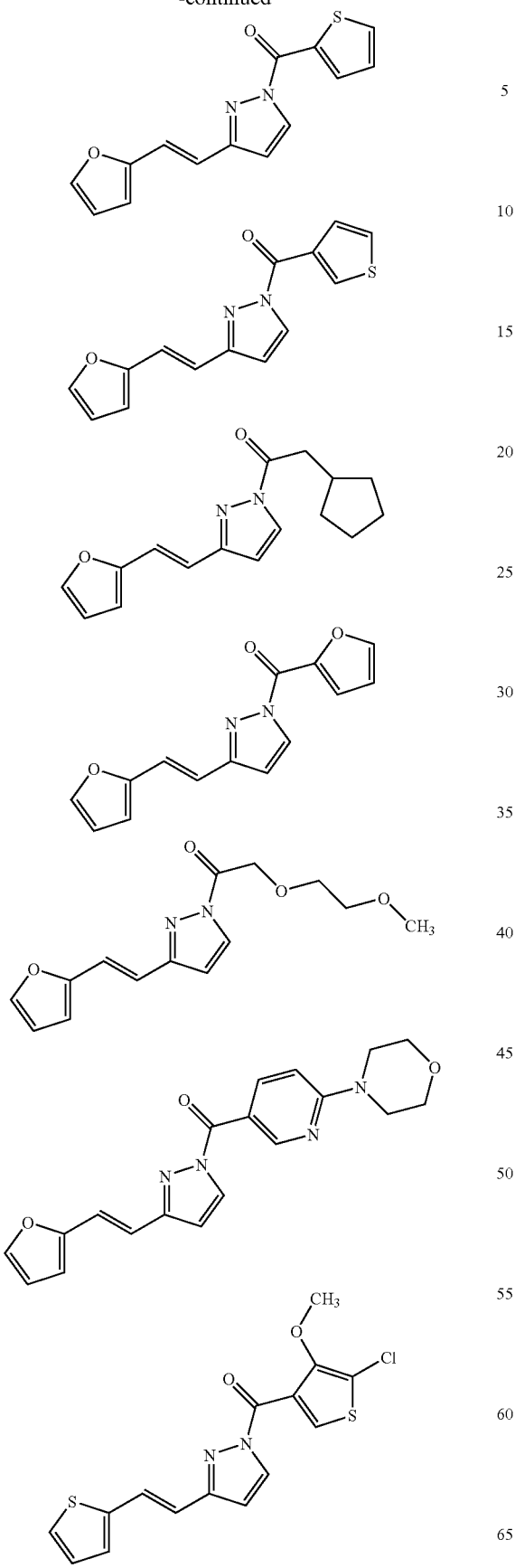
32
-continued
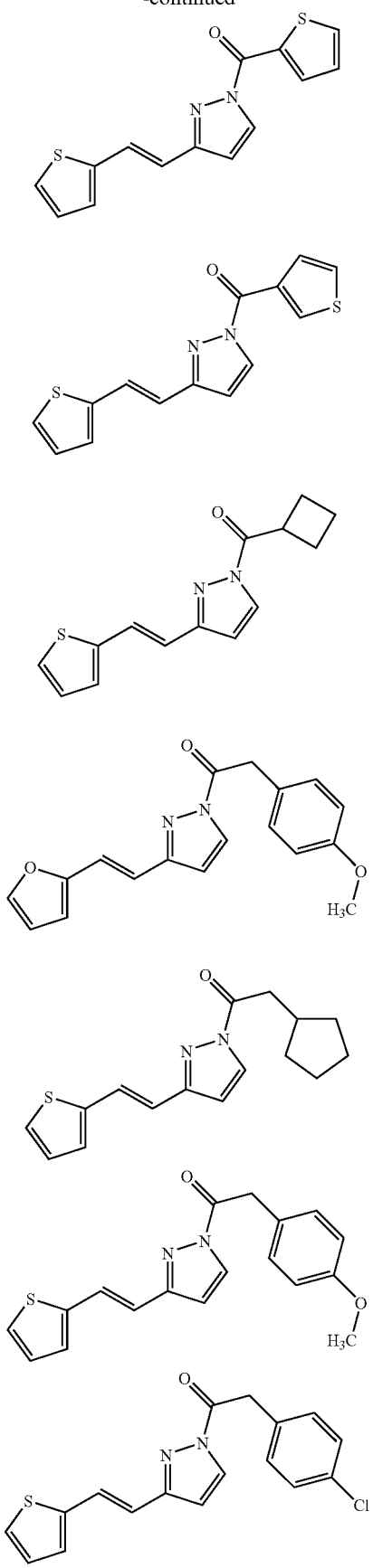

-continued

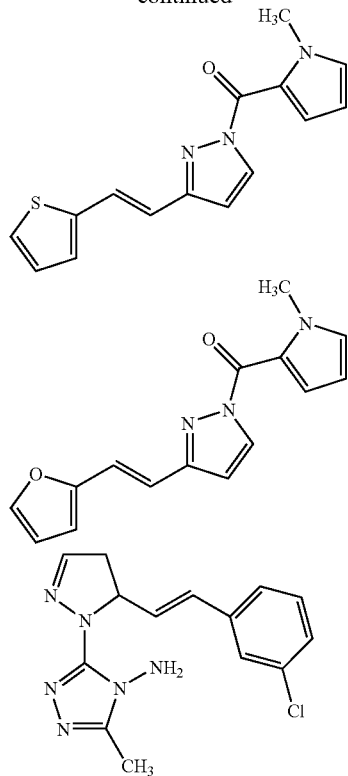

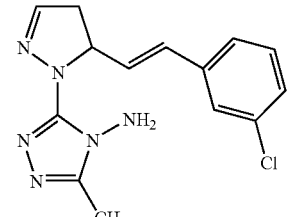

As mentioned above and herein throughout, although the compound structures depicted herein are substituted at the 1 and 3 positions, the invention embraces such positional isomers where the 3-substituent is at the 5 position, and any combination thereof.

In another aspect of compounds of Formula (III$^{D1}$), R$^3$ is a cis or trans CHCHAryl, optionally substituted with one or more substituents independently selected from the group consisting of hydrogen; halogen; hydroxy; nitro; CN; aryl; heteroaryl; —C(═O)R$^a$, —NR$^b$R$^c$, or —S(O)$_n$R$^d$ where n=0-2; C$_{1-6}$alkoxy optionally substituted with one or more substituents independently selected from halogen and C$_{1-6}$ alkyl; an optionally substituted fused bicyclic 8-12-membered aromatic or alicyclic ring containing 0-3 heteroatoms selected from the group consisting of N, O, and S; C$_{1-6}$ alkyl, C$_{2-6}$ alkenyl, C$_{2-6}$ alkynyl, or C$_{3-6}$ cycloalkyl, optionally substituted with one or more substituents independently selected from halogen, hydroxy, C$_{1-5}$ alkoxy, nitro, and N(R$^e$)$_2$; and further optionally substituted with 1-3 substituents independently selected from the group consisting of —C(═O)R$^a$, —NR$^b$R$^c$, —S(O)$_n$R$^d$ where n=0-2, hydroxy, C$_{1-6}$ alkoxy, haloC$_{1-6}$ alkoxy, aryl, heteroaryl and heterocyclyl;

wherein R$^a$ is selected from the group consisting of hydrogen, hydroxy, C$_{1-6}$ alkyl, C$_{1-6}$ alkoxy, aryl, heteroaryl, and NR$^b$R$^c$, wherein C$_{1-6}$ alkyl and C$_{1-6}$ alkoxy are optionally substituted with one or more substituents independently selected from halogen, hydroxy, C$_{1-5}$ alkoxy, nitro, and N(R$^e$)$_2$;

R$^b$ and R$^c$ are independently selected from the group consisting of hydrogen; hydroxy; SO$_2$R$^d$; C$_{1-6}$ alkyl optionally substituted with one or more substituents independently selected from halogen, hydroxy, C$_{1-5}$ alkoxy, nitro, and N(R$^e$)$_2$; C$_{1-6}$ alkoxy optionally substituted with one or more substituents independently selected from halogen, hydroxy, C$_{1-5}$ alkoxy, nitro and N(R$^e$)$_2$;

aryl optionally substituted with one or more substituents independently selected from halogen, hydroxy, C$_{1-4}$ alkyl, C$_{1-5}$ alkoxy, nitro, and N(R$^e$)$_2$; and heteroaryl optionally substituted with one or more substituents independently selected from halogen, hydroxy, C$_{1-4}$ alkyl, C$_{1-5}$ alkoxy, nitro, and N(R$^e$)$_2$;

R$^d$ is selected from the group consisting of hydrogen; N(R$^e$)$_2$; C$_{1-6}$ alkyl optionally substituted with one or more substituents independently selected from halogen, hydroxy, C$_{1-5}$ alkoxy, nitro, and N(R$^e$)$_2$; aryl and heteroaryl; and R$^e$ is hydrogen or C$_{1-6}$ alkyl.

Non-limiting examples of compounds of this subgroup include:

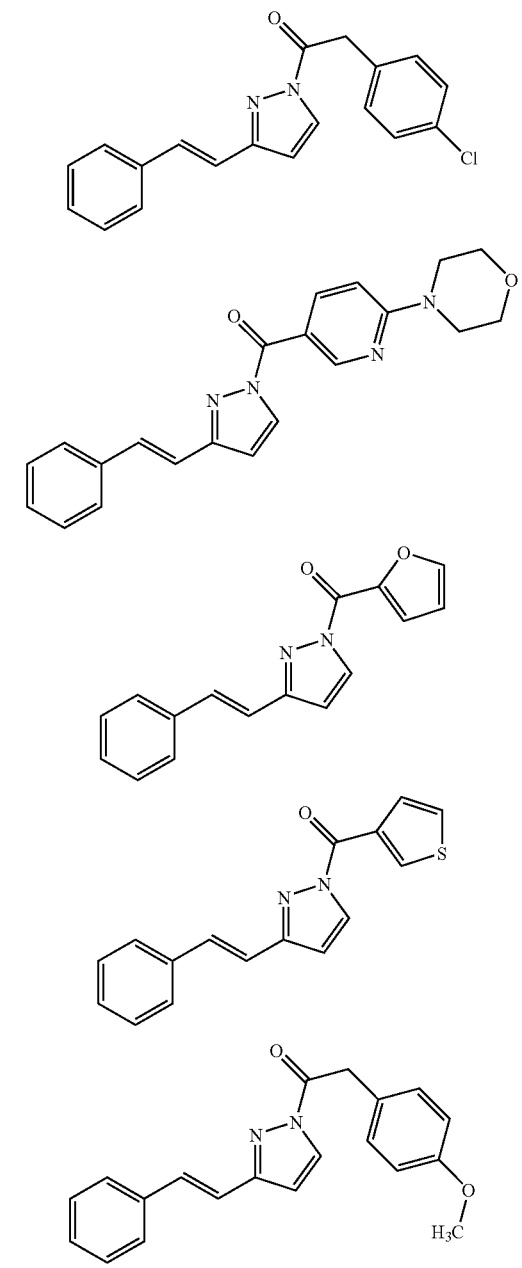

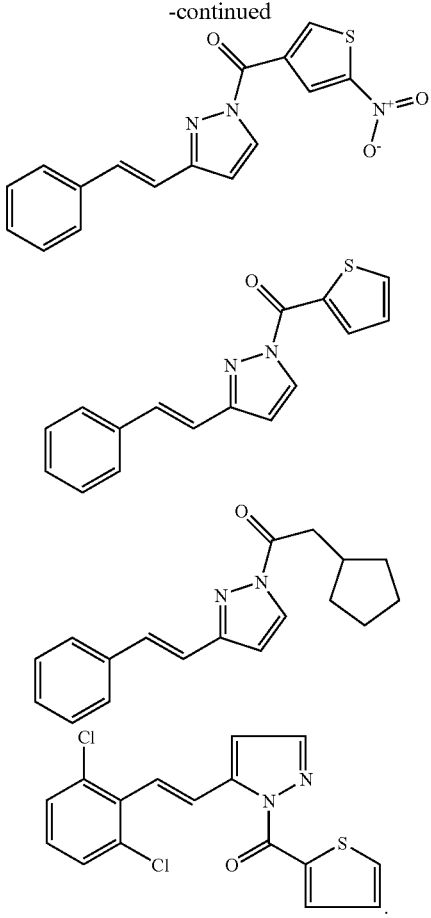

Thus, in another embodiment, methods are provided using compounds of the formula:

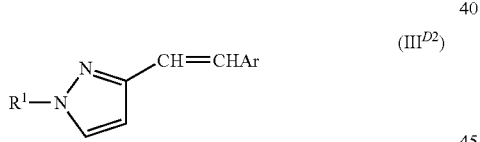

(III$^{D2}$)

C(5)-positional isomers thereof; and pharmaceutically acceptable derivatives thereof;

wherein $R^1$ is $SO_2AL^2$, $C(=O)(CH_2)_mAL^2$, $C(=O)OAL^2$, $C(=O)NHAL^2$, $SO_2Aryl$, $C(=O)(CH_2)_mAryl$, $C(=O)OAryl$, $C(=O)Oheterocyclic$, $C(=O)(CH_2)_m$Heterocyclic, or $C(=O)NHAryl$; wherein m is an integer from 1-3; $AL^2$ is an aliphatic or alicyclic moiety; and $AL^2$, the aryl and heterocyclic moiety are independently optionally substituted with one or more substituents independently selected from the group consisting of hydrogen; halogen; hydroxy; nitro; CN; aryl; heteroaryl; —C(=O)$R^a$, —NR$^b$R$^c$, or —S(O)$_n$R$^d$ where n=0-2; $C_{1-6}$alkoxy optionally substituted with one or more substituents independently selected from halogen and $C_{1-6}$ alkyl; an optionally substituted fused bicyclic 8-12-membered aromatic or alicyclic ring containing 0-3 heteroatoms selected from the group consisting of N, O, and S; $C_{1-6}$ alkyl, $C_{2-6}$ alkenyl, $C_{2-6}$ alkynyl, or $C_{3-6}$ cycloalkyl, optionally substituted with one or more substituents independently selected from halogen, hydroxy, $C_{1-5}$ alkoxy, nitro, and N(R$^e$)$_2$; and further optionally substituted with 1-3 substituents independently selected from the group consisting of —C(=O)$R^a$, —NR$^b$R$^c$, —S(O)$_n$R$^d$ where n=0-2, hydroxy, $C_{1-6}$ alkoxy, halo$C_{1-6}$ alkoxy, aryl, heteroaryl and heterocyclyl; or $COCH_2OC_2H_5OCH_3$; and CHCHAr is a cis or trans CH=CHAryl optionally substituted with one or more substituents independently selected from the group consisting of hydrogen; halogen; hydroxy; nitro; CN; aryl; heteroaryl; —C(=O)$R^a$, —NR$^b$R$^c$, or —S(O)$_n$R$^d$ where n=0-2; $C_{1-6}$alkoxy optionally substituted with one or more substituents independently selected from halogen and $C_{1-6}$ alkyl; an optionally substituted fused bicyclic 8-12-membered aromatic or alicyclic ring containing 0-3 heteroatoms selected from the group consisting of N, O, and S; $C_{1-6}$ alkyl, $C_{2-6}$ alkenyl, $C_{2-6}$ alkynyl, or $C_{3-6}$ cycloalkyl, optionally substituted with one or more substituents independently selected from halogen, hydroxy, $C_{1-5}$ alkoxy, nitro, and N(R$^e$)$_2$;

wherein $R^a$ is selected from the group consisting of hydrogen, hydroxy, $C_{1-6}$ alkyl, $C_{1-6}$ alkoxy, aryl, heteroaryl, and NR$^b$R$^c$, wherein $C_{1-6}$ alkyl and $C_{1-6}$ alkoxy are optionally substituted with one or more substituents independently selected from halogen, hydroxy, $C_{1-5}$ alkoxy, nitro, and N(R$^e$)$_2$;

$R^b$ and $R^c$ are independently selected from the group consisting of hydrogen; hydroxy; SO$_2$R$^d$; $C_{1-6}$ alkyl optionally substituted with one or more substituents independently selected from halogen, hydroxy, $C_{1-5}$ alkoxy, nitro, and N(R$^e$)$_2$; $C_{1-6}$ alkoxy optionally substituted with one or more substituents independently selected from halogen, hydroxy, $C_{1-5}$ alkoxy, nitro and N(R$^e$)$_2$; aryl optionally substituted with one or more substituents independently selected from halogen, hydroxy, $C_{1-4}$ alkyl, $C_{1-5}$ alkoxy, nitro, and N(R$^e$)$_2$; and heteroaryl optionally substituted with one or more substituents independently selected from halogen, hydroxy, $C_{1-4}$ alkyl, $C_{1-5}$ alkoxy, nitro, and N(R$^e$)$_2$;

$R^d$ is selected from the group consisting of hydrogen; N(R$^e$)$_2$; $C_{1-6}$ alkyl optionally substituted with one or more substituents independently selected from halogen, hydroxy, $C_{1-5}$ alkoxy, nitro, and N(R$^e$)$_2$; aryl and heteroaryl; and $R^e$ is hydrogen or $C_{1-6}$ alkyl.

In certain embodiments, for compounds of Formula (III$^{D2}$), $R^1$ is $C(=O)(CH_2)_mAL^2$, $C(=O)OAL^2$, $C(=O)(CH_2)_mAryl$, $C(=O)OAryl$, $C(=O)OHeterocyclic$ or $C(=O)(CH_2)_m$Heterocyclic; wherein m is an integer from 1-3; $AL^2$ is an aliphatic or alicyclic moiety; and $AL^2$, the aryl and heterocyclic moiety are independently optionally substituted with one or more substituents independently selected from the group consisting of hydrogen; halogen; hydroxy; nitro; CN; aryl; heteroaryl; —C(=O)$R^a$, —NR$^b$R$^c$, or —S(O)$_n$R$^d$ where n=0-2; $C_{1-6}$alkoxy optionally substituted with one or more substituents independently selected from halogen and $C_{1-6}$alkyl; an optionally substituted fused bicyclic 8-12-membered aromatic or alicyclic ring containing 0-3 heteroatoms selected from the group consisting of N, O, and S; $C_{1-6}$ alkyl, $C_{2-6}$ alkenyl, $C_{2-6}$ alkynyl, or $C_{3-6}$ cycloalkyl, optionally substituted with one or more substituents independently selected from halogen, hydroxy, $C_{1-5}$ alkoxy, nitro, and N(R$^e$)$_2$; and further optionally substituted with 1-3 substituents independently selected from the group consisting of —C(=O)$R^a$, —NR$^b$R$^c$, —S(O)$_n$R$^d$ where n=0-2, hydroxy, $C_{1-6}$ alkoxy, halo$C_{1-6}$ alkoxy, aryl, heteroaryl and heterocyclyl; or $COCH_2OC_2H_5OCH_3$.

Non-limiting examples of compound of this subgroup include:

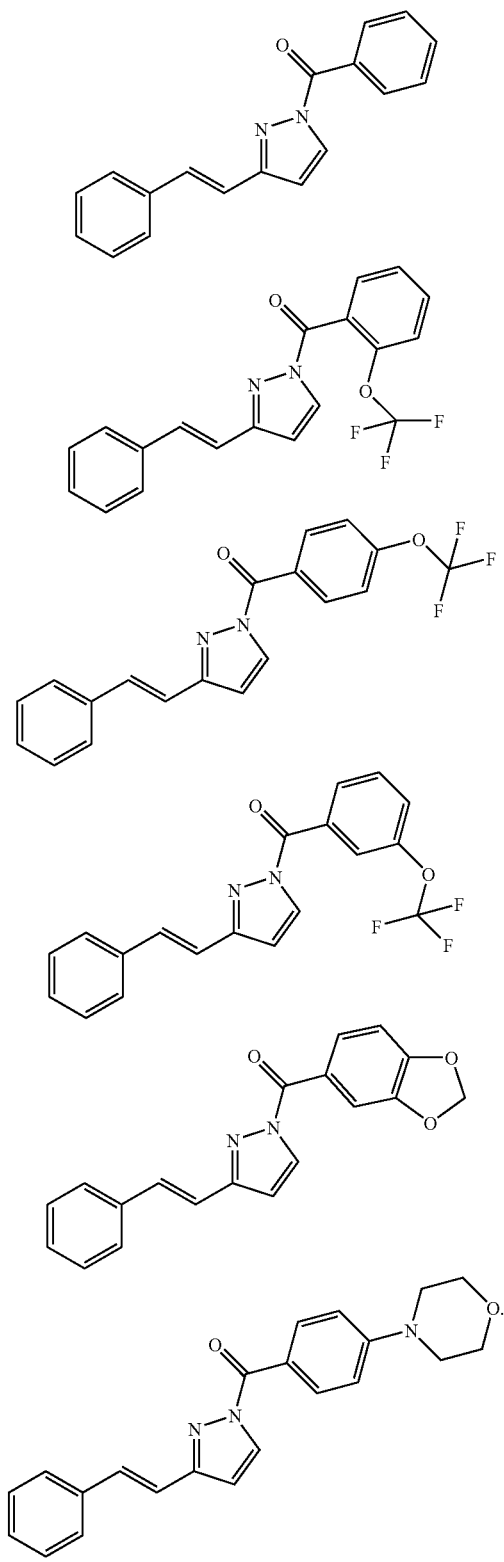

In certain other embodiments, for compounds of Formula (III$^{D2}$), R$^1$ is SO$_2$AL$^2$, C(=O)AL$^2$, C(=O)NHAL$^2$, SO$_2$Aryl, C(=O)Aryl, or C(=O)NHAryl; wherein AL$^2$ is an aliphatic or alicyclic moiety; and AL$^2$ and the aryl moiety are independently optionally substituted with one or more substituents independently selected from the group consisting of hydrogen; halogen; hydroxy; nitro; CN; aryl; heteroaryl; —C(=O)R$^a$, —NR$^b$R$^c$, or —S(O)$_n$R$^d$ where n=0-2; C$_{1-6}$alkoxy optionally substituted with one or more substituents independently selected from halogen and C$_{1-6}$ alkyl; an optionally substituted fused bicyclic 8-12-membered aromatic or alicyclic ring containing 0-3 heteroatoms selected from the group consisting of N, O, and S; C$_{1-6}$ alkyl, C$_{2-6}$ alkenyl, C$_{2-6}$ alkynyl, or C$_{3-6}$ cycloalkyl, optionally substituted with one or more substituents independently selected from halogen, hydroxy, C$_{1-5}$ alkoxy, nitro, and N(R$^e$)$_2$; and further optionally substituted with 1-3 substituents independently selected from the group consisting of —C(=O)R$^a$, —NR$^b$R$^c$, —S(O)$_n$R$^d$ where n=0-2, hydroxy, C$_{1-6}$ alkoxy, haloC$_{1-6}$ alkoxy, aryl, heteroaryl and heterocyclyl; or COCH$_2$OC$_2$H$_5$OCH$_3$.

Non-limiting examples of this subgroup include:

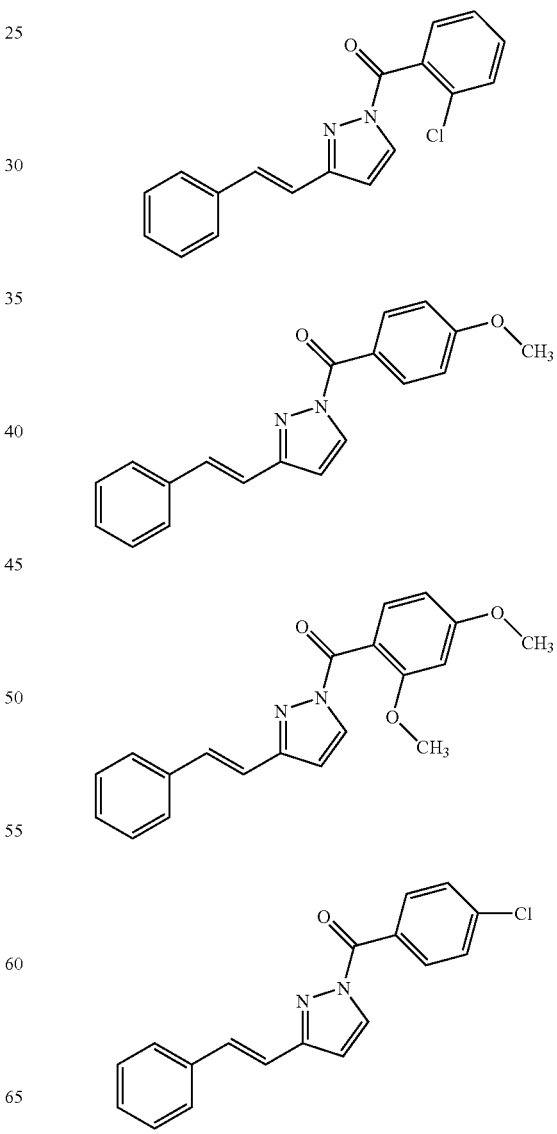

-continued

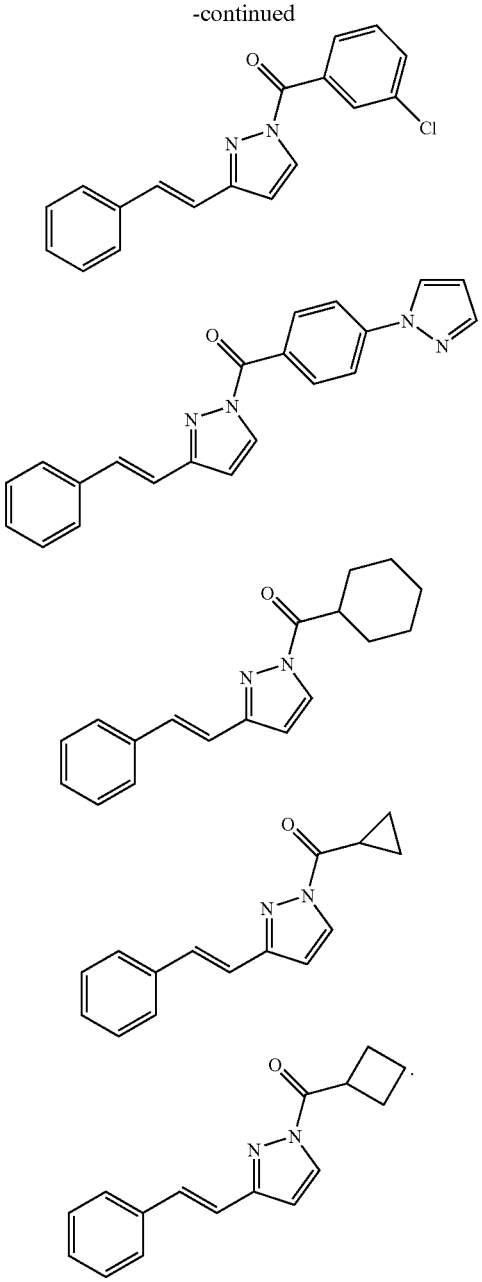

In certain embodiments, for the compounds of subgroup XI above, AL² is an alkyl or cycloalkyl moiety.

Thus, in another embodiment, methods are provided using compounds of the formula:

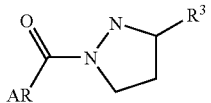

(III^D3)

C(5)-positional isomer thereof; and pharmaceutically acceptable derivatives thereof;

wherein AR is an optionally fused 3-12 membered aromatic or alicyclic mono- or bicyclic-ring containing 0-3 heteroatoms selected from the group consisting of N, O, and S optionally substituted with one or more substituents independently selected from the group consisting of hydrogen; halogen; hydroxy; nitro; CN; aryl; heteroaryl; heterocycle; carboxy ester; —C(═O)$R^a$, —$NR^bR^c$, or —S(O)$_n R^d$ where n=0-2; $C_{1-6}$alkoxy substituted with one or more substituents independently selected from halogen and $C_{1-6}$ alkyl; an optionally substituted fused bicyclic 8-12-membered aromatic or alicyclic ring containing 0-3 heteroatoms selected from the group consisting of N, O, and S; —$NR^fR^g$; $C_{1-6}$ alkyl, $C_{2-6}$ alkenyl, $C_{2-6}$ alkynyl, or $C_{3-6}$ cycloalkyl, optionally substituted with one or more substituents independently selected from halogen, hydroxy, $C_{1-5}$ alkoxy, nitro, and $N(R^e)_2$; and further optionally substituted with 1-3 substituents independently selected from the group consisting of —C(═O)$R^a$, —$NR^bR^c$, —S(O)$_n R^d$ where n=0-2, hydroxy, $C_{1-6}$ alkoxy, halo$C_{1-6}$alkoxy, aryl, heteroaryl and heterocyclyl; and $R^3$ is a cis or trans CHCHheterocyclic, phenoxyphenyl, or a heterocyclic group, optionally substituted with one or more substituents independently selected from the group consisting of hydrogen; halogen; hydroxy; nitro; CN; aryl; heteroaryl; —C(═O)$R^a$, —$NR^bR^c$, or —S(O)$_n R^d$ where n=0-2; $C_{1-6}$alkoxy optionally substituted with one or more substituents independently selected from halogen and $C_{1-6}$ alkyl; an optionally substituted fused bicyclic 8-12-membered aromatic or alicyclic ring containing 0-3 heteroatoms selected from the group consisting of N, O, and S; $C_{1-6}$ alkyl, $C_{2-6}$ alkenyl, $C_{2-6}$ alkynyl, or $C_{3-6}$ cycloalkyl, optionally substituted with one or more substituents independently selected from halogen, hydroxy, $C_{1-5}$ alkoxy, nitro, and $N(R^e)_2$; and further optionally substituted with 1-3 substituents independently selected from the group consisting of —C(═O)$R^a$, —$NR^bR^c$, —S(O)$_n R^d$ where n=0-2, hydroxy, $C_{1-6}$ alkoxy, halo$C_{1-6}$ alkoxy, aryl, heteroaryl and heterocyclyl;

wherein $R^a$ is selected from the group consisting of hydrogen, hydroxy, $C_{1-6}$ alkyl, $C_{1-6}$ alkoxy, aryl, heteroaryl, and $NR^bR^c$, wherein $C_{1-6}$ alkyl and $C_{1-6}$ alkoxy are optionally substituted with one or more substituents independently selected from halogen, hydroxy, $C_{1-5}$ alkoxy, nitro, and $N(R^e)_2$;

$R^b$ and $R^c$ are independently selected from the group consisting of hydrogen; hydroxy; SO$_2 R^d$; $C_{1-6}$ alkyl optionally substituted with one or more substituents independently selected from halogen, hydroxy, $C_{1-5}$ alkoxy, nitro, and $N(R^e)_2$; $C_{1-6}$ alkoxy optionally substituted with one or more substituents independently selected from halogen, hydroxy, $C_{1-5}$ alkoxy, nitro and $N(R^e)_2$; aryl optionally substituted with one or more substituents independently selected from halogen, hydroxy, $C_{1-4}$ alkyl, $C_{1-5}$ alkoxy, nitro, and $N(R^e)_2$; and heteroaryl optionally substituted with one or more substituents independently selected from halogen, hydroxy, $C_{1-4}$ alkyl, $C_{1-5}$ alkoxy, nitro, and $N(R^e)_2$;

$R^d$ is selected from the group consisting of hydrogen; $N(R^e)_2$; $C_{1-6}$ alkyl optionally substituted with one or more substituents independently selected from halogen, hydroxy, $C_{1-5}$ alkoxy, nitro, and $N(R^e)_2$; aryl and heteroaryl;

$R^e$ is hydrogen or $C_{1-6}$ alkyl; and $R^f$ and $R^g$ are independently selected from the group consisting of hydrogen; hydroxy; SO$_2 R^d$; $C_{1-6}$ alkyl substituted with one or more substituents independently selected from halogen, hydroxy, $C_{1-5}$ alkoxy, nitro, and $N(R^e)_2$; $C_{1-6}$ alkoxy optionally substituted with one or more substituents independently selected from halogen, hydroxy, $C_{1-5}$ alkoxy, nitro and $N(R^e)_2$; aryl optionally substituted with one or more substituents independently selected from halogen, hydroxy, $C_{1-4}$ alkyl, $C_{1-5}$ alkoxy, nitro, and $N(R^e)_2$; and heteroaryl optionally substituted with one or more substituents independently selected from halogen, hydroxy, $C_{1-4}$ alkyl, $C_{1-5}$ alkoxy, nitro, and $N(R^e)_2$.

In certain embodiments, when AR is aryl substituted with $C_{1-6}$alkyl, the $C_{1-6}$alkyl moiety is substituted. In certain exemplary embodiments, the substituents are independently selected from halogen, hydroxy, $C_{1-5}$ alkoxy, nitro and $N(R^e)_2$.

Non-limiting examples of compounds of this subgroup include:

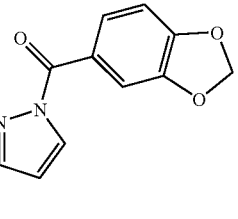

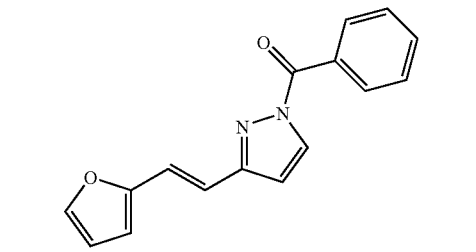

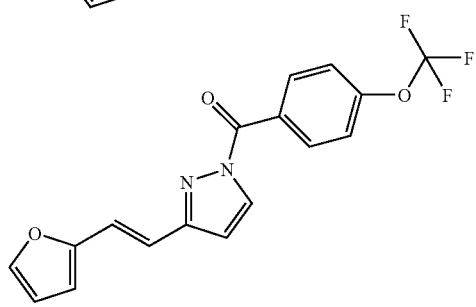

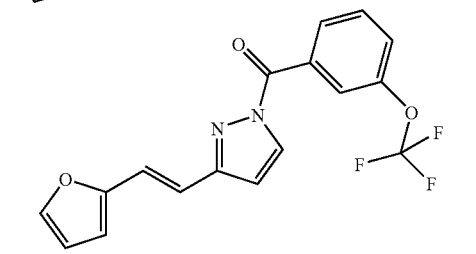

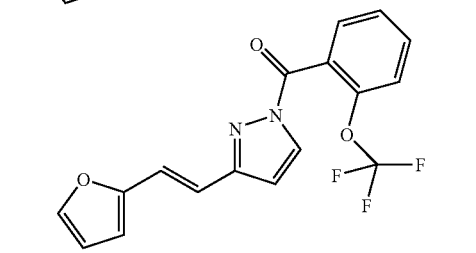

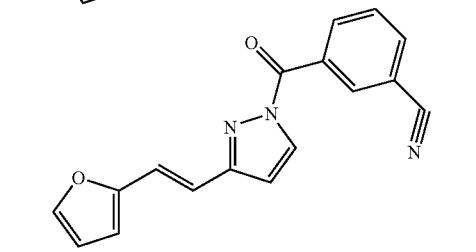

-continued

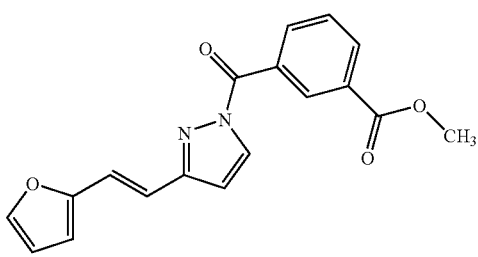

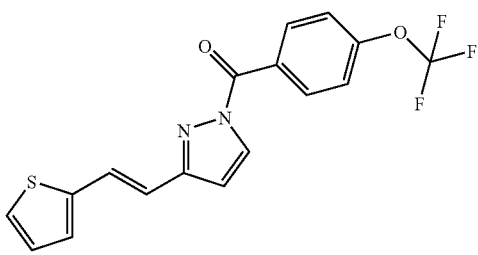

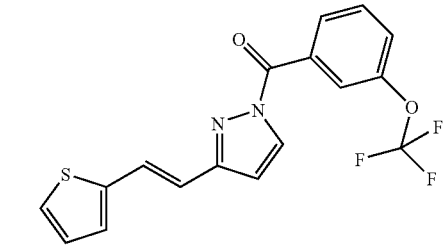

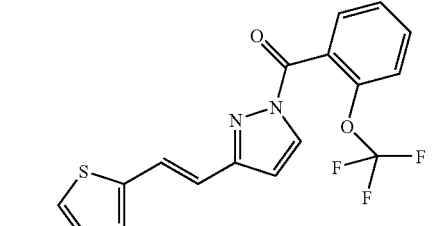

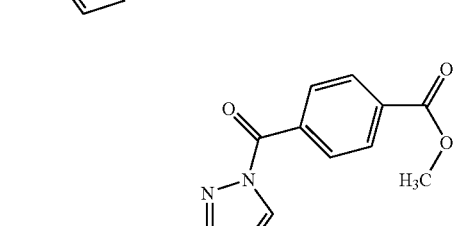

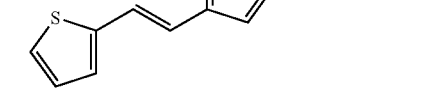

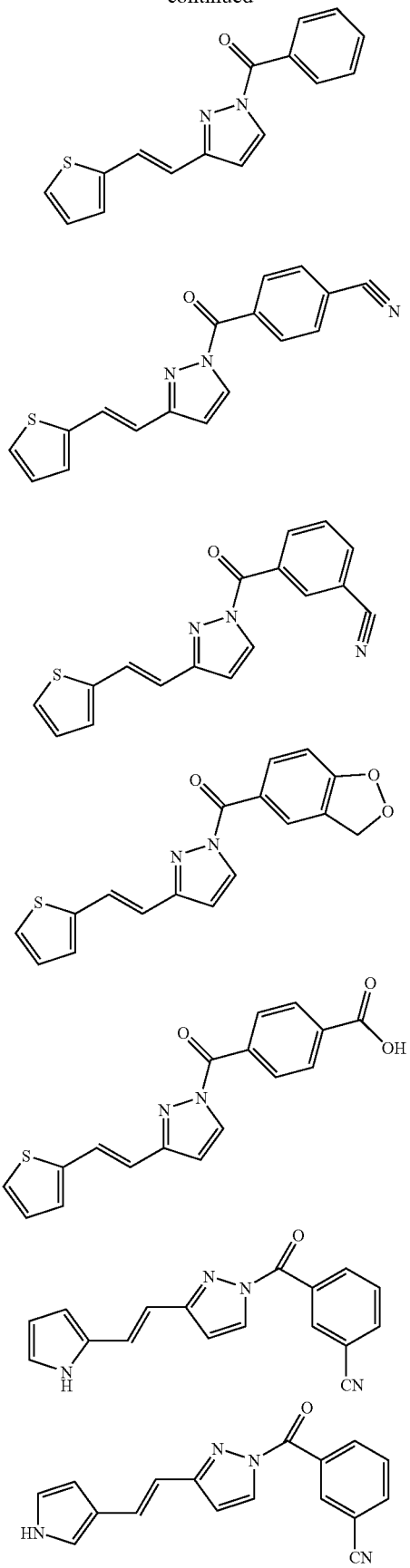

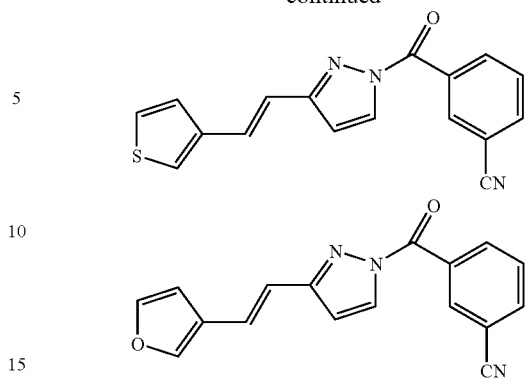

It will be appreciated that each of the compounds described herein and each of the subclasses of compounds described above may be substituted as described generally herein, or may be substituted according to any one or more of the subclasses described above and herein [e.g., i)-liv)].

Some of the foregoing compounds can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided.

In another embodiment, the invention is directed to the use for any one or more of the aforementioned purposes of compounds that activate HGF/SF pathways with the general formula (IV):

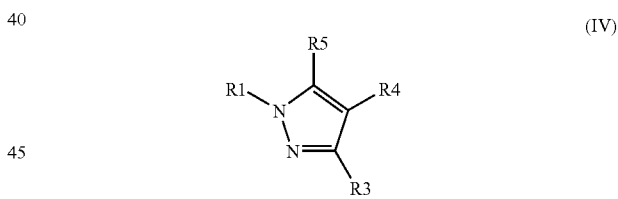

(IV)

wherein R3 and R5 are independently or together a straight-chain or branched $C_1$-$C_6$ alkyl optionally substituted with a cyano or halogen, halogen, trifluoromethyl or difluoromethyl groups;

R1 is hydrogen, methyl, CO-Aryl, $SO_2$-Aryl, CO-heteroaryl, or CO-alkyl; and

R4 is $CH_2$-Aryl, halogen, arylcarbonylvinyl or S-heteroaryl.

R3 and R5 preferably may be methyl, t-butyl or chloro groups. The aryl group of substituent R1 is preferably an aromatic group such as phenyl, naphthyl, or biphenyl, substituted with one or more halogen, $C_1$ to $C_4$ alkyl or $C_1$ to $C_4$ alkyloxy groups. The heteroaryl group of substituent R1 preferably is a 3-aryl-substituted isoxazole or 3-aryl-substituted thienyl group. The alkyl group of substituent R1 preferably is t-butyl, or a C1-C6 straight, branched or cycloalkyl group. In a most preferred embodiment, R3 is methyl, R5 is chloro, R1 is methyl, and R4 is 4-chlorophenylcarbonylvinyl group.

Non-limiting example of modulators of HGF/SF activity of Formula (IV) useful for the purposes described herein include the following compounds:

3-(5-chloro-1,3-dimethyl-1H-pyrazol-4-yl)-1-(4-chlorophenyl)prop-2-en-1-one
[4-(2,6-dichlorobenzyl)-3,5-dimethyl-1H-pyrazol-1-yl][3-(2,6-dichlorophenyl)-5-methylisoxazol-4-yl]methanone
(4-(2-chloro-6-fluorobenzyl)-3,5-dimethyl-1H-pyrazole-1-yl)(3-(2,6-dichlorophenyl)-5-methylisoxazol-4-yl)methanone
4-(2-chloro-6-fluorobenzyl)-1-((3,4-dichlorophenyl(sulfonyl)-3,5-dimethyl-1H-pyrazole
4-(2-chloro-6-fluorobenzyl)-1,3,5-trimethyl-1H-pyrazole
4-(2-chloro-6-fluorobenzyl)-3,5-dimethyl-1H-pyrazole
(4-bromo-3,5-dimethyl-1H-pyrazol-1-yl)(3-(2,6-dichlorophenypisoxazole-4-carbohydrazide)
3-(4-(2,6-dichlorobenzyl)-3,5-dimethyl-1H-pyrazol-1-yl)propanenitrile
3,5-di(tert-butyl)-4-(2-chloro-6-fluorobenzyl)-1H-pyrazole
(4-(2-chloro-6-fluorobenzyl)-3,5-dimethyl-1H-pyrazole-1-yl)(2,6-dichlorophenyl)methanone
1-(4-(2-chloro-6-fluorobenzyl)-3,5-dimethyl-1H-pyrazole-1-yl)2,2-dimethylpropan-1-one
(4-(2-chloro-6-fluorobenzyl)-3,5-dimethyl-1H-pyrazole-1-yl)(4-chlorophenyl)methanone
(4-(2-chloro-6-fluorobenzyl)-3,5-dimethyl-1H-pyrazole-1-yl)(2-thienyl)methanone; and
(4-chlorophenyl)(3,5-dimethyl-4-((1-methyl-1H-imidazol-2-ypthio)-1H-pyrazol-1-yl)methanone.

In yet another embodiment, the invention is directed to the use for any one or more of the afore-mentioned purposes of compounds that modulate HGF/SF activity with the general formula (V):

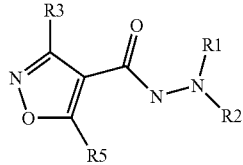

wherein R5 is a $C_1$ to $C_6$ branched or straight-chained alkyl group;
R3 is a substituted or unsubstituted Aryl group;
R1 is hydrogen or a $C_1$ to $C_4$ straight-chained, branched or cycloalkyl group;
R2 is COCH$_2$ONCH-Aryl; heteroaryl, COCH$_2$CH$_2$Aryl; Aryl; COS-Aryl; CO-Heteroaryl; $C_1$ to $C_4$ straight-chained alkyl, branched alkyl, or cycloalkyl; or wherein R1 and R2 form a cyclic group of 5 or 6 carbon atoms.

Preferably, R5 is methyl. R3 is preferably an alkyl-, halogen- or alkyloxy-substituted phenyl group such as 2,6-dichlorophenyl. R1 is preferably hydrogen or methyl. R2 is preferably a substituted pyridyl group such as 2-(6-trifluoromethyl)pyridyl, a substituted arylthiocarbonyl group such as 2-(nitrophenyl)thiocarbonyl, or a 4-aryl-substituted-5-methylisoxazonecarbonyl group.

Non-limiting examples of compounds of Formula (V) include:
N'4,5-dimethyl-N'4-(5-nitro-2-pyridyl)-3-(2,6-dichlorophenypisoxazole-4-carbohydrazide
N'4-(2-(((2,4-dichlorobenzylidene)amino)oxy)acetyl)-3-(2,6-dichlorophenyl)-5-methylisoxazole-4-carbohydrazide
N'4-(3-(3,4,5-trimethoxyphenyl)propanoyl)-3-(2,6-dichlorophenyl)-5-methylisoxazole-4-carbohydrazide
2-nitrophenyl 2-((3-(2,6-dichlorophenyl)-5-methylisoxazol-4-yl)carbonyphydrazine-1-carbothioate
N'4-((2-methyl-1,3-thiazol-4-4yl)carbonyl)-3-(2,6-dichlorophenyl)-5-methylisoxazole-4-4carbohydrazide
N1-((2-((3-(2,6-dichlorophenyl)-5-methylisoxazol-4-yl)carbonyl)hydrazino)(methylthio)methylidene)benzene-1-sulfonamide
N'4-(2,4,6-trichlorophenyl)-3-3(2,6-dichlorophenyl)-5-methylisoxazole-4-carbohydrazide
N'4,3-di(2,6-dichlorophenyl)-5-methylisoxazole-4-carbohydrazide
N'4-(3,5-dichloro-4-pyridyl)-3-(2,6-dichlorophenyl)-5-methylisoxazole-4-carbohydrazide
N'4-phenyl-3-(2,6-dichlorophenyl)-5-methylisoxazole-4-carbohydrazide
N'4,N'4,5-trimethyl-3-(2,6-dichlorophenyl)isoxazole-4-carbohydrazide
N4-azepan-1-yl-3-(2,6-dichlorophenyl)-5-methylisoxazole-4-carboxamide
N'4-(6-(trifluoromethyl)-2-pyridyl)-3-(2,6-dichlorophenyl)-5-methylisoxazole-4-carbohydrazide; and
N'4-(3,3-diethoxypropanoyl)-3-(2,6-dichlorophenyl)-5-methylisoxazole-4-carbohydrazide.

In still a further embodiment, the invention is directed to the use for the aforementioned purposes of compounds that modulate HGF/SF activity with the general formula (VI):

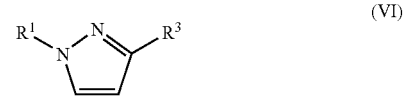

wherein $R^1$ is SO$_2$Alkyl, SO$_2$-Aryl, CO-t-Butyl, COAryl, CONHAlkyl; CONHAryl; and
$R^3$ is CHCH-heteroaryl; phenoxyphenyl; heteroaryl; or Aryl substituted heteroaryl.

Preferably, $R^1$ may be SO$_2$Alkyl, wherein Alkyl is $C_1$ to $C_4$ straight-chained, branched or cyclo, most preferably SO$_2$CH$_3$; SO$_2$-Aryl, wherein Aryl is halo, $C_{1-4}$ alkyl or alkyloxy substituted phenyl; COAlkyl, wherein alkyl is $C_1$ to $C_6$ straight-chained alkyl, branched alkyl or cycloalkyl, most preferably CO-t-Butyl ; COAryl wherein Aryl is phenyl substituted with halo, C1-C4 alkyl or alkyloxy; CONHAlkyl wherein alkyl is $C_1$ to $C_6$ straight-chained alkyl, branched alkyl or cycloalkyl, most preferably CONHCH$_3$; or CONHAryl, wherein aryl is phenyl substituted with halo, $C_1$ to $C_4$ alkyl or $C_1$ to $C_4$ alkyloxy. R3 may be CHCH-heteroaryl, where in heteroaryl includes but is not limited to both cis and trans CHCH-3-thienyl, CHCH-2-furyl and CHCH-3-furyl, and substituted CHCH-thienyl and CHCH-furyl, most preferably CHCH-2-thienyl; phenoxyphenyl; heteroaryl; or aryl substituted heteroaryl.

Non-limiting examples of compounds of Formula (VI) include:
(4-chlorophenyl)[3-(2-(2-thienyl)vinyl)-1H-pyrazol-1-yl]methanone;
1-(methylsulfonyl)-3-(2-(2-thienypvinyl)-1H-pyrazole
2,2-dimethyl-1-(3-(2-(2-thienypvinyl)-1H-pyrazol-1-yl)propan-1-one N-methyl-3-(2-(2-thienyl)vinyl)-1H-pyrazole-1-carboxamide
(4-chlorophenyl)(3-(3-phenylisoxazol-5-yl)-1H-pyrazol-1-yl)methanone
(4-chlorophenyl)(3-(3-(4-chlorophenyl)-5-methylisoxazol-4-yl)-1H-pyrazol-1-yl)methanone
(4-chlorophenyl)(3-(5-(2-thienyl)-2-thienyl)-1H-pyrazol-1-yl)methanone
(2,4-dichlorophenyl)(3-(5-(2,4-difluorophenyl)-2-furyl)-1H-pyrazol-1-yl)methanone
N1-phenyl-3-(2-(2-thienypvinyl)-1H-pyrazole-1-carboxamide
(4-chlorophenyl)(3-(2-(5-(2-thienyl)-2-thienyl)-4-methyl-1,3-thiazol-5-yl)-1H-pyrazol-1-yl)methanone
(3-benzhydryl-1H-pyrazol-1-yl)(4-chlorophenypmethanone
N1-(4-chlorophenyl)-3-(2-(2-thienypvinyl)-1H-pyrazole-1-carboxamide
(4-chlorophenyl)(3-(2-methylimidazo(1,2-a)pyridin-3-yl)-1H-pyrazol-1-yl)methanone
2-chloro-6-(4-(1-(4-chlorobenzyl)-1H-pyrazol-3-y0phenoxy)benzonitrile; and
1((4-chlorophenypsulfonyl)-3-(2-(2-thienypvinyl)-1H-pyrazole.

In a further embodiment, the invention is directed to the use for any one or more of the aforementioned purposes of compounds that modulate HGF/SF activity with the general formula (VII):

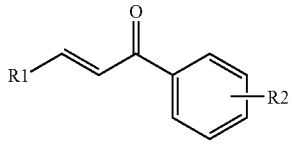

(VII)

wherein R1 is Aryl or Heteroaryl; and
R2 is one or more halogen, nitro, $C_1$ to $C_4$ straight-chained alkyl, branched alkyl, or cycloalkyl, or $C_i$ to $C_4$ alkyloxy groups.

The definitions of the aforementioned substituents are described hereinabove. Preferably, R1 is a phenyl group substituted with one or more halogen, $C_1$ to $C_4$ alkyl, or $C_1$ to $C_4$ allcyloxy groups, or a heteroaryl, most preferably 4-bromo-2-thienyl, 4-pyridyl, 2-furyl, 3-thienyl, substituted with halogens and/or $C_1$ to $C_4$ alkyl. R2 preferably is halogen (F, Cl, Br), nitro, or a $C_1$ to $C_4$ straight-chained alkyl, branched alkyl, or cycloalkyl group or a $C_1$ to $C_4$ alkyloxy group; most preferably, R2 is a methyl group and a chloro group.

Non-limiting examples of modulators of Formula (VII) include:
1-(4-chloro-3-methylphenyl)-3-(2,6-dichlorophenyl)-prop-2-en-1-one
1-(4-chloro-3-methylphenyl)-3-(2-chlorophenyl)prop-2-en-1-one
3-(2-chloro-6-fluorophenyl)-1-(4-chloro-3-methylphenyl)prop-2-en-1-one
3-(4-bromo-2-thienyl)-1-(3,4-dichlorophenyl)prop-2-en-1-one
3-(4-bromo-2-thienyl)-1-(4-chloro-3-methylphenyl)prop-2-en-1-one
3-(4-bromo-2-thienyl)-1-(4-fluorophenyl)prop-2-en-1-one
3-(4-bromo-2-thienyl)-1-(4-chlorophenyl)prop-2-en-1-one
1-(4-chlorophenyl)-3-(2,4-dichlorophenyl)prop-2-en-1-one
3-(1,3-benzodioxol-5-yl)-1-(4-bromophenyl)prop-2-en-1-one
3-(3-phenoxy-2-thienyl)-1-(2-thienyl)prop-2-en-1-one
3-(3-bromo-4-methoxyphenyl)-1-phenylprop-2-en-one
3-(3,4-dichlorophenyl)-1-(2-nitrophenyl)prop-2-en-1-one
1-(4-chlorophenyl)-3-(3,4-dichlorophenyl)prop-2-en-1-one
1-(4-chlorophenyl)-3-(3,5-dichloro-2-hydroxyphenyl)prop-2-en-1-one
1-(2-chlorophenyl)-3-(3,5-dichloro-2-hydroxyphenyl)prop-2-en-1-one
3-(4-chlorophenyl)-1-(2,6-dichlorophenyl)prop-2-en-1-one
1-(4-bromophenyl)-3-(4-chlorophenyl)prop-2-en-1-one
1-(2-chlorophenyl)-3-(2,6-dichlorophenyl)prop-2-en-1-one
1-(4-chlorophenyl)-3-(2,6-dichlorophenyl)prop-2-en-1-one
3-(2,6-dichlorophenyl)-1-(4-methoxyphenyl)prop-2-en-1-one
3-(4-chloro-1-methyl-1H-pyrazol-3-yl)-1-[4-(trifluoromethyl)phenyl]prop-2-en-1-one
3-(2,4-dichlorophenyl)-1-(2-methylphenyl)prop-2-en-1-one
3-(2,6-dichlorophenyl)-1-(2-methylphenyl)prop-2-en-1-one
3-(3,4-dichlorophenyl)-1-(2-methylphenyl)prop-2-en-1-one
3-(5-bromo-2-hydroxyphenyl)-1-(3-methylphenyl)prop-2-en-1-one
3-(5-bromo-2-hydroxyphenyl)-1-(4-methylphenyl)prop-2-en-1-one
3-(2,4-dichlorophenyl)-1-(3-methylphenyl)prop-2-en-1-one
3-(2,4-dichlorophenyl)-1-(4-methoxyphenyl)prop-2-en-1-one
1-[4-amino-2-(methylthio)-1,3-thiazol-5-yl]-3-(4-chlorophenyl)prop-2-en-1-one
1-(4-chlorophenyl)-3-[4-(trifluoromethyl)phenyl]prop-2-en-1-one
1-benzo[b]thiophen-3-yl-3-(4-chlorophenyl)prop-2-en-1-one
1,3-di(5-nitro-3-thienyl)prop-2-en-1-one
1-(4-bromophenyl)-3(3,5-difluorophenyl)prop-2-en-1-one; and
3-(3,5-difluorophenyl)-1-(3-nitrophenyl)prop-2-en-1-one.

In addition to the above, the following compounds are also activators of HGF pathways useful for the purposes herein:
1-(methylsulfonyl)-5-(2-(2-thienyl)vinyl)-1H-pyrazole
2,2-dimethyl-1-(5-(2-(2-thienyl)vinyl)-1H-pyrazole-1-yl)propan-1-one
N-methy-5-(2-(2thienyl)vinyl)-1H-pyrazole-1-carboxamide
(4-chlorophenyl)(5-(3-phenylisoxazol-5-yl)-1H-pyrazol-1-yl)methanone
(4-chlorophenyl)(5-(5-(2-thienyl)-2-thienyl)-1H-pyrazol-1-yl)methanone
(4-(2-chloro-6-fluorobenzyl)-3,5-dimethyl-1H-pyrazol-1-yl)(4-chlorophenyl)methanone
(4-chlorophenyl)(5-(methylthio)-3-(4-phenoxyphenyl)-1H-pyrazol-1-yl)methanone
(4-chlorophenyl)(3,5-dimethyl-4-((1-methyl-1H-imidazol-2-ypthio)-1H-pyrazol-1-yl)methanone N1-phenyl-5-(2-(2-thienyl)vinyl)-1H-pyrazole-1-carboxamide
(4-chlorophenyl)(5-(2-(5-(2-thienyl)-2-thienyl)-4-methyl-1,3-thiazol-5-yl)-1H-pyrazol-1-yl)methanone
(5-benzhydryl-1H-pyrazol-1-yl)(4-chlorophenyl)methanone
N1-(4-chlorophenyl)-5-(2-(2-thienyl)vinyl)-1H-pyrazole-1-carboxamide
methyl 1-(4-chlorobenzoyl)-5-isoxazol-5-yl-3-methyl-1H-pyrazole-4-carboxylate
2-chloro-6-(4-(1-(4-chlorobenzyl)-1H-pyrazol-5-yl)phenoxy)benzonitrile
4(5-chlorobenzo(b)thiophen-3-yl)-1-(2chlorophenyl)sulfonyl)-3,5dimethyl-1-H-pyrazole
4-(2,6-dichlorobenzyl)-3-methyl-1-phenyl-1H-pyrazol-5-ol
3-methyl-4-(2-methylallyl)-1-(phenylsulfonyl)-1H-pyrazol-5-ol
[3-(2,6-difluorophenyl)-4-ethyl-1H-pyrazol-1-yl](2-thienyl)methanone
4-[(5-chloro-1-benzothiophen-3-yl)methyl]-N,3,5-trimethyl-1H-pyrazole-1-carboxamide
3-(2,6-difluorophenyl)-4-ethyl-1H-pyrazole
N1-(3-chlorophenyl)-4-[(5-chlorobenzo[b]thiophen-3-yl)methyl]-3,5-dimethyl-1H-pyrazole-1-carboxamide
{4-[(5-chlorobenzo[b]thiophen-3-yl)methyl]-3,5-dimethyl-1H-pyrazol-1-yl}(4-nitrophenyl)methanone
N1-phenyl-4-[(5-chlorobenzo[b]thiophen-3-yl)methyl]-3,5-dimethyl-1H-pyrazole-1-carboxamide
4-[(5-chloro-1-benzothiophen-3-yl)methyl]-N-(2,4-dichlorophenyl)-3,5-dimethyl-1H-pyrazole-1-carboxamide
1-[3-(2,6-difluorophenyl)-4-ethyl-1H-pyrazol-1-yl]-2,2-dimethylpropan-1-one
4-(2-chloro-6-fluorobenzyl)-1-{[3,5-di(trifluoromethyl)phenyl]sulfonyl}-3,5-dimethyl-1H-pyrazole
(4-(2-chloro-6-fluorobenzyl)-3,5-dimethyl-1H-pyrazole-1-yl)(3-(2,6-dichlorophenyl)-5-methylisoxazol-4-yl)methanone
4-(2-chloro-6-fluorobenzyl)-1-((3,4-dichlorophenyl)sulfonyl)-3,5-dimethyl-1H-pyrazole
4-(2-chloro-6-fluorobenzyl)-1,3,5-trimethyl-1H-pyrazole
4-(2-chloro-6-fluorobenzyl)-3,5-dimethyl-1H-pyrazole
(4-bromo-3,5-dimethyl-1H-pyrazol-1-yl)(3-(2,6-dichlorophenyl)isoxazole-4-carbohydrazide)
N'4,5-dimethyl-N'4-(5-nitro-2-pyridyl)-3-(2,6-dichlorophenyl)isoxazole-4-carbohydrazide
N'4-(2-(((2,4-dichlorobenzylidene)amino)oxy)acetyl)-3-(2,6-dichlorophenyl)-5-methylisoxazole-4-carbohydrazide
3-(2,6-dichlorophenyl)-5-methylisoxazole-4-carbohydrazide
N'4-(3-(3,4,5-trimethoxyl)phenyl)propanoyl)-3-(2,6-dichlorophenyl)-5-methylisoxazole-4-carbohydrazide
2-nitrophenyl 2-((3-(2,6-dichlorophenyl)-5-methylisoxazol-4-yl)carbonyl)hydrazine-1-carbothioate
1-((4-chlorophenyl)sulfonyl)-4-(2,6-dichlorobenzyl)-3,5-dimethyl-1H-pyrazol
3-(4-(2,6-dichlorobenzyl)-3,5-dimethyl-1H-pyrazol-1-yl)propanenitrile
N'4-((2-methyl-1,3-thiazol-4-4yl)carbonyl)-3-(2,6-dichlorophenyl)-5-methylisoxazole-4-4carbohydrazide
N1-((2-((3-(2,6-dichlorophenyl)-5-methylisoxazol-4-yl)carbonyl)hydrazino)(methylthio)methylidene)benzene-1-sulfonamide
N'4-(2,4,6-trichlorophenyl)-3-3(2,6-dichlorophenyl)-5-methylisoxazole-4-carbohydrazide
N'4,3-di(2,6-dichlorophenyl)-5-methylisoxazole-4-carbohydrazide
3,5-di(tert-butyl)-4-(2-chloro-6-fluorobenzyl)-1H-pyrazole
N'4-(3,5-dichloro-4-pyridyl)-3-(2,6-dichlorophenyl)-5-methylisoxazole-4-carbohydrazide
N'4-phenyl-3-(2,6-dichlorophenyl)-5-methylisoxazole-4-carbohydrazide
(4-(2-chloro-6-fluorobenzyl)-3,5-dimethyl-1H-pyrazole-1-yl)(2,6-dichlorophenyl)methanone
1-(4-(2-chloro-6-fluorobenzyl)-3,5-dimethyl-1H-pyrazole-1-yl)2,2-dimethylpropan-1-one
N'4,N'4,5-trimethyl-3-(2,6-dichlorophenyl)isoxazole-4-carbohydrazide
N4-azepan-1-yl-3-(2,6-dichlorophenyl)-5-methylisoxazole-4-carboxamide
N'4-(6-(trifluoromethyl)-2-pyridyl)-3-(2,6-dichlorophenyl)-5-methylisoxazole-4-carbohydrazide
(4-(2-chloro-6-fluorobenzyl)-3,5-dimethyl-1H-pyrazole-1-yl)(4-chlorophenyl)methanone
N'4-(3,3-diethoxypropanoyl)-3-(2,6-dichlorophenyl)-5-methylisoxazole-4-carbohydrazide
(4-(2-chloro-6-fluorobenzyl)-3,5-dimethyl-1H-pyrazole-1-yl)(2-thienyl)methanone
Tetraphenylthiophene
Pentaphenylbenzene
1,3,5-triphenylbenzene
(3-Biphenyl)Trimethyl silane
16 methyl-16 Dehydropregnenolone
9-biphenyl-4-ylmethylene-9H-tri-benzo(A,C,E)-cycloheptene
1,1,3-triphenylinedene
9,9-Biphenanthrene
N-(furfurylidene)-2,4-xylidine
1-(4-Chloro-3 Methyl Phenyl)3-2(2,6-dichlorophenyl) Prop-2-ene-1-one
3-(4-Bromophenyl)-1-phenylprop-2-en-1-one
8-Benzyledene -2,4 Diphenyl-5,6,7,8 Tetrahydrophosphinoline
6-(3,5-Dimethylphenyl)Thio)-3-Phenyl(1,2,4-Triazolo(4,3-b)pyridazine
3,3-dibromo-1-phenyl-1,2,3,4-tetrahydroquinoline-2,4-dione
4-(4-chlorophenyl)-6-(dimethylamino)-2-phenyl-5-pyrimidinecarbonitrile In other certain embodiments, the invention is also directed to the use for the purposes described herein of the following compounds and pharmaceutical compositions comprising compounds of the general Formula (VIII) as further defined below:

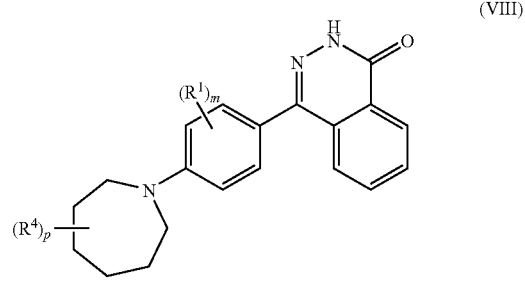

(VIII)

or pharmaceutically acceptable derivative thereof;

wherein m is an integer from 1 to 4;

p is an integer from 1 to 6;

each occurrence of $R^1$ and $R^4$ is independently hydrogen, halogen, hydroxyl, —$NO_2$, —$NH_2$, —CN, an optionally substituted aliphatic, alicyclic, heteroaliphatic, heterocyclic, aromatic or heteroaromatic moiety, —$OR^R$, —$S(=O)_nR^d$, —$NR^bR^c$, —$C(=O)R^a$, —$OPO_2OR^a$ or —$C(=O)OR^a$; wherein n is 0-2, $R^R$ is an optionally substituted aliphatic, alicyclic, heteroaliphatic, heterocyclic, aromatic, heteroaromatic or acyl moiety;

$R^a$, for each occurrence, is independently selected from the group consisting of hydrogen and an optionally substituted aliphatic, alicyclic, heteroaliphatic, heterocyclic, aromatic, or heteroaromatic moiety;

$R^b$ and $R^c$, for each occurrence, are independently selected from the group consisting of hydrogen; hydroxy; $SO_2R^d$; and aliphatic, alicyclic, heteroaliphatic, heterocyclic, aromatic, heteroaromatic or acyl moiety;

$R^d$, for each occurrence, is independently selected from the group consisting of hydrogen; —$N(R^e)_2$; aliphatic, alicyclic, heteroaliphatic, heterocyclic, aromatic or heteroaromatic; and $R^e$, for each occurrence, is independently hydrogen or aliphatic.

In certain other embodiments, compounds of formula (VIII) are defined as follows:

m is an integer from 1 to 4;

p is an integer from 1 to 6;

each occurrence of $R^1$ and $R^4$ is independently hydrogen, halogen, hydroxyl, —$NO_2$, —$NH_2$, —CN, an optionally substituted alkyl, heteroalkyl, cycloalkyl, heterocyclic, aryl or heteroaryl moiety, —$OR^R$, —$S(=O)_nR^d$, —$NR^bR^c$, —$C(=O)R^a$, —$OPO_2OR^a$ or —$C(=O)OR^a$; wherein n is 0-2, $R^R$ is an optionally substituted alkyl, heteroalkyl, cycloalkyl, heterocyclic, aryl, heteroaryl or acyl moiety;

$R^a$, for each occurrence, is independently hydrogen or an optionally substituted alkyl, heteroalkyl, cycloalkyl, heterocyclic, aryl or heteroaryl moiety;

$R^b$ and $R^c$, for each occurrence, are independently hydrogen, hydroxy, $SO_2R^d$, or an alkyl, heteroalkyl, cycloalkyl, heterocyclic, aryl, heteroaryl or acyl moiety;

$R^d$, for each occurrence, is independently hydrogen, —$N(R^e)_2$, alkyl, heteroalkyl, cycloalkyl, heterocyclic, aryl or heteroaryl; and $R^e$, for each occurrence, is independently hydrogen or alkyl.

In another aspect, the invention is directed to the use for the purposes described herein of the following compounds and pharmaceutical compositions comprising compounds of formula (XI):

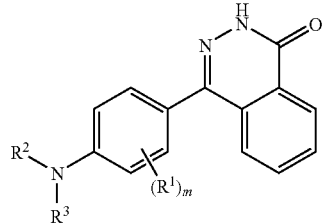

(XI)

or pharmaceutically acceptable derivatives thereof;

m is an integer from 1 to 4;

each occurrence of $R^1$ is independently hydrogen, halogen, hydroxyl, —$NO_2$, —$NH_2$, —CN, an optionally substituted aliphatic, alicyclic, heteroaliphatic, heterocyclic, aromatic or heteroaromatic moiety, —$OR^R$, —$S(=O)_nR^d$, —$NR^bR^c$, —$C(=O)R^a$, —$OPO_2OR^a$ or —$C(=O)OR^a$; wherein n is 0-2, $R^R$ is an optionally substituted aliphatic, alicyclic; heteroaliphatic, heterocyclic, aromatic, heteroaromatic or acyl moiety;

$R^2$ and $R^3$ are independently hydrogen, hydroxyl, —$NH_2$, an optionally substituted aliphatic, heteroaliphatic, alicyclic, heterocyclic, aromatic or heteroaromatic moiety, —$OR^R$, —$S(=O)_nR^d$, —$NR^bR^c$, —$C(=O)R^a$ or —$C(=O)OR^a$; wherein n is 0-2, $R^R$ is an optionally substituted aliphatic, heteroaliphatic, alicyclic, heterocyclic, aromatic or heteroaromatic or acyl moiety; or $R^2$ and $R^3$ taken together with the nitrogen to which they are attached form an optionally substituted heteroaromatic or heterocyclic group comprising 4-10 ring members and 0-3 additional heteroatoms selected from the group consisting of O, N and S; the heteroaromatic or heterocyclic group optionally further substituted with one or more optionally substituted aliphatic, alicyclic, heteroaliphatic, heterocyclic, aromatic, heteroaromatic or acyl groups;

$R^a$, for each occurrence, is hydrogen or an optionally substituted aliphatic, alicyclic, heteroaliphatic, heterocyclic, aromatic, or heteroaromatic moiety;

$R^b$ and $R^c$, for each occurrence, are independently hydrogen, hydroxy, $SO_2R^d$, or an optionally substituted aliphatic, alicyclic, heteroaliphatic, heterocyclic, aromatic, heteroaromatic or acyl moiety;

$R^d$, for each occurrence, is independently hydrogen, —$N(R^e)_2$, or an optionally substituted aliphatic, alicyclic, heteroaliphatic, heterocyclic, aromatic or heteroaromatic moiety; and $R^e$, for each occurrence, is independently hydrogen or aliphatic.

In certain other embodiments, compounds of formula (XI) are defined as follows:

m is an integer from 1 to 4;

each occurrence of $R^1$ is independently hydrogen, halogen, hydroxyl, —$NO_2$, —$NH_2$, —CN, an optionally substituted alkyl, heteroalkyl, cycloalkyl, heterocyclic, aryl or heteroaryl moiety, —$OR^R$, —$S(=O)_nR^d$, —$NR^bR^c$, —$C(=O)R^a$, —$OPO_2OR^a$ or —$C(=O)OR^a$; wherein n is 0-2, $R^R$ is an optionally substituted alkyl, heteroalkyl, cycloalkyl, heterocyclic, aryl, heteroaryl or acyl moiety;

$R^2$ and $R^3$ are independently hydrogen, hydroxyl, —$NH_2$, an optionally substituted alkyl, heteroalkyl, cycloalkyl, heterocyclic, aryl or heteroaryl moiety, —$OR^R$, —$S(=O)_nR^d$, —$NR^bR^c$, —$C(=O)R^a$ or —$C(=O)OR^a$; wherein n is 0-2, $R^R$ is an optionally substituted alkyl, heteroalkyl, cycloalkyl, heterocyclic, aryl, heteroaryl or acyl moiety; or $R^2$ and $R^3$ taken together with the nitrogen to which they are attached form a optionally substituted heteroaryl or heterocyclic group comprising 4-10 ring members and 0-3 additional heteroatoms selected from the group consisting of O, N and S; the heteroaryl or heterocyclic group optionally further substituted with one or more optionally substituted alkyl, cycloalkyl, heteroalkyl, heterocyclic, aryl, heteroaryl or acyl groups;

wherein $R^a$, for each occurrence, is independently hydrogen or an optionally substituted alkyl, heteroalkyl, cycloalkyl, heterocyclic, aryl or heteroaryl moiety;

$R^b$ and $R^c$, for each occurrence, are independently hydrogen, hydroxy, $SO_2R^d$, or an alkyl, heteroalkyl, cycloalkyl, heterocyclic, aryl, heteroaryl or acyl moiety;

$R^d$, for each occurrence, is independently hydrogen, $-N(R^e)_2$, alkyl, heteroalkyl, cycloalkyl, heterocyclic, aryl or heteroaryl; and $R^e$, for each occurrence, is independently hydrogen or alkyl.

In certain embodiments, the present invention defines certain classes of compounds which are of special interest for the uses and methods described herein. For example, one class of compounds of special interest includes those compounds having the structure of formula ($IX^A$) in which the compound has the structure:

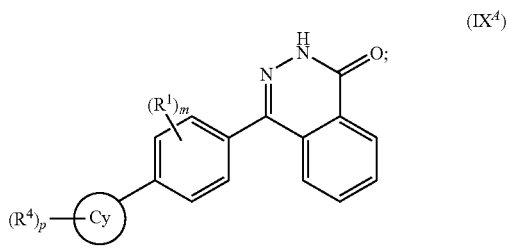

wherein m, p, $R^1$ and $R^4$ are as defined in classes and subclasses herein; and Cy is an optionally substituted N-linked 5- to 10-membered heterocyclic group.

Another class of compounds of special interest includes those compounds having the structure of formula ($IX^B$) in which the compound has the structure:

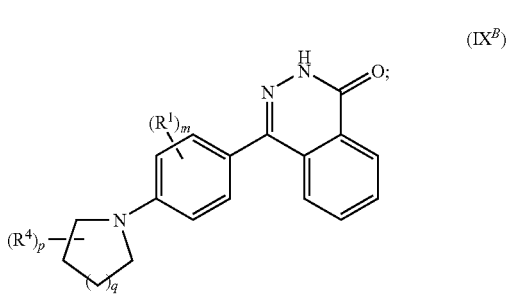

wherein m, p, $R^1$ and $R^4$ are as defined in classes and subclasses herein; and q is an integer selected from 1, 2 or 4.

For the uses and methods described herein, a number of important subclasses of each of the foregoing classes of compounds of formulae (VIII), (IX) and (XI) deserve separate mention; these subclasses include subclasses of the foregoing classes in which:

i) each occurrence of $R^1$ is independently hydrogen, halogen, hydroxyl, $-NO_2$, $-NH_2$, $-CN$, an optionally substituted alkyl, heteroalkyl, cycloalkyl, heterocyclic, aryl or heteroaryl moiety, $-OR^R$, $-S(=O)_nR^d$, $-NR^bR^c$, $-C(=O)R^a$, $-OPO_2OR^a$ or $-C(=O)OR^a$; wherein n is 0-2, $R^R$ is an optionally substituted alkyl, heteroalkyl, cycloalkyl, heterocyclic, aryl, heteroaryl or acyl moiety; wherein $R_a$ is as defined in subset lxvi) below;

ii) at least one occurrence of $R^1$ is hydrogen;

iii) at least one occurrence of $R^1$ is $-NO_2$;

iv) at least one occurrence of $R^1$ is $-NH_2$;

v) at least one occurrence of $R^1$ is $-COOH$, $-C(=O)OCH_3$, $-COCH_3$, $-CONH_2$, $-SO_2OH$, $-SO_2CH_3$, $-SO_2CF_3$, $-OPO_2OH$, $-NHC(=O)CH_3$, $-NHC(=O)CF_3$, $-NHC(=O)CH_3$, $-NHC(=O)CF_3$, $-NHSO_2CH_3$ or $-NHSO_2CF_3$.

vi) at least one occurrence of $R^1$ is halogen;

vii) at least one occurrence of $R^1$ is an optionally substituted N-linked heterocyclic group;

viii) at least one occurrence of $R^1$ is an optionally substituted N-pyrrolyl group;

ix) at least one occurrence of $R^1$ is an aliphatic moiety;

x) at least one occurrence of $R^1$ is an alkyl moiety;

xi) at least one occurrence of $R^1$ is a lower alkyl moiety;

xii) m is 1 and at least one occurrence of $R^1$ is ortho to the bond to the phthalazinone ring;

xiii) m is 1 and at least one occurrence of $R^1$ is meta to the bond to the phthalazinone ring;

xiv) each occurrence of $R^1$ is independently hydrogen, $-NO_2$, $-NH_2$, $-COOH$, $-C(=O)OCH_3$, $-COCH_3$, $-CONH_2$, $-SO_2OH$, $-SO_2CH_3$, $-SO_2CF_3$, $-OPO_2OH$, $-NHC(=O)CH_3$, $-NHC(=O)CF_3$, $-NHSO_2CH_3$, $-NHSO_2CF_3$, halogen, an optionally substituted N-linked heterocyclic group or an aliphatic moiety;

xv) each occurrence of $R^1$ is independently hydrogen, $-NO_2$, $-NH_2$, $-COOH$, $-C(=O)OCH_3$, $-COCH_3$, $-CONH_2$, $-SO_2OH$, $-SO_2CH_3$, $-SO_2CF_3$, $-OPO_2OH$, $-NHC(=O)CH_3$, $-NHC(=O)CF_3$, $-NHSO_2CH_3$, $-NHSO_2CF_3$, halogen, an optionally substituted N-pyrrolyl group or a lower alkyl moiety;

xvi) $R^2$ and $R^3$ are independently hydrogen, hydroxyl, $-NH_2$, an optionally substituted alkyl, heteroalkyl, cycloalkyl, heterocyclic, aryl or heteroaryl moiety, $-OR^R$, $-S(=O)_nR^d$, $-NR^bR^c$, $-C(=O)R^a$ or $-C(=O)OR^a$; wherein n is 0-2, $R^R$ is an optionally substituted alkyl, heteroalkyl, cycloalkyl, heterocyclic, aryl, heteroaryl or acyl moiety; or $R^2$ and $R^3$ taken together with the nitrogen to which they are attached form a optionally substituted heteroaryl or heterocyclic group comprising 4-10 ring members and 0-3 additional heteroatoms selected from the group consisting of O, N and S; the heteroaryl or heterocyclic group optionally further substituted with one or more optionally substituted alkyl, cycloalkyl, heteroalkyl, heterocyclic, aryl, heteroaryl or acyl groups; wherein $R_a$ is as defined in subset lxvi) below;

xvii) $R^2$ and $R^3$ are independently hydrogen, hydroxyl, $-NH_2$, an optionally substituted alkyl, heteroalkyl, cycloalkyl, heterocyclic, aryl or heteroaryl moiety, $-OR^R$, $-S(=O)_nR^d$, $-NR^bR^c$, $-C(=O)R^a$ or $-C(=O)OR^a$; wherein n is 0-2, $R^R$ is an optionally substituted alkyl, heteroalkyl, cycloalkyl, heterocyclic, aryl, heteroaryl or acyl moiety; wherein $R_a$ is as defined in subset lxvi) below;

xviii) $R^2$ and $R^3$ are independently hydrogen, lower alkyl or aryl;

xix) $R^2$ and $R^3$ are independently hydrogen or lower alkyl;

xx) $R^2$ and $R^3$ are independently a hydrophobic group;

xxi) $R^2$ and $R^3$ are independently an aliphatic group;

xxii) $R^2$ and $R^3$ are independently an unsubstituted aliphatic group;

xxiii) $R^2$ and $R^3$ are independently a cyclic or acyclic $C_{6-12}$alkyl, $C_{6-12}$alkenyl, or $C_{6-12}$alkynyl group;

xxiv) $R^2$ and $R^3$ are independently an unsubstituted cyclic or acyclic $C_{6-12}$alkyl, $C_{6-12}$alkenyl, or $C_{6-12}$alkynyl group;

xxv) $R^2$ and $R^3$ are independently is an -(alkyl)aryl group;

xxvi) $R^2$ and $R^3$ are independently a unsubstituted -(alkyl)aryl group;

xxvii) $R^2$ and $R^3$ taken together with the nitrogen to which they are attached form a optionally substituted heteroaryl or heterocyclic group comprising 4-10 ring members and 0-3 additional heteroatoms selected from the group consisting of O, N and S; the heteroaryl or heterocyclic group optionally further substituted with one or more optionally substituted alkyl, cycloalkyl, heteroalkyl, heterocyclic, aryl, heteroaryl or acyl groups;

xxviii) $R^2$ and $R^3$ taken together with the nitrogen atom to which they are attached form an optionally substituted pyrrolyl, pyrrolidinyl, imidazolyl, imidazolidinyl, pyrazolyl, pyrazolidinyl, 1,2,3-triazolyl, piperidinyl, morpholinyl, thiomorpholinyl, piperazinyl, indolyl, isoindolyl, indolinyl, indazolyl, benzimidazolyl or purinyl moiety;

xxix) $R^2$ and $R^3$ taken together with the nitrogen to which they are attached form an optionally substituted 6-membered heterocyclic group comprising 0-3 additional heteroatoms selected from the group consisting of O, N and S;

xxx) $R^2$ and $R^3$, taken together, represent the hydrophobic portion of an optionally substituted N-linked ring;

xxxi) $R^2$ and $R^3$, taken together, represent the hydrophobic portion of an N-linked ring substituted with hydrophobic groups, such as one or more aliphatic groups;

xxxii) $R^2$ and $R^3$, taken together, represent the hydrophobic portion of an optionally substituted piperidinyl ring;

xxxiii) $R^2$ and $R^3$, taken together, represent the hydrophobic portion of a piperidinyl ring substituted with hydrophobic groups, such as one or more aliphatic groups;

xxxiv) each occurrence of $R^4$ is independently hydrogen, halogen, hydroxyl, $-NO_2$, $-NH_2$, $-CN$, an optionally substituted alkyl, heteroalkyl, cycloalkyl, heterocyclic, aryl or heteroaryl moiety, $-OR^R$, $-S(=O)_nR^d$, $-NR^bR^c$, $-C(=O)R^a$, $-OPO_2OR^a$ or $-C(=O)OR^a$; wherein n is 0-2, $R^R$ is an optionally substituted alkyl, heteroalkyl, cycloalkyl, heterocyclic, aryl, heteroaryl or acyl moiety; wherein $R_a$, $R_b$, $R_c$ and $R_d$ are as defined in subsets lxvi), lxvii) and lxviii) below;

xxxv) at least one occurrence of $R^4$ is hydrogen;

xxxvi) at least one occurrence of $R^4$ is a hydrophobic group;

xxxvii) at least one occurrence of $R^4$ is an optionally substituted aliphatic group;

xxxviii) at least one occurrence of $R^4$ is an unsubstituted aliphatic group;

xxxix) at least one occurrence of $R^4$ is an optionally substituted cyclic or acyclic $C_{6-12}$alkyl, $C_{6-12}$alkenyl, or $C_{6-12}$alkynyl group;

xl) at least one occurrence of $R^4$ is an unsubstituted cyclic or acyclic $C_{6-12}$alkyl, $C_{6-12}$alkenyl, or $C_{6-12}$alkynyl group;

xli) at least one occurrence of $R^4$ is an optionally substituted -(alkyl)aryl group;

xlii) at least one occurrence of $R^4$ is a unsubstituted -(alkyl)aryl group;

xliii) at least one occurrence of $R^4$ is $-NR^bR^c$;

xliv) at least one occurrence of $R^4$ is $-NH_2$;

xlv) at least one occurrence of $R^4$ is $-C(=O)OR^a$; wherein $R_a$ is as defined in subset lxvi) below;

xlvi) at least one occurrence of $R^4$ is $-CO_2H$;

xlvii) p is $\geq 3$ and each occurrence of $R^4$ is independently a cyclic or acyclic $C_{1-6}$alkyl, $C_{2-6}$alcenyl, $C_{2-6}$alkynyl or $-(C_{1-6}$alkyl)aryl group;

xlviii) p is $\geq 3$ and each occurrence of $R^4$ is independently methyl, ethyl, propyl, butyl, pentyl, hexyl, i-propyl or benzyl;

xlix) each occurrence of $R^4$ is independently hydrogen, halogen, an optionally substituted aliphatic group, $-NR^bR^c$, or $-C(=O)OR^a$, wherein $R_a$, $R_b$ and $R_c$ are as defined in subsets lxvi) and lxvii) below;

l) each occurrence of $R^4$ is independently hydrogen, halogen, an optionally substituted cyclic or acyclic $C_{6-12}$alkyl, $C_{6-12}$alkenyl, or $C_{6-12}$alkynyl group, an optionally substituted -(alkyl)aryl group, $-NH_2$ or $-CO_2H$;

li) m is 0;

lii) m is 1;

liii) m is 2;

liv) m is 3;

lv) m is 4;

lvi) p is 0;

lvii) p is 1;

lviii) p is 2;

lix) p is 3;

lx) p is 4;

lxi) p is 5;

lxii) p is 6;

lxiii) q is 1;

lxiv) q is 2;

lxv) q is 4;

lxvi) Ra, for each occurrence, is independently hydrogen or an optionally substituted alkyl, heteroalkyl, cycloalkyl, heterocyclic, aryl or heteroaryl moiety;

lxvii) Rb and Rc, for each occurrence, are independently hydrogen, hydroxy, SO2Rd, or an alkyl, heteroalkyl, cycloalkyl, heterocyclic, aryl, heteroaryl or acyl moiety;

lxviii) Rd, for each occurrence, is independently hydrogen, $-N(Re)2$, alkyl, heteroalkyl, cycloalkyl, heterocyclic, aryl or heteroaryl;

lxix) Re, for each occurrence, is independently hydrogen or alkyl; and/or lxx) Cy is one of:

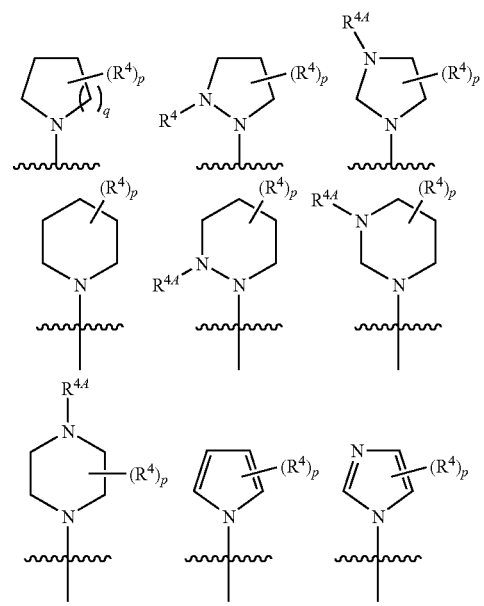

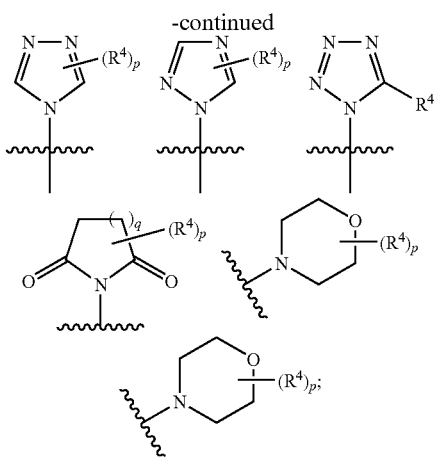

wherein q is 1, 2 or 4 and p and $R^4$ are as defined in classes and subclasses herein, and $R^{4A}$ is hydrogen, hydroxy, $SO_2R^d$, or an alkyl, heteroalkyl, cycloalkyl, heterocyclic, aryl, heteroaryl or acyl moiety; wherein $R^d$ is as defined in classes and subclasses herein.

It will be appreciated that for each of the classes and subclasses described above and herein, any one or more occurrences of groups such as aliphatic, heteroaliphatic, alkyl, heteroalkyl may independently be substituted or unsubstituted, linear or branched, saturated or unsaturated; and any one or more occurrences of alicyclic, heterocyclic, cycloalkyl, aryl, heteroaryl, cycloaliphatic, cycloheteroaliphatic may be substituted or unsubstituted.

The reader will also appreciate that all possible combinations of the variables described in i)-through lxx) above (e.g., $R^1$-$R^4$, m, p and q, among others) are considered part of the invention. Thus, the invention encompasses any and all compounds of formula (VIII), (IX) and (XI), and subclasses thereof, generated by taking any possible permutation of variables $R^1$-$R^4$, m, p and q, and other variables/substituents (e.g., $R_{a-e}$, etc.) as further defined for $R^1$-$R^4$, described in i)-through lxx) above, leading to a stable compound.

As the reader will appreciate, compounds of particular interest for the uses herein include, among others, those which share the attributes of one or more of the foregoing subclasses. Some of those subclasses are illustrated by the following sorts of compounds:

Compounds of the formula (and pharmaceutically acceptable derivatives thereof):

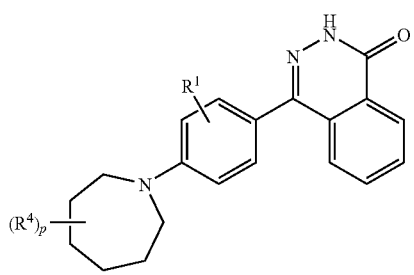

wherein p, $R^1$ and $R^4$ are as defined in classes and subclasses herein. In certain embodiments, p is 1-4 and each occurrence of $R^4$ is independently hydrogen or lower alkyl. In certain embodiments, at least one occurrence of $R^4$ is a hydrophilic group.

Compounds of the formula (and pharmaceutically acceptable derivatives thereof):

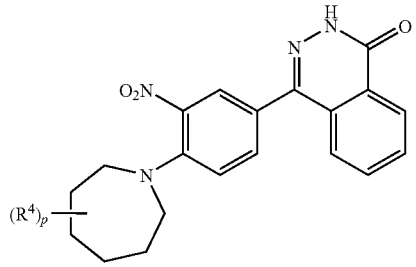

wherein p and $R^4$ are as defined in classes and subclasses herein. In certain embodiments, p is 1-4 and each occurrence of $R^4$ is independently hydrogen or lower alkyl. In certain embodiments, at least one occurrence of $R^4$ is a hydrophilic group.

Compounds of the formula (and pharmaceutically acceptable derivatives thereof):

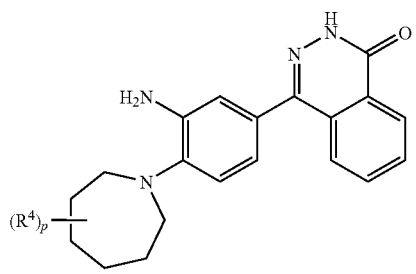

wherein p and $R^4$ are as defined in classes and subclasses herein. In certain embodiments, p is 1-4 and each occurrence of $R^4$ is independently hydrogen or lower alkyl. In certain embodiments, at least one occurrence of $R^4$ is a hydrophilic group.

Compounds of the formula (and pharmaceutically acceptable derivatives thereof):

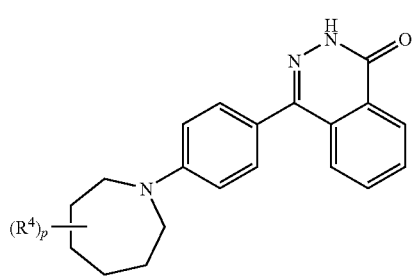

wherein p and $R^4$ are as defined in classes and subclasses herein. In certain embodiments, p is 1-4 and each occurrence of $R^4$ is independently hydrogen or lower alkyl. In certain embodiments, at least one occurrence of $R^4$ is a hydrophilic group.

Compounds of the formula (and pharmaceutically acceptable derivatives thereof):

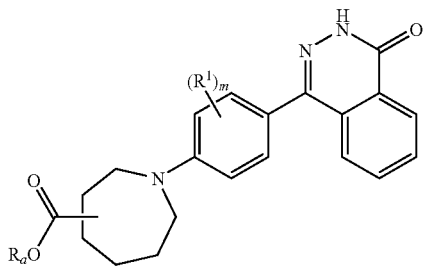

wherein m, $R^1$ and $R_a$ are as defined in classes and subclasses herein. In certain embodiments, $R_a$ is hydrogen. In certain embodiments, $R_a$ is lower alkyl. In certain embodiments, $R_a$ is a hydrophilic group. In certain embodiments, $R_a$ is an optionally substituted cyclic or acyclic $C_{6-12}$alkyl, $C_{6-12}$alkenyl, or $C_{6-12}$alkynyl group. In certain embodiments, $R_a$ is an optionally substituted -(alkyl)aryl group.

Compounds of the formula (and pharmaceutically acceptable derivatives thereof):

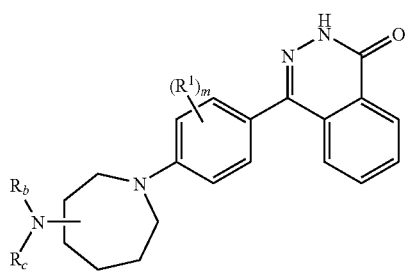

wherein m, $R^1$, $R_b$ and $R_c$ are as defined in classes and subclasses herein. In certain embodiments, $R_b$ and $R_c$ are independently hydrogen or lower alkyl. In certain embodiments, $R_b$ and $R_c$ are independently a hydrophilic group. In certain embodiments, $R_b$ and $R_c$ are independently an optionally substituted cyclic or acyclic $C_{6-12}$alkyl, $C_{6-12}$alkenyl, or $C_{6-12}$alkynyl group. In certain embodiments, $R_b$ and $R_c$ are independently an optionally substituted -(alkyl)aryl group.

Compounds of the formula (and pharmaceutically acceptable derivatives thereof):

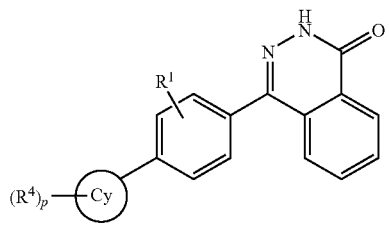

wherein Cy, p, $R^1$ and $R^4$ are as defined in classes and subclasses herein. In certain embodiments, p is 1-4 and each occurrence of $R^4$ is independently hydrogen or lower alkyl. In certain embodiments, at least one occurrence of $R^4$ is a hydrophilic group.

Compounds of the formula (and pharmaceutically acceptable derivatives thereof):

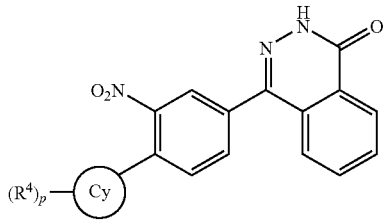

wherein Cy, p and $R^4$ are as defined in classes and subclasses herein. In certain embodiments, p is 1-4 and each occurrence of $R^4$ is independently hydrogen or lower alkyl. In certain embodiments, at least one occurrence of $R^4$ is a hydrophilic group.

Compounds of the formula (and pharmaceutically acceptable derivatives thereof):

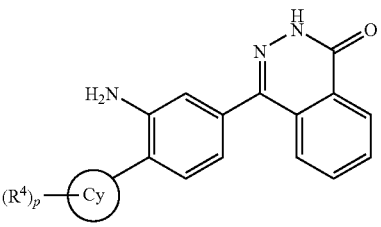

wherein Cy, p and $R^4$ are as defined in classes and subclasses herein. In certain embodiments, p is 1-4 and each occurrence of $R^4$ is independently hydrogen or lower alkyl. In certain embodiments, at least one occurrence of $R^4$ is a hydrophilic group.

Compounds of the formula (and pharmaceutically acceptable derivatives thereof):

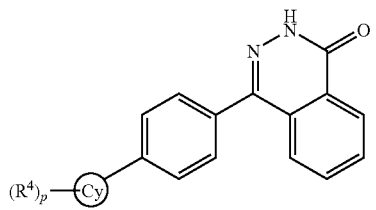

wherein Cy, p and $R^4$ are as defined in classes and subclasses herein. In certain embodiments, p is 1-4 and each occurrence of $R^4$ is independently hydrogen or lower alkyl. In certain embodiments, at least one occurrence of $R^4$ is a hydrophilic group.

Compounds of the formula (and pharmaceutically acceptable derivatives thereof):

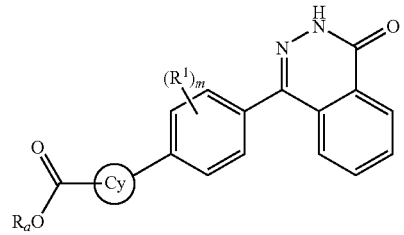

wherein Cy, m, $R^1$ and $R_a$ are as defined in classes and subclasses herein. In certain embodiments, $R_a$ is hydrogen. In certain embodiments, $R_a$ is lower alkyl.

Compounds of the formula (and pharmaceutically acceptable derivatives thereof):

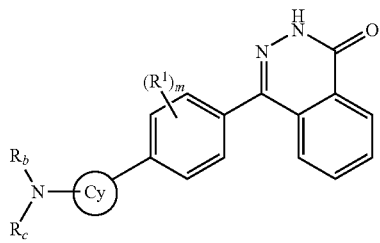

wherein Cy, m, $R^1$, $R_b$ and $R_c$ are as defined in classes and subclasses herein. In certain embodiments, $R_b$ and $R_c$ are independently hydrogen or lower alkyl.

In certain embodiments, for compounds of the classes above, at least one occurrence of $R^4$ is a hydrophobic group. In certain embodiments, each occurrence of $R^4$ is independently a hydrophobic group. In certain embodiments, the hydrophobic group is an aliphatic group. In certain embodiments, the hydrophobic group is an unsubstituted aliphatic group. In certain embodiments, the hydrophobic group is a cyclic or acyclic $C_{6-12}$alkyl, $C_{6-12}$alkenyl, or $C_{6-12}$alkynyl group. In certain embodiments, the hydrophobic group is an unsubstituted cyclic or acyclic $C_{6-12}$alkyl, $C_{6-12}$alkenyl, or $C_{6-12}$alkynyl group. In certain embodiments, the hydrophobic group is a -(alkyl)aryl group. In certain embodiments, the hydrophobic group is an unsubstituted -(alkyl)aryl group.

In certain embodiments, for compounds of the classes above, m is 0-2. In certain embodiments, m is 0. In certain embodiments, m is 1.

In certain embodiments, for compounds of the classes above, p is 0-2. In certain embodiments, p is 0. In certain embodiments, p is 1.

Non-limiting examples of compounds of the invention in Formula (VIII) include:

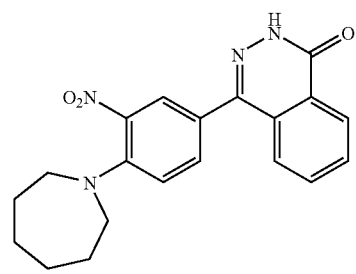

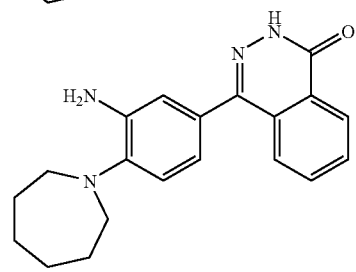

-continued

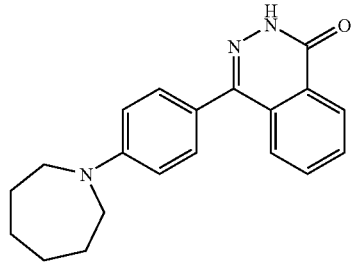

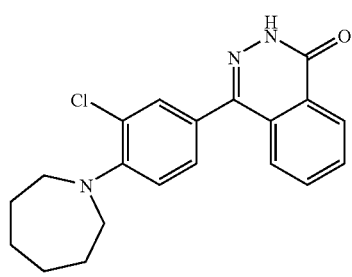

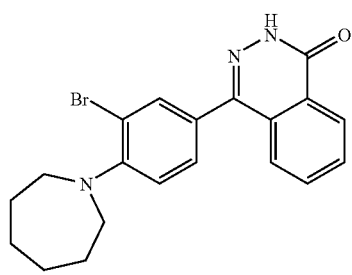

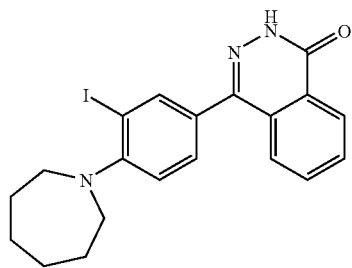

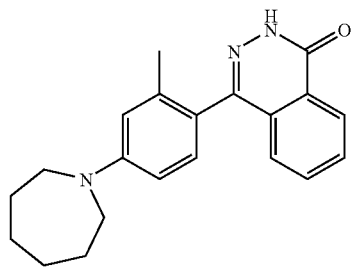

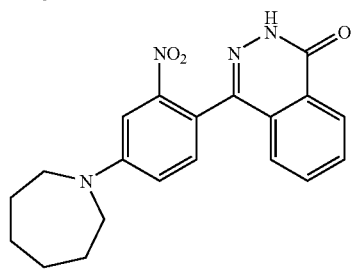

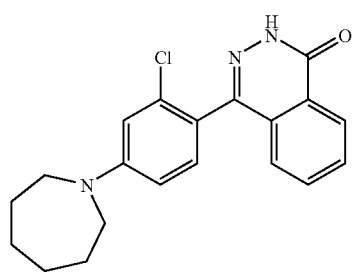
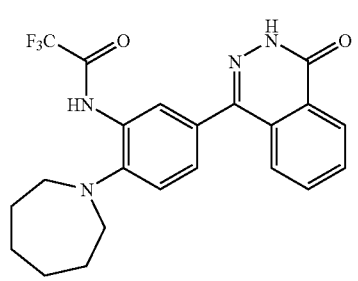
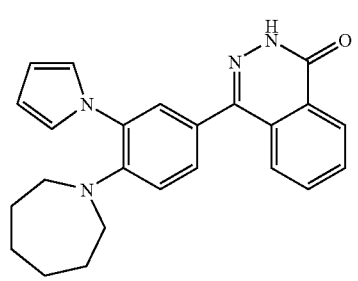
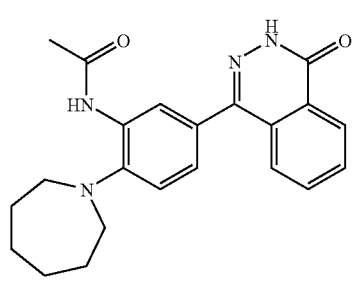
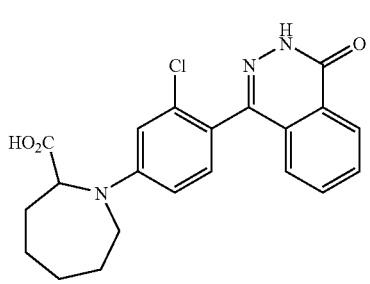
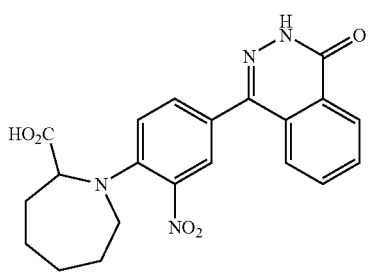
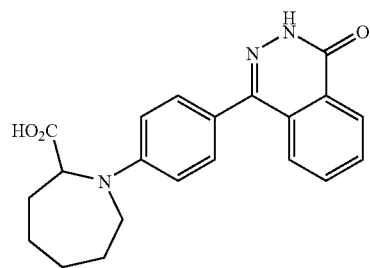
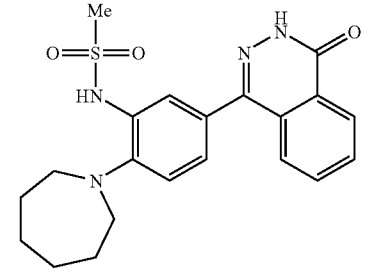
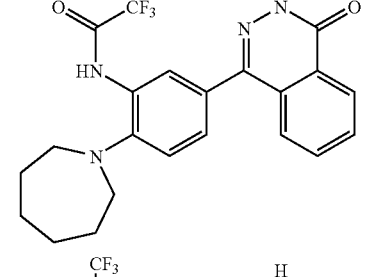
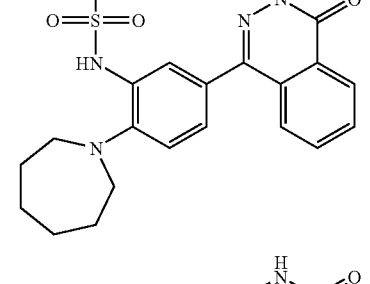
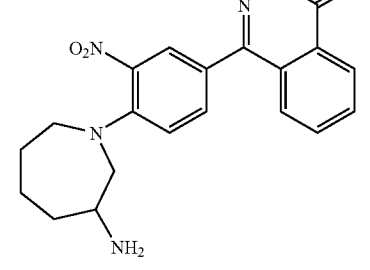
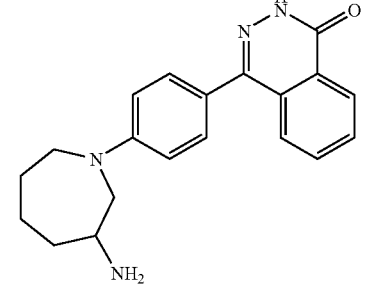

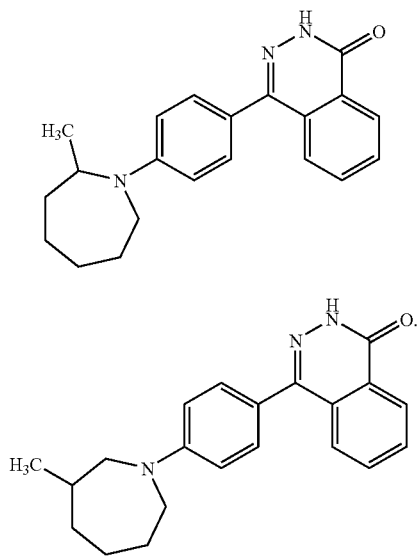
Examples of compounds of Formula (XI) where $R^2$ and $R^3$ do not form a ring include:
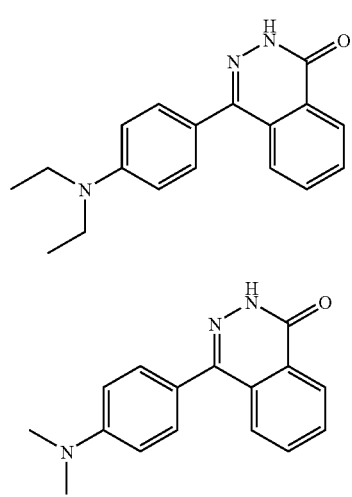
Non-limiting examples of compounds of Formula (XI) wherein the —$NR^2R^3$ moiety forms a ring, optionally further substituted, include the following compounds:
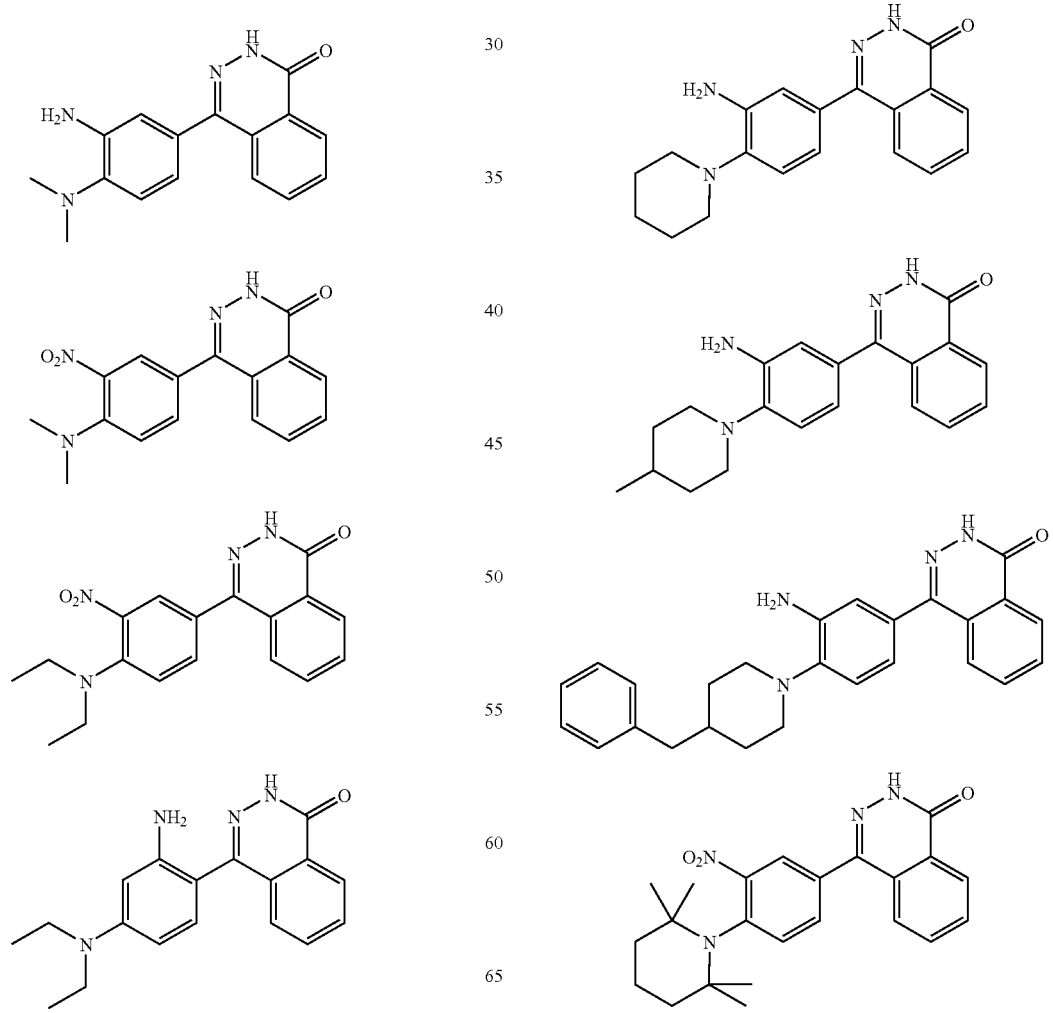

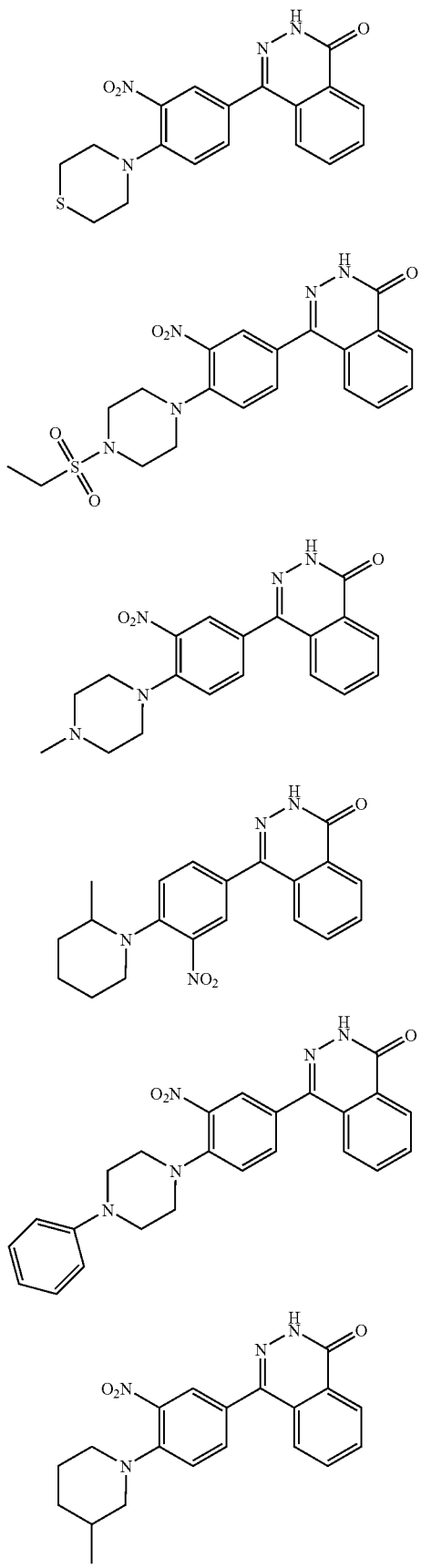
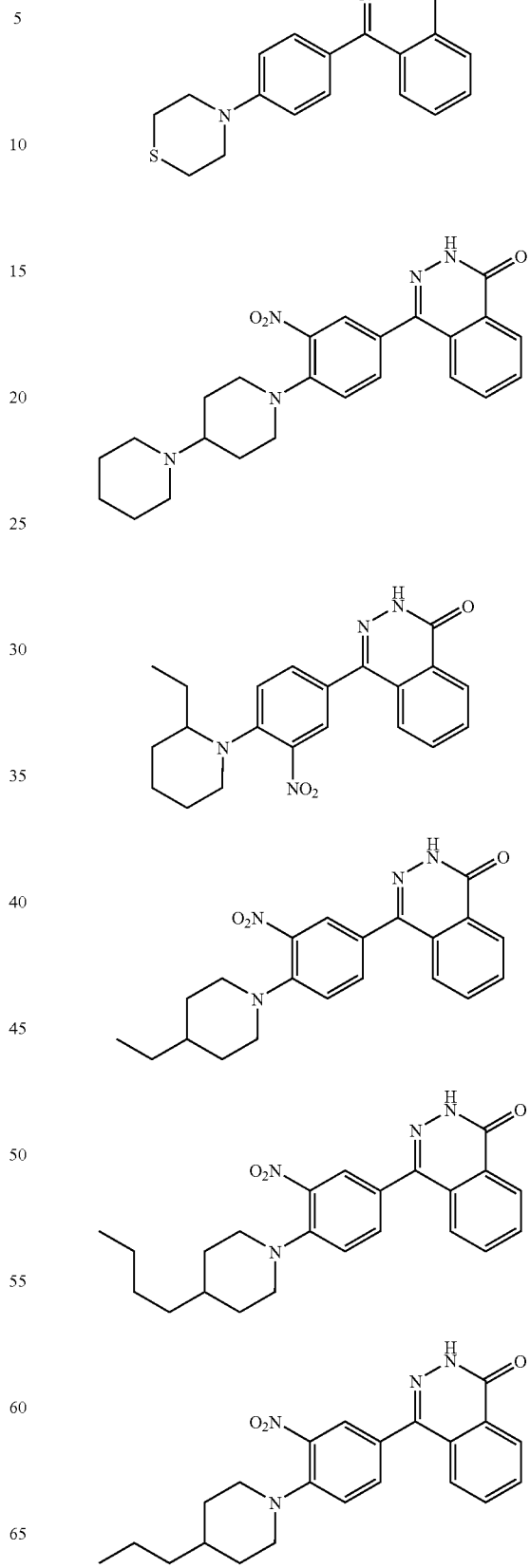

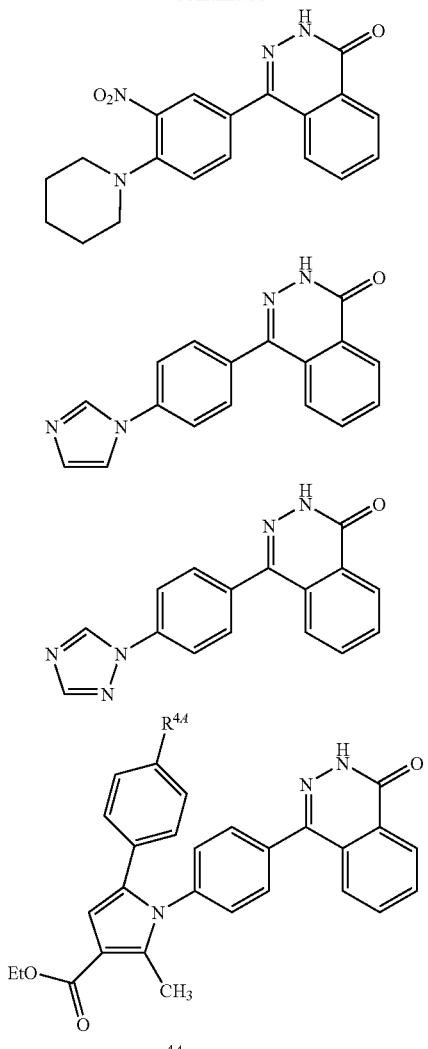

wherein R[44] is hydrogen, methyl, methoxy, chloro or —NO$_2$

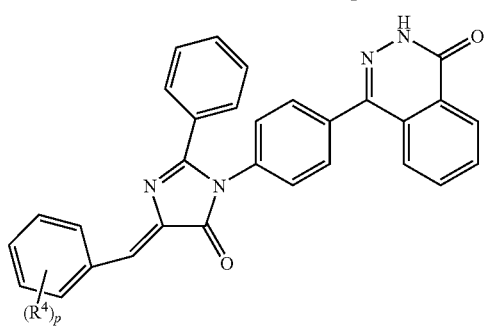

wherein p and R[4] are as defined in classes and subclasses herein.

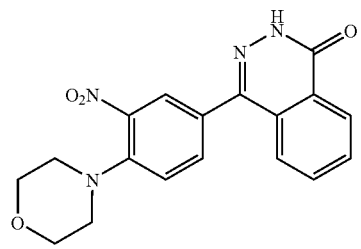

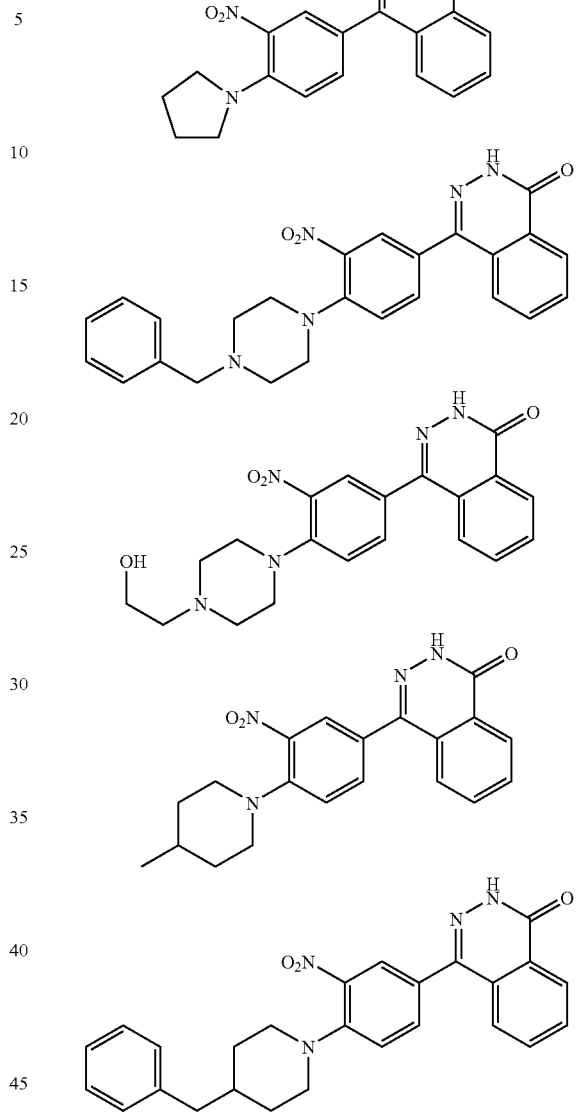

Some of the foregoing compounds can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds of the invention and one or more pharmaceutically acceptable excipients or additives.

Compounds of the invention for the uses described herein may be prepared by crystallization under different conditions and may exist as one or a combination of polymorphs of compound forming part of this invention. For example, different polymorphs may be identified and/or prepared using different solvents, or different mixtures of solvents for recrystallization; by performing crystallizations at different temperatures; or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other techniques. Thus, the present invention encompasses inventive compounds, their derivatives, their tautomeric forms, their stereoisomers, their polymorphs, their pharmaceutically acceptable salts their pharmaceutically acceptable solvates and pharmaceutically acceptable compositions containing them.

Compounds of this invention for the uses described include those specifically set forth above and described herein, and are illustrated in part by the various classes, subgenera and species disclosed elsewhere herein. Additionally, the present invention provides pharmaceutically acceptable derivatives of the inventive compounds, and methods of treating a subject using these compounds, pharmaceutical compositions thereof, or either of these in combination with one or more additional therapeutic agents. Certain compounds of the present invention are described in more detail below. For purposes of this invention, the chemical elements are identified in accordance with the Periodic Table of the Elements, CAS version, Handbook of Chemistry and Physics, 75$^{th}$ Ed., a inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups. It will be appreciated that the compounds, as described herein, may be substituted with any number of substituents or functional moieties.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a prodrug or other adduct or derivative of a compound of this invention which upon administration to a patient in need is capable of providing, directly or indirectly, a compound as otherwise described herein, or a metabolite or residue thereof.

Pharmaceutical Compositions

As discussed above this invention provides uses of compounds described herein that have biological properties useful for the treatment of chronic obstructive pulmonary diseases.

Accordingly, in another aspect of the present invention, pharmaceutical compositions for the uses described herein are provided, which comprise any one or more of the compounds described herein (or a prodrug, pharmaceutically acceptable salt or other pharmaceutically acceptable derivative thereof), and optionally comprise a pharmaceutically acceptable carrier. In certain embodiments, these compositions optionally further comprise one or more additional therapeutic agents. Alternatively, a compound of this invention may be administered to a patient in need thereof in combination with the administration of one or more other therapeutic agents. For example, additional therapeutic agents for conjoint administration or inclusion in a pharmaceutical composition with a compound of this invention may be an approved agent to treat the same or related indication, or it may be any one of a number of agents undergoing approval in the Food and Drug Administration that ultimately obtain approval for the treatment of any disorder related to HGF/SF activity. It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a pro-drug or other adduct or derivative of a compound of this invention which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in *J. Pharmaceutical Sciences*, 66: 1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hernisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters that hydrolyze in vivo and include those that break down readily in the human body to leave the parent compound or a salt thereof Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood, or N-demethylation of a compound of the invention where $R^1$ is methyl. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference. By way of example, N-methylated pro-drugs of the 3(5)-monosubstituted pyrazoles of the invention are embraced herein.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen free water; isotonic saline; Ringer's solution; ethyl alcohol, and phosphate buffer solutions; as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut (peanut), corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly (orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The present invention encompasses pharmaceutically acceptable topical formulations of inventive compounds. The term "pharmaceutically acceptable topical formulation", as used herein, means any formulation which is pharmaceutically acceptable for intradermal administration of a compound of the invention by application of the formulation to the epidermis. In certain embodiments of the invention, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, Remington's Pharmaceutical Sciences, 16th Edition, 1980 and 17th Edition, 1985, both published by Mack Publishing Company, Easton, Pa., the disclosures of which are incorporated herein by reference in their entireties. In certain other embodiments, the topical formulations of the invention may comprise excipients. Any pharmaceutically acceptable excipient known in the art may be used to prepare the inventive pharmaceutically acceptable topical formulations. Examples of excipients that can be included in the topical formulations of the invention include, but are not limited to, preservatives, antioxidants, moisturizers, emollients, buffering agents, solubilizing agents, other penetration agents, skin protectants, surfactants, and propellants, and/or additional therapeutic agents used in combination to the inventive compound. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerine, sorbitol, polyethylene glycols, urea, and propylene glycol. Suitable buffering agents for use with the invention include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the invention include, but are not limited to, vitamin E oil, allatoin, dimethicone, glycerin, petrolatum, and zinc oxide.

In certain embodiments, the pharmaceutically acceptable topical formulations of the invention comprise at least a compound of the invention and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term " penetration enhancing agent " means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, Percutaneous Penetration Enhancers, Maibach H. I. and Smith H. E. (eds.), CRC Press, Inc., Boca Raton, Fla. (1995), which surveys the use and testing of various skin penetration enhancers, and Buyuktimkin et al., Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, Ill. (1997). In certain exemplary embodiments, penetration agents for use with the invention include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate) and N-methyl pyrrolidone.

In certain embodiments, the compositions may be in the form of ointments, pastes, creams, lotions, gels, powders, solutions, sprays, inhalants or patches. In certain exemplary embodiments, formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, for example, polyoxy-40-stearate. In certain embodiments, the active component is admixed under sterile conditions with a pharmaceutically acceptable carrier and any needed preservatives or buffers as may be required. Ophthalmic formulation, eardrops, and eye drops are also contemplated as being within the scope of this invention. Formulations for intraocular administration are also included. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anti-inflammatory agent), or they may achieve different effects (e.g., control of any adverse effects). In non-limiting examples, one or more compounds of the invention may be formulated with at least one cytokine, growth factor or other biological, such as an interferon, e.g., alpha interferon, or with at least another small molecule compound. Non-limiting examples of pharmaceutical agents that may be combined therapeutically with compounds of the invention include: antivirals and antifibrotics such as interferon alpha, combination of interferon alpha and ribavirin, Lamivudine, Adefovir dipivoxil and interferon gamma; anticoagulants such as heparin and warfarin; antiplatelets e.g., aspirin, ticlopidine and clopidogrel; other growth factors involved in regeneration, e.g., VEGF and FGF and mimetics of these growth factors; antiapoptotic agents; and motility and morphogenic agents.

Research Uses, Clinical Uses, Pharmaceutical Uses and Methods of Treatment

In certain embodiments, the method involves the administration of a therapeutically effective amount of the compound or a pharmaceutically acceptable derivative thereof to a subject (including, but not limited to a human or animal) in need of it. Subjects for which the benefits of the compounds of the invention are intended for administration include, in addition to humans, livestock, domesticated, zoo and companion animals.

As discussed above this invention provides novel compounds that have biological properties useful for modulating, and preferably mimicking or agonizing, HGF/SF activity. It will be appreciated that the compounds and compositions, according to the method of the present invention, may be administered using any amount and any route of administration effective for the treatment of fibrotic connective tissue diseases. Thus, the expression "effective amount" as used herein, refers to a sufficient amount of agent to modulate HGF/SF activity (e.g., mimic HGF/SF activity), and to exhibit a therapeutic effect. The exact amount required will vary from subject to subject, depending on the species, age, and general condition of the subject, the severity of the infection, the particular therapeutic agent, its mode and/or route of administration, and the like. The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, subcutaneously, intradermally, intra-ocularly, topically (as by powders, ointments, or drops), buccally, as an oral or nasal spray, or the like, depending on the severity of the disease or disorder being treated. In certain embodiments of the invention, the compound or pharmaceutical composition of the invention is administered by a route and a dose and frequency of dosing to provide therapeutic levels to achieve the benefits described herein. Preferably routes of administration other than parenteral to address the lung diseases described herein include inhalation, such as by use of aerosols or fine powders, and other intra-pulmonary routes and methods. In certain embodiments, the small molecule compounds of the invention may be administered at dosage levels of about 0.001 mg/kg to about 50 mg/kg, preferably from about 0.1 mg/kg to about 10 mg/kg for parenteral administration, or preferably from about 1 mg/kg to about 50 mg/kg, more preferably from about 10 mg/kg to about 50 mg/kg for oral administration, of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject. In certain embodiments, compounds are administered orally or parenterally.

Moreover, pharmaceutical compositions comprising one or more compounds of the invention may also contain other compounds or agents for which co-administration with the compound(s) of the invention is therapeutically advantageous. As many pharmaceutical agents are used in the treatment of the diseases and disorders for which the compounds of the invention are also beneficial, any may be formulated together for administration. Synergistic formulations are also embraced herein, where the combination of at least one compound of the invention and at least one other compounds act more beneficially than when each is given alone.

Treatment Kit

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

Equivalents

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

Exemplification

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

General Description of Synthetic Methods:

The practitioner has a well-established literature of small molecule chemistry to draw upon, in combination with the information contained herein, for guidance on synthetic strategies, protecting groups, and other materials and methods useful for the synthesis of the compounds of this invention. Reference is made to the above citations for the preparation of the compounds and their pharmaceutical compositions, such as WO2004/058721, WO02/002593, U.S. Pat. No. 6,589,997, U.S. patent application Ser. No. 11/238,285, and PCT/US2005/034669 (WO2006/036981).

Example 1

Activity of Compounds in Scleroderma Models: Methods

Bleomycin model. In a pilot study, bleomycin (Sigma) was dissolved in phosphate buffered saline (PBS) at a concentration of 1 mg/ml and 100 µl injected subcutaneously into the shaved backs of C57BL/6 mice with a 27 gauge needle daily for four weeks. In one study, vehicle (n=10) or test compound (n=10) (2 mg/kg, i.p) treatment was administered simultaneously with bleomycin infusion (co-treatment) for four weeks. Phosphate-buffered saline (PBS) was given instead of bleomycin in a placebo group (n=10). At the end of each dosing period, the mice were euthanized by $CO_2$ inhalation on the day following final treatment.

In another study designed as an intervention mode, after a delay of three weeks following the start of daily bleomycin administration, test compound or vehicle were administered daily for three weeks.

TSK1/+ model. The tight skin (TSK) mouse from Jackson Laboratories was used. Female TSK1/+ animals at six weeks of age were injected daily, i.p., vehicle (n=5) or test compound (n=5) for 12 days.

In all studies, the treated sites of truncal skin tissue samples were harvested for histological and fibrotic analyses. Dermal thickening, and histological evaluation (Trichrome staining and H&E staining) performed as described below.

Histological Examination. The dorsal skin tissue of mice will be removed on the day following the final test compound or vehicle injection. Skin samples (4 $cm^2$) were removed from the dorsal side immediately below the neck in a manner that minimized stress. Dorsal tissue was separated into several portions/sections. Samples were fixed for 16 h in buffered saline containing formalin, cut into 2-3-mm-wide longitudinal strips, dehydrated, embedded in paraffin, were stained with hematoxylin/eosin and Trichrome staining according to routine histological methods for collagen estimation and fibrotic score evaluation. Photographs were taken from a microscope that is connected to a computerized digital camera. The Bioquant image analysis computer program was used to quantify the degree of fibrosis. The image analysis program quantitates stained vs. non-stained regions within each field.

Skin thickness measurements. Skin was removed from the interscapular region of the back, was fixed and embedded in paraffin, sectioned (4-µm thick), and stained with hematoxylin/eosin stain. The stained cross-sections of skin were viewed under the microscope, photographed. The thickness of the skin was determined by measuring the distance from the epidermis to the layer to the junction between the dermis and subcutaneous fat on hematoxylin/eosin stained sections from the photograph with a millimeter ruler and divided by the magnification to obtain the actual skin thickness.

Quantitative Histological Evaluation of Fibrotic Score. Histological analysis of mouse fibrotic changes following treatment were determined using a numerical fibrotic scale (Ashcroft scale). The severity of the fibrotic changes in each skin section were assessed as a mean score of severity from observed microscopic fields. More than 10 fields within each skin sections was observed at a magnification of 20× in each successive field, and each field will be assessed individually for the severity of fibrotic changes and will be allotted a score from 0 (normal) to 8 (total fibrosis) using a predetermined scale of severity. After examining the entire section, the mean scores from all fields were taken as the fibrotic score. Each specimen was scored blindly by three observers, including a histopathologist. The mean of their individual scores were considered as the fibrotic score.

Biochemical Analyses for collagen content: Hydroxyproline analyses were performed on duplicate punches from each mouse by standard procedures presently in use in Christner's laboratory. Collagen content is directly proportional to hydroxyproline content. Briefly, full-thickness punch-biopsied specimens of 6 mm diameter were obtained from the shaved dorsal skin of each mice and stored at −80° C. The stored skin pieces were hydrolyzed with 6 N HCl under 110° C. for 18 h according to the method as described by Woesner et al. The pH of the samples was adjusted to between 6 and 7. An aliquot from the sample will be added to 1.4% chloramine and incubate at room temperature. After 20 min, 3.15 M perchloric acid, followed by Erlich's solution 5 min later. The efficiency of the hydrolysis will be verified with rat tail collagen by comparison to standard hydroxyproline (Sigma). After incubation at 65° C. for 20 min, absorbance was measured at 562 nm with a Molecular Devices UV MAX plate reader. Results were expressed as micrograms of hydroxyproline per gram tissue or ug/lung.

Immunohistochemistry for total c-met, Phospho met. Cryostat sections (4 μm) prepared from vehicle and test compound treated rat skin tissues, air-dried, fixed in 10% buffered formalin for 5 minutes, and washed in PBS for 10 minutes. Endogenous peroxidase were blocked with 3% hydrogen peroxide in PBS and then sections were incubated with primary anti-c-met and phosphor c-met, (Cell Signaling) antibodies with dilution of 1:500 in PBS containing 1% bovine serum albumin for one hour and washed in PBS for 10 minutes. Sections were incubated with immunoglobulin G-peroxidase-conjugated secondary antibodies (Sigma) at a dilution of 1:150, washed in PBS for 10 minutes, incubated with 0.5 mg/mL diaminobenzidine tetrahydrochloride 2-hydrate plus 0.05% H2O2 for 10 minutes, and again washed in PBS. Negative control sections were incubated with secondary antibody alone, stained with hematoxylin, dehydrated, mounted, and viewed by light microscopy. Immunohistochemical staining for total c-met and phosphor c-Met were quantitated (n=4 per group) using computerized image analysis. 5 fields from each section and each group will be averaged. The detection level threshold for positively stained areas (brown for DAB staining) was set up so that the processed image accurately reflects the positively stained areas as visualized by light microscopy and on the unprocessed digital image.

Protein expression. Expression of alpha-smooth muscle actin (SMA), transforming growth factor (TGF)-beta and connective tissue growth factor (CTGF) were quantitated using immunohistochemical methods.

Statistical Analysis. All values were calculated as mean±SD of mouse skin tissue sections analysis for each group. Statistical analysis of the results were performed with ANOVA and p values lower than 0.05 will be considered significant.

Example 2

Bleomycin Model

As shown in FIG. 1A-D, by histological evaluation, the compound of the invention decreases dermal thickness (H&E stain; FIG. 1A) and fibrotic score (Trichrome staining; FIG. 1B). Using immuno-histochemical staining of total c-Met and phospho-c-Met, total c-met upregulation occurred with bleomycin (FIG. 1C) and the compound increased phosphorylation of c-met but not in the vehicle group (FIG. 1D).

In another co-treatment study using the bleomycin model and two compounds of the invention, quantitation of the histological evaluation using H&E staining (FIG. 2A, top row) and Trichrome (bottom row) is shown for normal (left panels), vehicle (center left panels), and two compounds (right ceter and far right paels). Fibrotic score (FIG. 2B) and dermal thickness (FIG. 2C) are quantitated. In both measurements, the compounds were effective at lowering the score and thickness.

In the intervention study using bleomycin, folded skin dermal thickness, dermal thickness, CTGF expression, TGF-beta and alpha-SMA expression (FIGS. 3A-E, respectively) showed reductions by two compounds of the invention administered after three weeks of established pathology caused by bleomycin.

Example 3

TSK Model

In the TSK model, reduction in folded skin dermal thickness, dermal alpha-SMA, dermal TGF-beta expression and lung hydroxyproline were found to have occurred as a result of administration of a compound of the invention (FIG. 4A-D, respectively).

In another experiment using TSK1/+ mice, five-week old TSK-1/+ mice were injected (i.p.) once daily with vehicle (n=10) or compound of the invention (2 mg/kg, n=10) for 10 days. At the end of the treatment period, truncal skin was harvested for histological and fibrotic analyses. As seen in FIG. 5, treatment with compound attenuates fibrotic progression in skin (Trichrome staining).

Example 4

Anti-Fibrotic Effects on Fibroblasts Isolated from Scleroderma Patients

Dermal fibroblasts (passage 4) from early diagnosed rapidly progressing diffuse SSc patients were grown to confluence in 10% FBS DMEM. A compound of the invention was used at a 2 uM concentration for 48 hours. The results as shown in FIG. 6A-B, demonstrate that a compound of the invention inhibited TGF-beta1 mRNA levels (A) and collagen 1 (B) in the SSc line (p<0.05) compared to vehicle treatment.

What is claimed is:

1. A method for treating a fibrotic connective tissue disease or disorder comprising administering to a subject in need thereof an effective amount of a pharmaceutical composition comprising a carrier and a compound of formula (I):

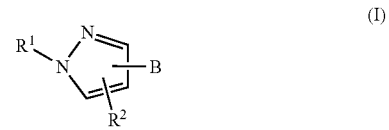

and tautomers thereof;

wherein B is a C(3)- or C(5)-substituent selected from the group consisting of -AL$^1$-A, phenoxyphenyl, aryl, heteroaryl, aryl substituted heteroaryl, and heterocyclic; wherein AL$^1$ is an optionally substituted C$_{2-6}$alkenylidene moiety, and A is an optionally substituted alicyclic, heteroalicyclic, aromatic or heteroaromatic moiety;

R$^1$ is hydrogen, methyl, —C(=O)(CH$_2$)$_m$R$^{14}$, —C(=O)OR$^{14}$, —C(=O)N(R$^{14}$)$_2$ or —SO$_2$R$^{14}$; wherein m is an integer from 0-3; each occurrence of R$^{14}$ is independently hydrogen or an optionally substituted aliphatic, alicyclic, heteroaliphatic, heteroalicyclic, aromatic or heteroaromatic moiety; and R² is one or more substituents selected from the group consisting of hydrogen, halogen, hydroxyl, —NO₂, —CN, arylcarbonylvinyl, S-heteroaryl, an optionally substituted aliphatic, heteroaliphatic, aromatic, heteroaromatic moiety; —CH₂Rᵃ, —ORᴿ, —S(=O)ₙRᵈ, —NRᵇRᶜ, and —C(=O)Rᵃ; wherein n is 0-2, Rᴿ is an optionally substituted aliphatic, heteroaliphatic, aromatic or heteroaromatic moiety;

Rᵃ, for each occurrence, is independently selected from the group consisting of hydrogen, hydroxy, aliphatic, heteroaliphatic, aryl and heteroaryl;

Rᵇ and Rᶜ, for each occurrence, are independently selected from the group consisting of hydrogen; hydroxy; SO₂Rᵈ; aliphatic, heteroaliphatic, aryl and heteroaryl;

Rᵈ, for each occurrence, is independently selected from the group consisting of hydrogen; —N(Rᵉ)₂; aliphatic, aryl and heteroaryl; and Rᵉ, for each occurrence, is independently hydrogen or aliphatic.

2. The method of claim 1 wherein the compound of formula (I) has the structure (II):

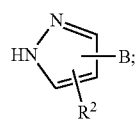

(II)

and tautomers thereof.

3. The method of claim 2 wherein the compound of formula (II) has the structure (IIᴬ):

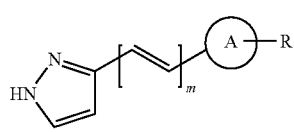

(IIᴬ)

and tautomers thereof;
wherein m is an integer from 0-3;
R is one or more substituents selected from the group consisting of hydrogen, halogen, hydroxyl, —NO₂, —CN, an optionally substituted aliphatic, heteroaliphatic, aromatic, heteroaromatic moiety; —ORᴿ, —S(=O)ₙRᵈ, —NRᵇRᶜ, and —C(=O)Rᵃ; wherein n is 0-2, Rᴿ is an optionally substituted aliphatic, heteroaliphatic, aromatic or heteroaromatic moiety; and A is an optionally substituted aromatic or non-aromatic 5-6 membered monocyclic ring, optionally containing 1-4 heteroatoms selected from N, O or S; or an optionally substituted aromatic or non-aromatic 8-12 membered bicyclic ring, optionally containing 1-6 heteroatoms selected from N, O or S.

4. The method of claim 3 wherein the compound is

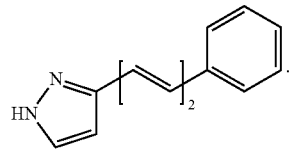

5. The method of claim 2 wherein the compound of formula (II) has the structure (IIᴮ):

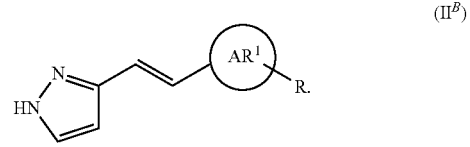

(IIᴮ)

and tautomers thereof;
wherein AR¹ is an optionally substituted aryl moiety; and
R is one or more substituents selected from the group consisting of hydrogen, halogen, hydroxyl, —NO₂, —CN, an optionally substituted aliphatic, heteroaliphatic, aromatic, heteroaromatic moiety; —ORᴿ, —S(=O)ₙRᵈ, —NRᵇRᶜ, and —C(=O)Rᵃ; wherein n is 0-2, Rᴿ is an optionally substituted aliphatic, heteroaliphatic, aromatic or heteroaromatic moiety.

6. The method of claim 5 wherein the compound is selected from among

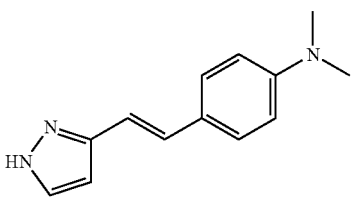

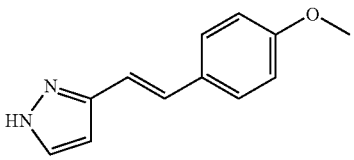

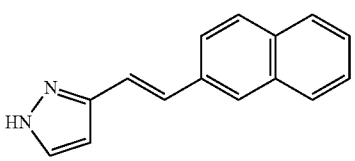

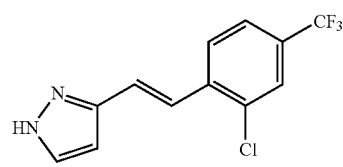

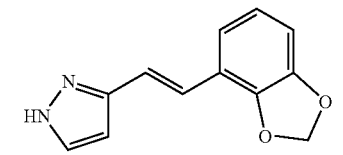

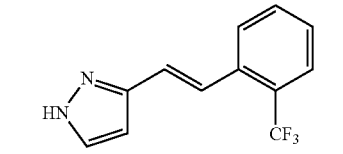

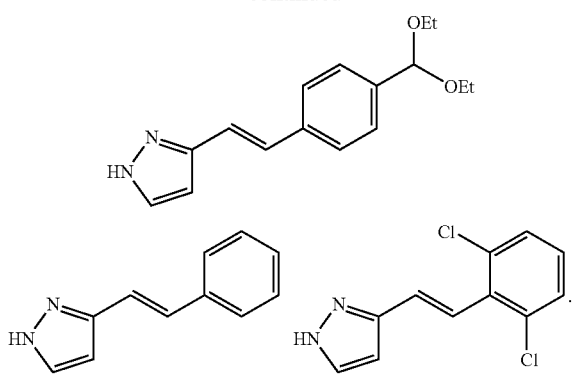

7. The method of claim 2 wherein the compound of formula (II) has the structure (II$^C$):

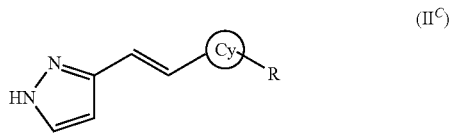

and tautomers thereof;

wherein Cy is an optionally substituted heterocyclic moiety; and

R is one or more substituents selected from the group consisting of hydrogen, halogen, hydroxyl, —NO$_2$, —CN, an optionally substituted aliphatic, heteroaliphatic, aromatic, heteroaromatic moiety; —OR$^R$, —S(=O)$_n$R$^d$, —NR$^b$R$^c$, and —C(=O)R$^a$; wherein n is 0-2, R$^R$ is an optionally substituted aliphatic, heteroaliphatic, aromatic or heteroaromatic moiety.

8. The method of claim 7 wherein the compound is selected from among

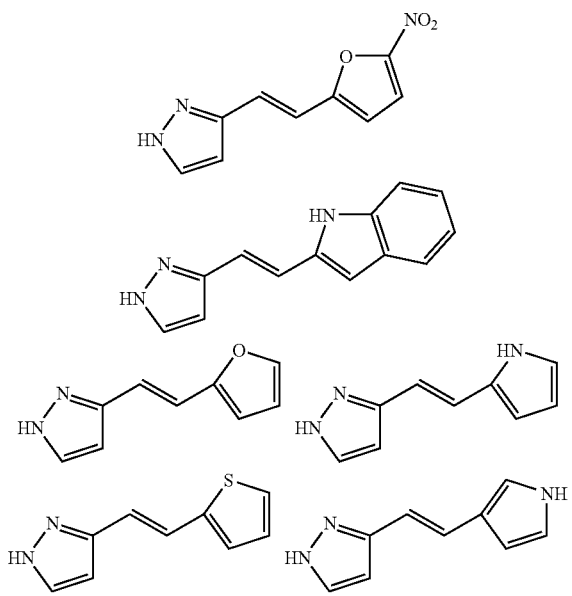

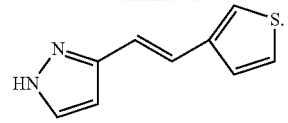

9. The method of claim 1 wherein the compound of formula (I) has the structure structure (III$^A$):

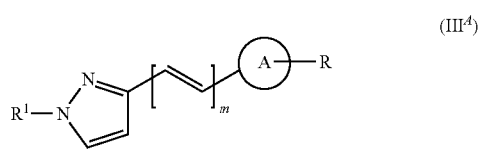

and C(5)-positional isomers thereof;

wherein m is an integer from 0-3;

R is one or more substituents selected from the group consisting of hydrogen, halogen, hydroxyl, —NO$_2$, —CN, an optionally substituted aliphatic, heteroaliphatic, aromatic, heteroaromatic moiety; —OR$^R$, —S(=O)$_n$R$^d$, —NR$^b$R$^c$, and —C(=O)R$^a$; wherein n is 0-2, R$^R$ is an optionally substituted aliphatic, heteroaliphatic, aromatic or heteroaromatic moiety; and A is an optionally substituted aromatic or non-aromatic 5-6 membered monocyclic ring, optionally containing 1-4 heteroatoms selected from N, O or S; or an optionally substituted aromatic or non-aromatic 8-12 membered bicyclic ring, optionally containing 1-6 heteroatoms selected from N, O or S.

10. The method of claim 9 wherein the compound of formula (III$^A$) has the structure (III$^B$):

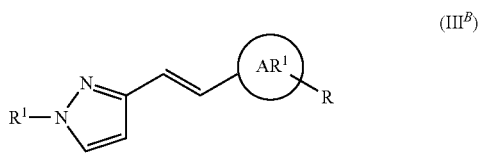

and C(5)-positional isomers thereof;

wherein AR$^1$ is an optionally substituted aryl moiety; and

R is one or more substituents selected from the group consisting of hydrogen, halogen, hydroxyl, —NO$_2$, —CN, an optionally substituted aliphatic, heteroaliphatic, aromatic, heteroaromatic moiety; —OR$^R$, —S(=O)$_n$R$^d$, —NR$^b$R$^c$, and —C(=O)R$^a$; wherein n is 0-2, R$^R$ is an optionally substituted aliphatic, heteroaliphatic, aromatic or heteroaromatic moiety.

11. The method of claim 10 wherein the compound is selected from among

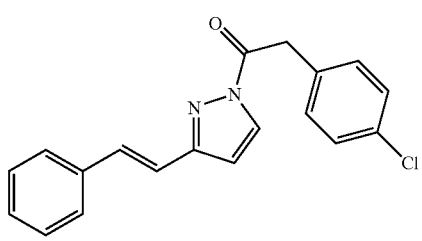

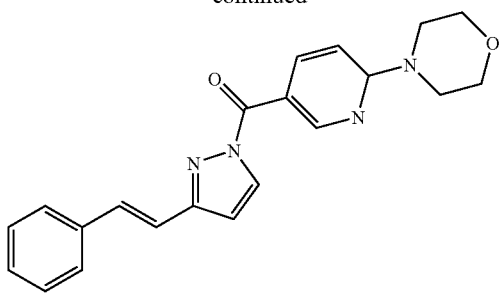
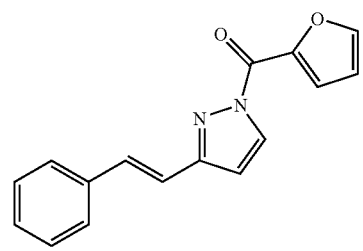
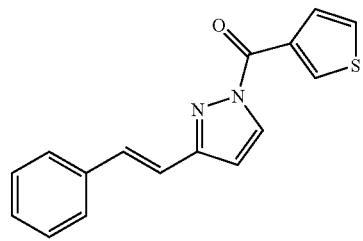
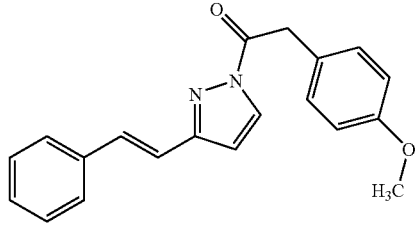
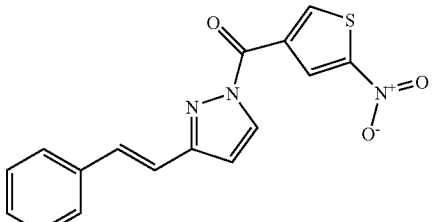
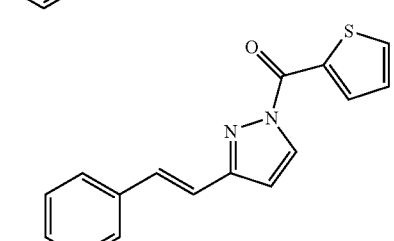
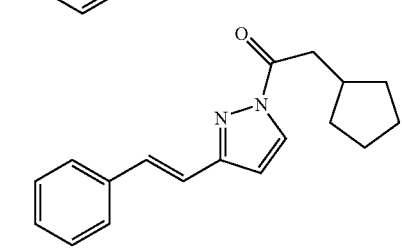
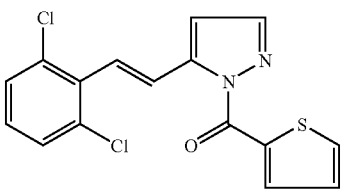
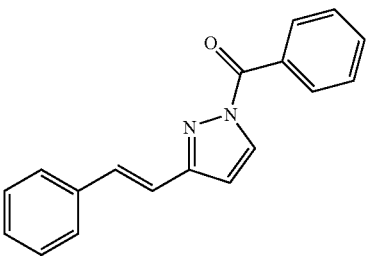
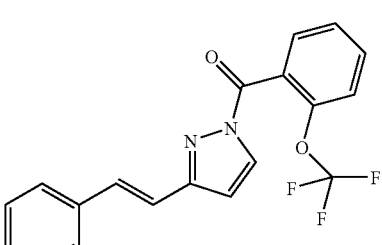
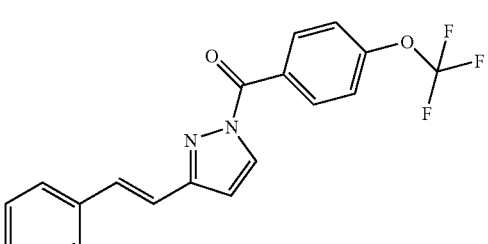
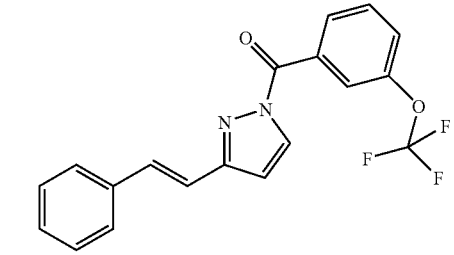
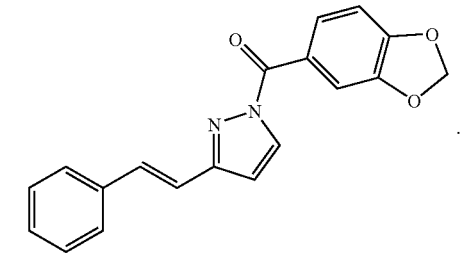

12. The method of claim 9 wherein the compound of formula (III$^A$) has the structure structure (III$^C$):
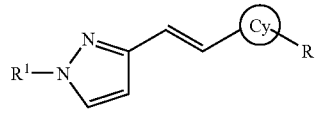
and C(5)-positional isomers thereof;
wherein Cy is an optionally substituted heterocyclic moiety.
13. The method of claim 12 wherein the compound is selected from among
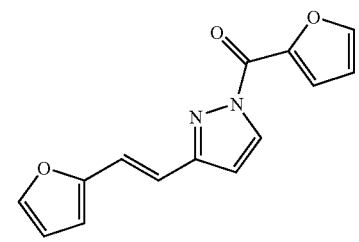
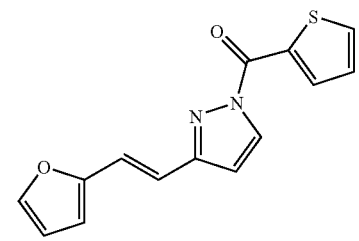
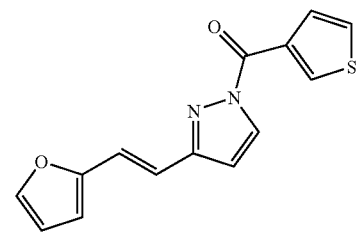
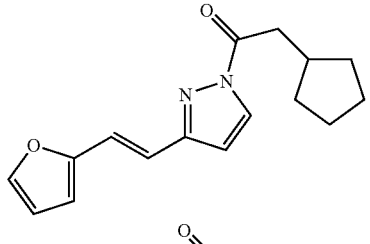
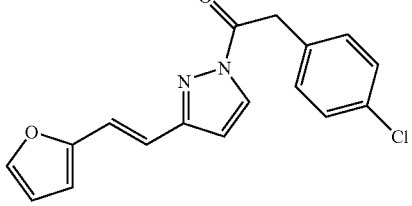
-continued
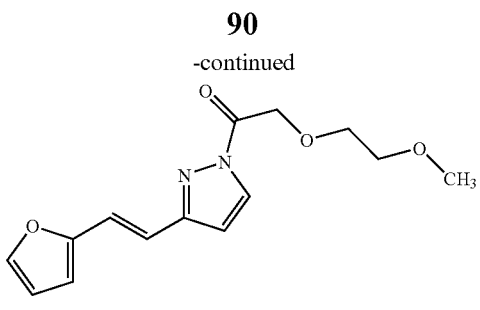
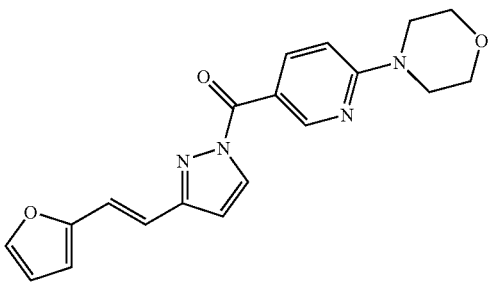
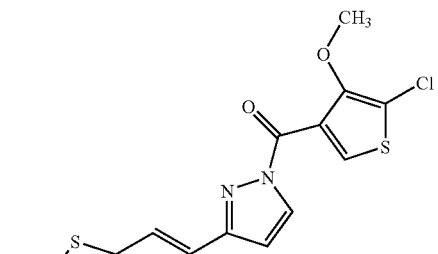
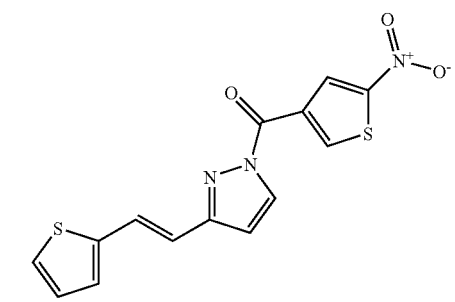
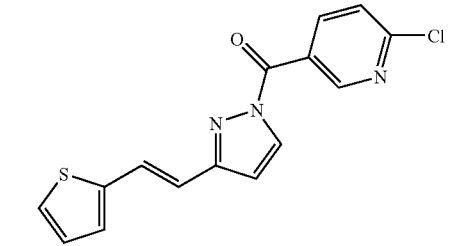
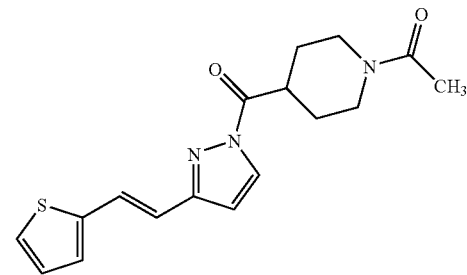

91
-continued
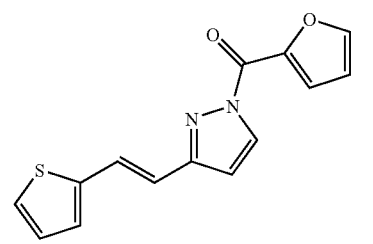
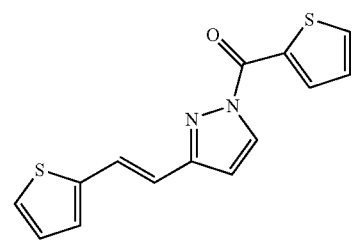
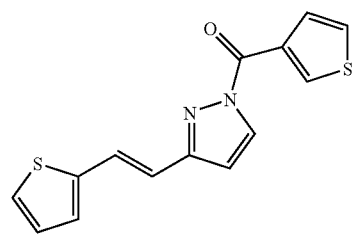
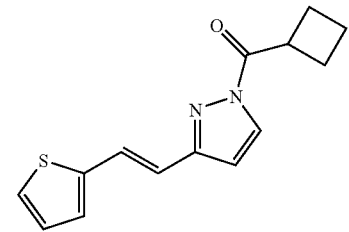
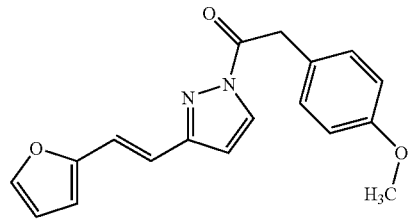
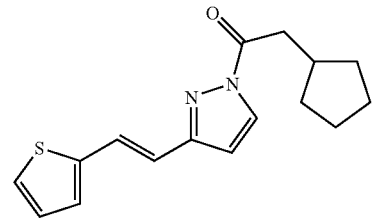
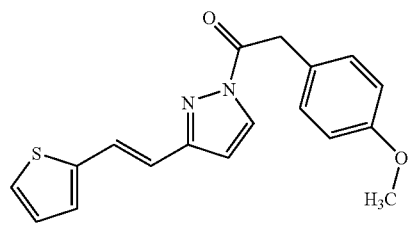
92
-continued
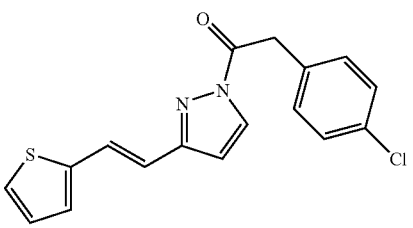
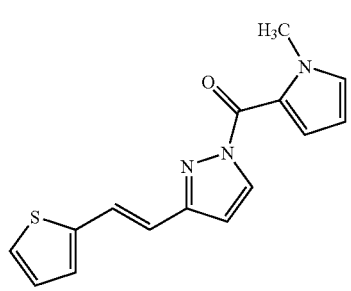
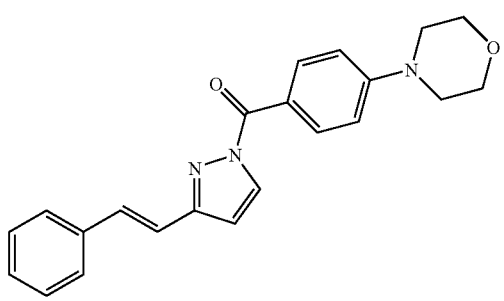
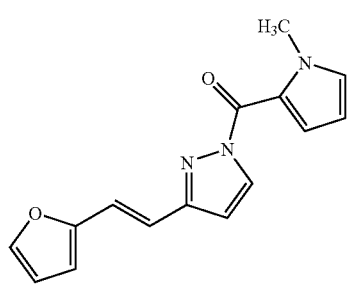
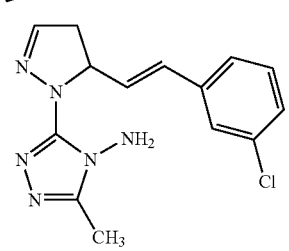
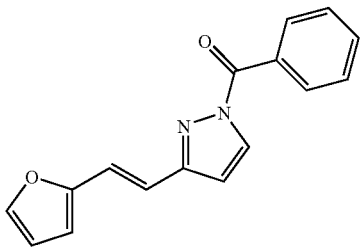

93
-continued
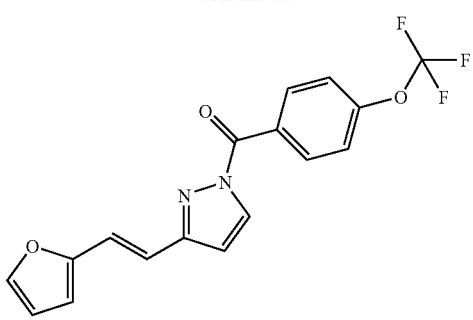
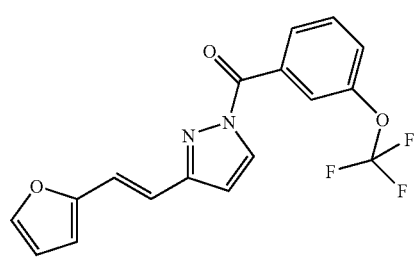
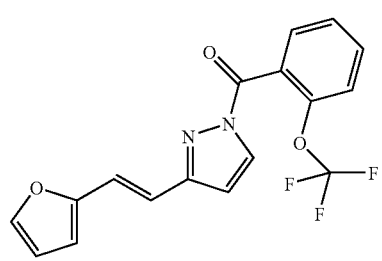
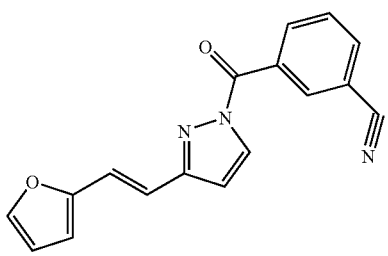
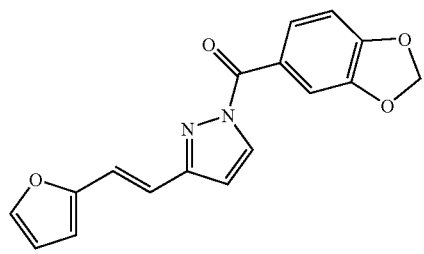
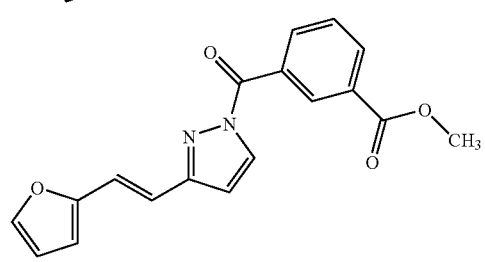
94
-continued
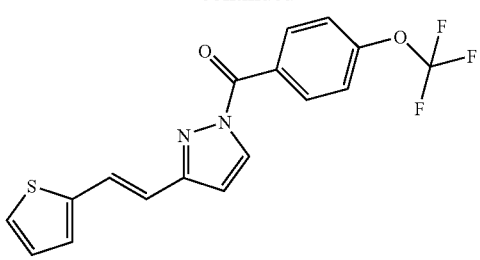
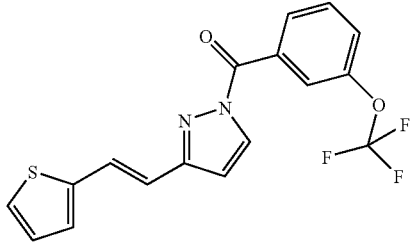
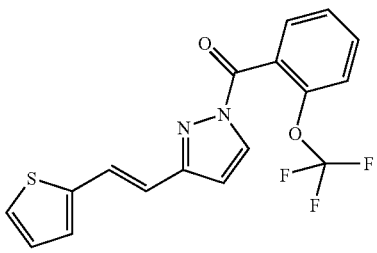
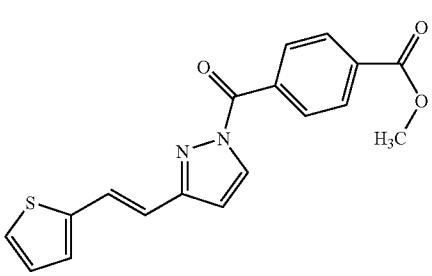
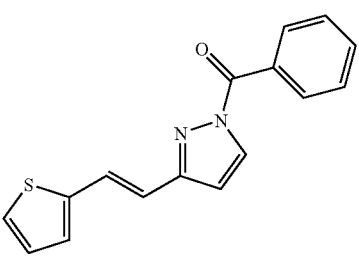
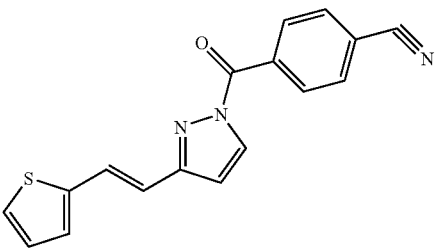

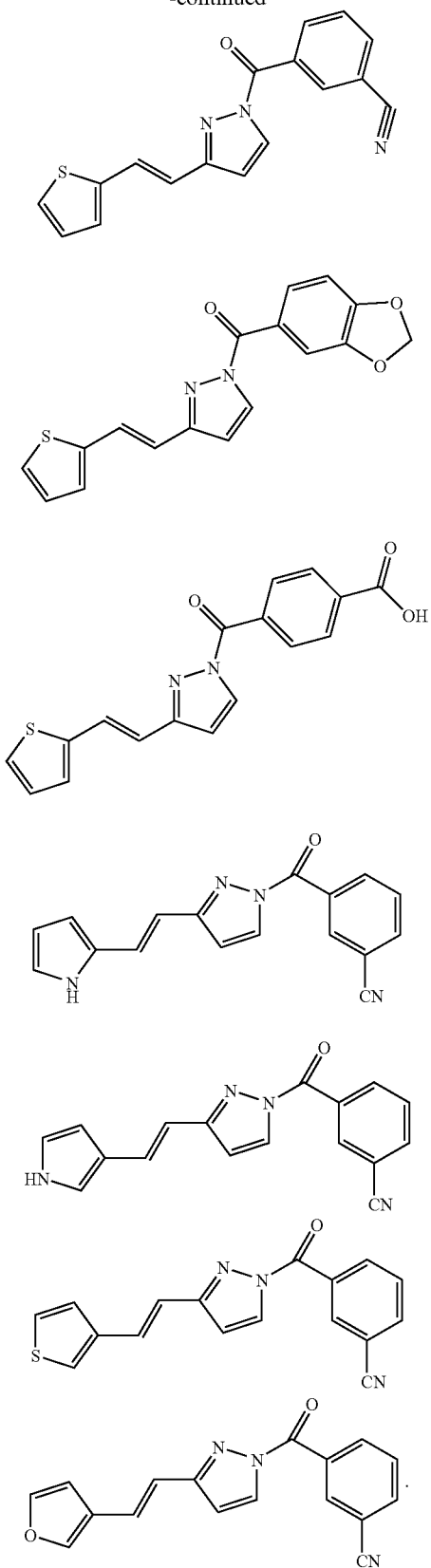

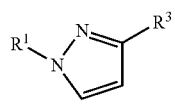

(III<sup>D</sup>)

and C(5)-positional isomers thereof;
wherein R¹ is —SO₂R¹⁴; —C(=O)(CH₂)ₘR¹⁴, —C(=O)OR¹⁴ or —C(=O)NHR¹⁴, wherein m is an integer from 0-3; and each occurrence of R¹⁴ is independently an optionally substituted aliphatic, alicyclic, heteroaliphatic, aryl or heterocyclic moiety; and R³ is a cis or trans —CH=CH-AR¹, —CH=CH-Cy, phenoxyphenyl, or a heterocyclic group; wherein AR¹ is an optionally substituted aryl moiety and Cy is an optionally substituted heterocyclic moiety.

15. The method of claim 14 wherein the compound is selected from among
(4-chlorophenyl)[3-(2-(2-thienyl)vinyl)-1H-pyrazol-1-yl]methanone;
1-(methylsulfonyl)-3-(2-(2-thienypvinyl)-1H-pyrazole
2,2-dimethyl-1-(3-(2-(2-thienyl)vinyl)-1H-pyrazole-1-yl)propan-1-one
N-methyl-3-(2-(2-thienyl)vinyl)-1H-pyrazole-1-carboxamide
(4-chlorophenyl)(3-(3-phenylisoxazol-5-yl)-1H-pyrazol-1-yl)methanone
(4-chlorophenyl)(3-(3-(4-chlorophenyl)-5-methylisoxazol-4-yl)-1H-pyrazol-1-yl)methanone
(4-chlorophenyl)(3-(5-(2-thienyl)-2-thienyl)-1H-pyrazol-1-yl)methanone
(2,4-dichlorophenyl)(3-(5-(2,4-difluorophenyl)-2-furyl)-1H-pyrazol-1-yl)methanone
N1-phenyl-3-(2-(2-thienyl)vinyl)-1H-pyrazole-1-carboxamide
(4-chlorophenyl)(3-(2-(5-(2-thienyl)-2-thienyl)-4-methyl-1,3-thiazol-5-yl)-1H-pyrazol-1-yl)methanone
(3-benzhydryl-1H-pyrazol-1-yl)(4-chlorophenyl)methanone
N1-(4-chlorophenyl)-3-(2-(2-thienyl)vinyl)-1H-pyrazole-1-carboxamide
(4-chlorophenyl)(3-(2-methylimidazo(1,2-a)pyridin-3-yl)-1H-pyrazol-1-yl)methanone
2-chloro-6-(4-(1-(4-chlorobenzyl)-1H-pyrazol-3-yl)phenoxy)benzonitrile; and
1-((4-chlorophenyl)sulfonyl)-3-(2-(2-thienyl)vinyl)-1H-pyrazole.

16. A method for treating a fibrotic connective tissue disease comprising administering to a subject in need thereof an effective amount of a pharmaceutical composition comprising a carrier and a compound of Formula (VIII) or (XI):

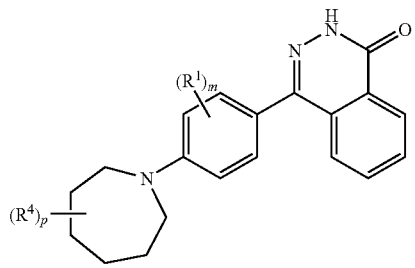

(VIII)

14. The method of claim 9 wherein the compound of formula (III⁴) has the structure structure (III<sup>D</sup>):

-continued

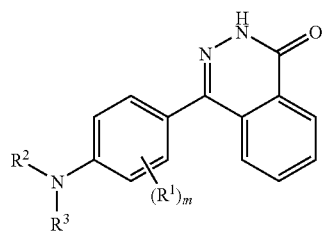

(XI)

or pharmaceutically acceptable derivatives thereof;
wherein m is an integer from 1 to 4;
p is an integer from 1 to 6;
each occurrence of $R^1$ and $R^4$ is independently hydrogen, halogen, hydroxyl, —$NO_2$, —$NH_2$, —CN, an optionally substituted aliphatic, alicyclic, heteroaliphatic, heterocyclic, aromatic or heteroaromatic moiety, —$OR^R$, —$S(=O)_nR^d$, —$NR^bR^c$, —$C(=O)R^a$, —$OPO_2OR^a$ or —$C(=O)OR^a$; wherein n is 0-2, $R^R$ is an optionally substituted aliphatic, alicyclic, heteroaliphatic, heterocyclic, aromatic, heteroaromatic or acyl moiety;
$R^2$ and $R^3$ are independently hydrogen, hydroxyl, —$NH_2$, an optionally substituted aliphatic, heteroaliphatic, alicyclic, heterocyclic, aromatic or heteroaromatic moiety, —$OR^R$, —$S(=O)_nR^d$, —$NR^bR^c$, —$C(=O)R^a$ or —$C(=O)OR^a$;
wherein n is 0-2, $R^R$ is an optionally substituted aliphatic, heteroaliphatic, alicyclic, heterocyclic, aromatic or heteroaromatic or acyl moiety; or $R^2$ and $R^3$ taken together with the nitrogen to which they are attached form an optionally substituted heteroaromatic or heterocyclic group comprising 4-10 ring members and 0-3 additional heteroatoms selected from the group consisting of O, N and S; the heteroaromatic or heterocyclic group optionally further substituted with one or more optionally substituted aliphatic, alicyclic, heteroaliphatic, heterocyclic, aromatic, heteroaromatic or acyl groups;
$R^a$, for each occurrence, is independently selected from the group consisting of hydrogen and an optionally substituted aliphatic, alicyclic, heteroaliphatic, heterocyclic, aromatic, or heteroaromatic moiety;
$R^b$ and $R^c$, for each occurrence, are independently selected from the group consisting of hydrogen; hydroxy; $SO_2R^d$; and aliphatic, alicyclic, heteroaliphatic, heterocyclic, aromatic, heteroaromatic or acyl moiety;
$R^d$, for each occurrence, is independently selected from the group consisting of hydrogen; —$N(R^e)_2$; aliphatic, alicyclic, heteroaliphatic, heterocyclic, aromatic or heteroaromatic; and
$R^e$, for each occurrence, is independently hydrogen or aliphatic.

17. The method of claim 16 wherein the compound is selected from among

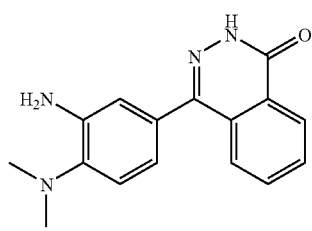

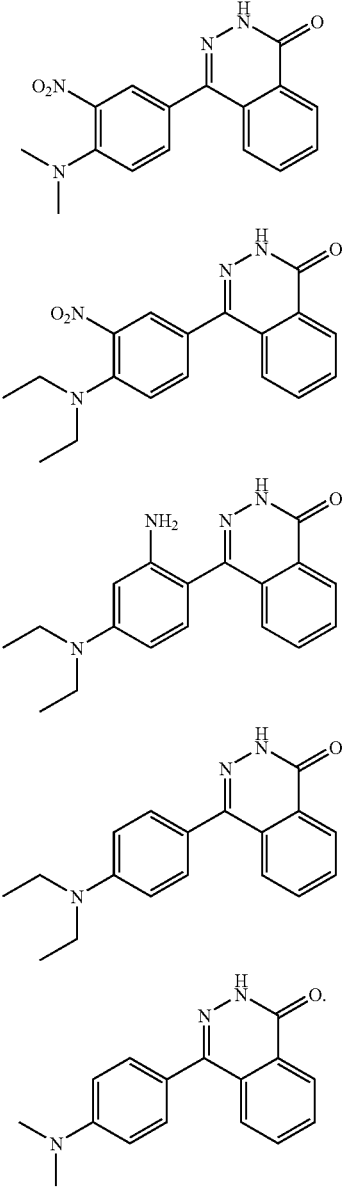

18. The method of claim 16 wherein compound (VIII) has the structure of formula ($IX^A$):

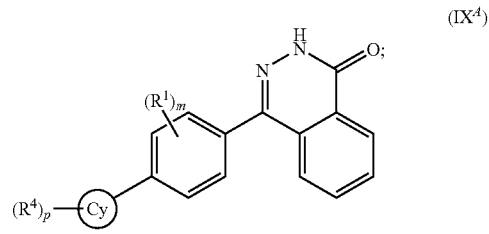

($IX^A$)

wherein Cy is an optionally substituted N-linked 5- to 10-membered heterocyclic group.

19. The method of claim 18 wherein the compound is selected from among

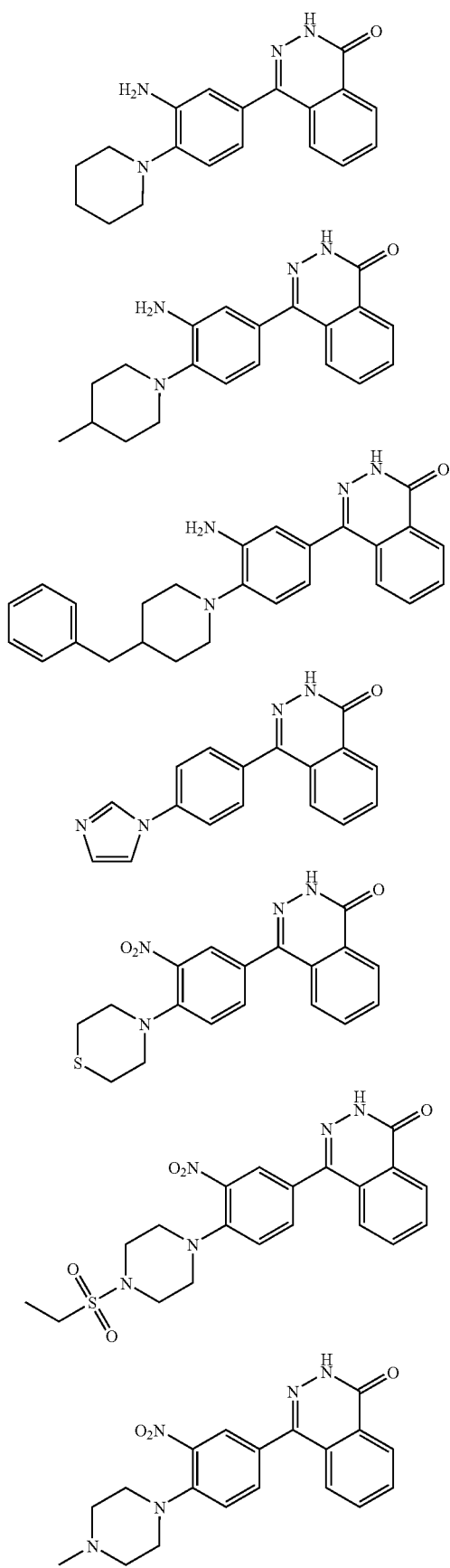
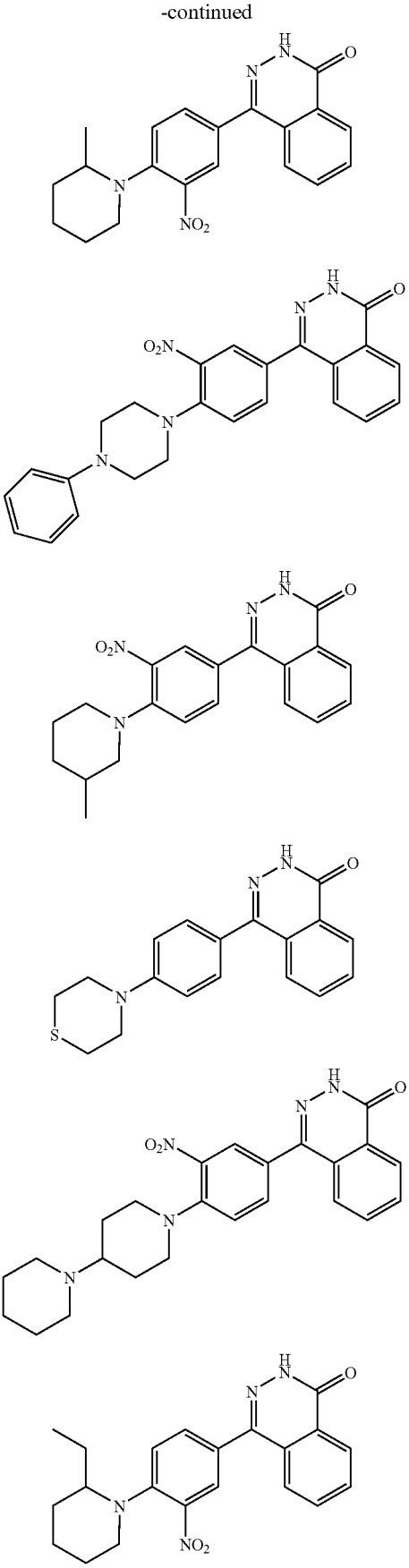

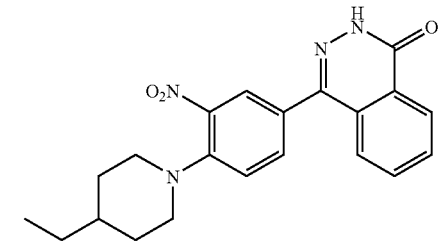
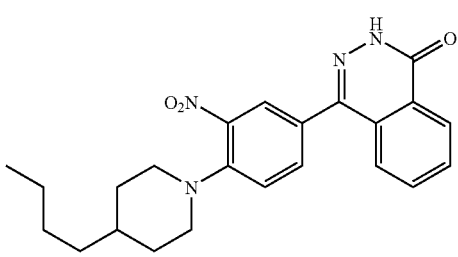
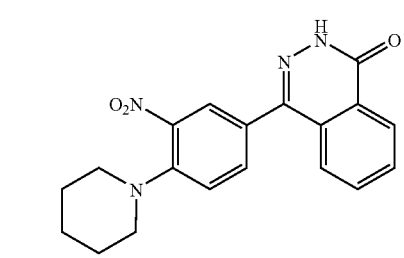
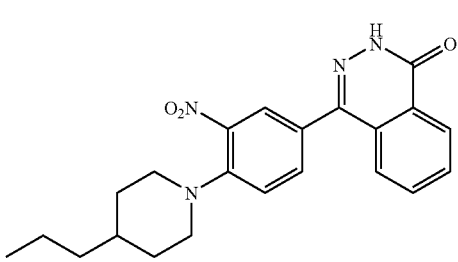
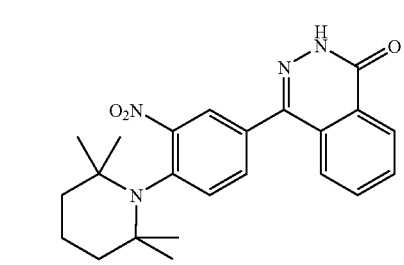
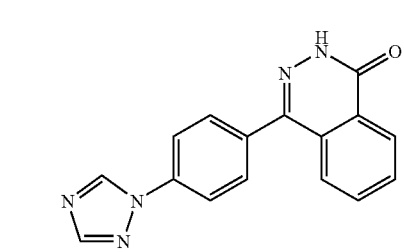
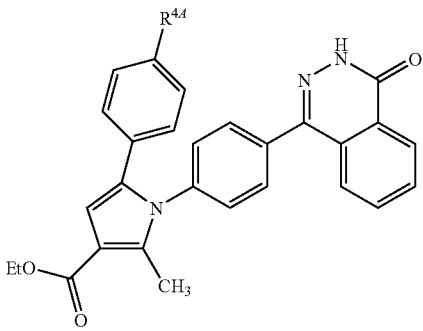
wherein $R^{44}$ is hydrogen, methyl, methoxy, chloro or —NO$_2$
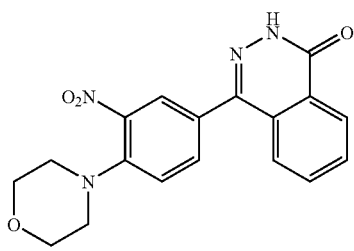
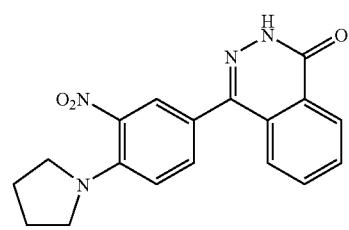
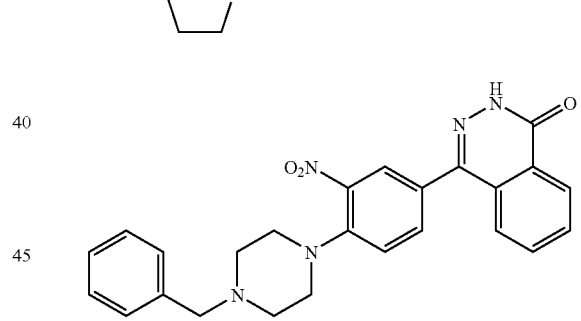
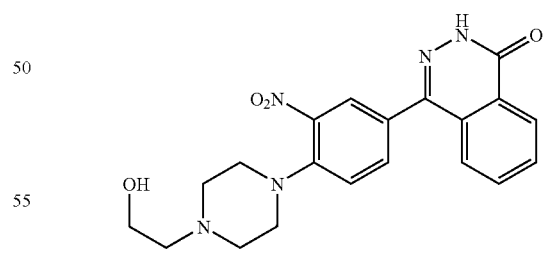
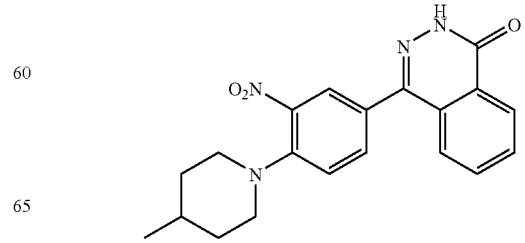

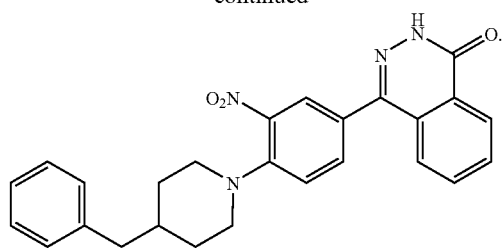
20. The method of claim 16 wherein the compound (VIII) is selected from among
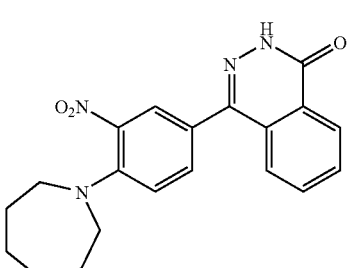
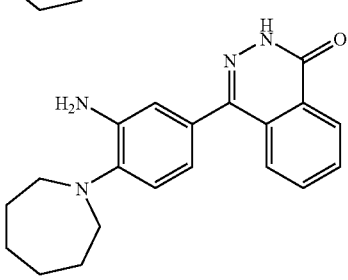
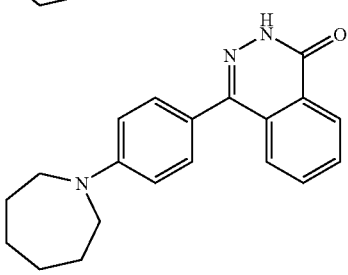
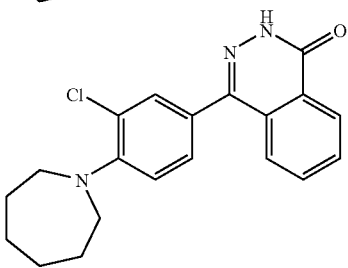
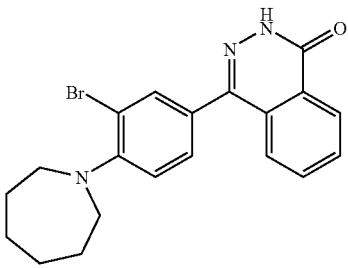
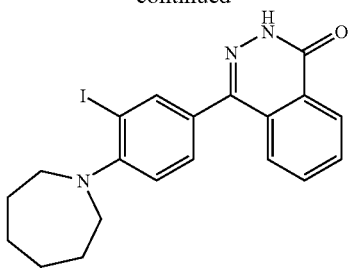
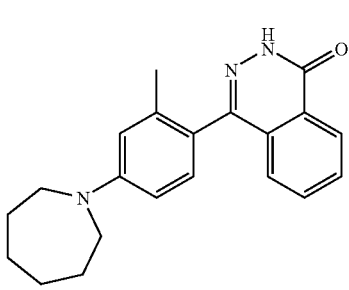
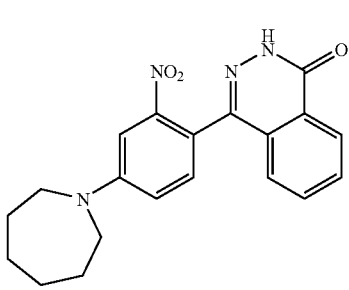
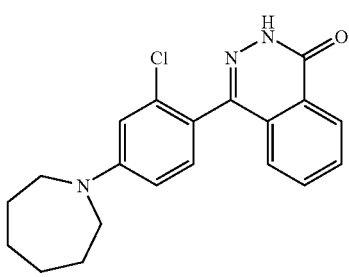
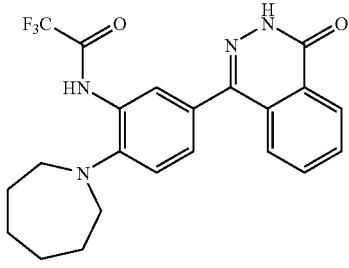
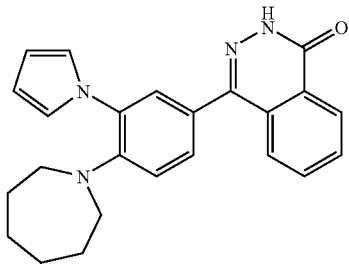

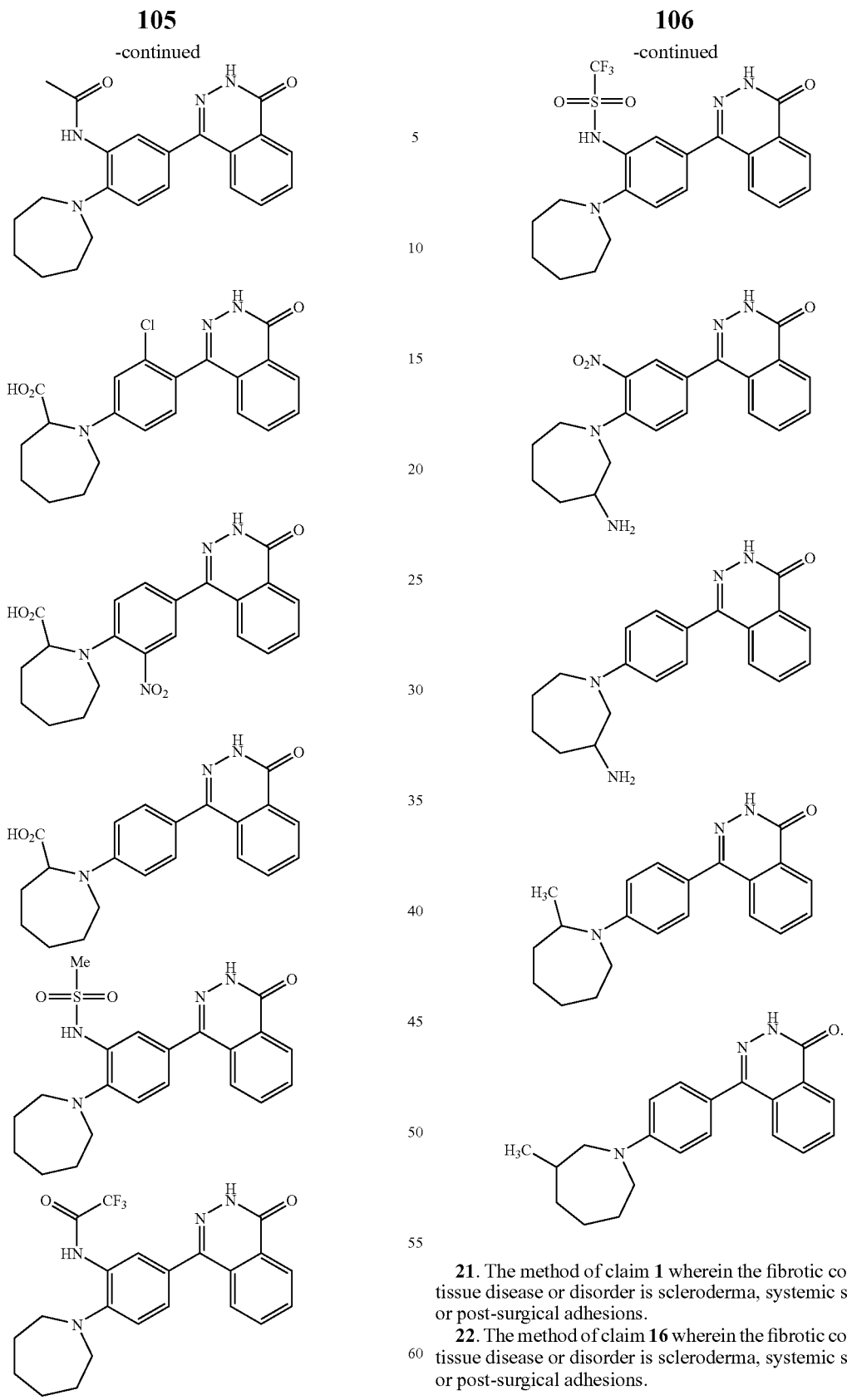
21. The method of claim 1 wherein the fibrotic connective tissue disease or disorder is scleroderma, systemic sclerosis, or post-surgical adhesions.
22. The method of claim 16 wherein the fibrotic connective tissue disease or disorder is scleroderma, systemic sclerosis, or post-surgical adhesions.
* * * * *